(12) United States Patent
Chilkoti et al.

(10) Patent No.: US 8,912,310 B2
(45) Date of Patent: Dec. 16, 2014

(54) PHASE TRANSITION BIOPOLYMERS AND METHODS OF USE

(71) Applicant: Duke University, Durham, NC (US)

(72) Inventors: Ashutosh Chilkoti, Durham, NC (US); Felipe Garcia Quiroz, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/904,836

(22) Filed: May 29, 2013

(65) Prior Publication Data

US 2013/0281624 A1    Oct. 24, 2013

Related U.S. Application Data

(62) Division of application No. 13/245,459, filed on Sep. 26, 2011, now Pat. No. 8,470,967.

(60) Provisional application No. 61/386,002, filed on Sep. 24, 2010.

(51) Int. Cl.
| | |
|---|---|
| *A61K 9/14* | (2006.01) |
| *A61K 47/42* | (2006.01) |
| *C07K 19/00* | (2006.01) |
| *A61K 8/64* | (2006.01) |
| *A61K 8/11* | (2006.01) |
| *C07K 14/78* | (2006.01) |
| *A61K 9/51* | (2006.01) |
| *B82Y 5/00* | (2011.01) |
| *A61K 38/00* | (2006.01) |
| *C07K 14/00* | (2006.01) |

(52) U.S. Cl.
CPC ............. *C07K 14/001* (2013.01); *C07K 19/00* (2013.01); *A61K 8/64* (2013.01); *C07K 2319/00* (2013.01); *A61K 8/11* (2013.01); *C07K 14/78* (2013.01); *A61K 9/5123* (2013.01); *A61K 47/42* (2013.01); *B82Y 5/00* (2013.01); *C07K 2319/21* (2013.01); *A61K 38/00* (2013.01); *A61K 9/5169* (2013.01)
USPC ............................. 530/324; 530/350; 530/322

(58) Field of Classification Search
None
See application file for complete search history.

(56) References Cited

U.S. PATENT DOCUMENTS

| | | | |
|---|---|---|---|
| 4,976,734 | A | 12/1990 | Urry et al. |
| 5,250,516 | A | 10/1993 | Urry |
| 5,336,256 | A | 8/1994 | Urry |
| 6,852,834 | B2 | 2/2005 | Chilkoti |
| 7,429,458 | B2 | 9/2008 | Chilkoti |
| 7,674,882 | B2 | 3/2010 | Kaplan et al. |
| 2005/0255554 | A1 | 11/2005 | Chilkoti |
| 2010/0015070 | A1 | 1/2010 | Bollschweiler et al. |
| 2010/0311059 | A1 | 12/2010 | Didion et al. |
| 2010/0325765 | P1 | 12/2010 | Pait et al. |
| 2012/0121709 | A1 | 5/2012 | Chilkoti et al. |

OTHER PUBLICATIONS

Yoo et al (The Plant Cell (Aug. 2004) 16: 1979-2000).*
Stefl (EMBO reports (2005) 6(1): 33-38).*
Chen, Y. et al. (2009) Bioinspired Modular Synthesis of Elastin-Mimic Polymers to Probe the Mechanism of Elastin Elasticity, J. Am. Chem. Soc.
Christensen, T. et al. (2009) Fusion order controls expression level and activity of elastin-like polypeptide fusion proteins, Protein Science 18:1377-1387.
He, D. et al. (2007) Comparative genomics of elastin: Sequence analysis of a highly repetitive protein, Matrix Biology 26:524-540.
Kyte, J. et al. (1982) A Simple Method for Displaying the Hydropathic Character of a Protein, J. Mol. Biol. 157:105-132.
McDaniel, J.R. et al. (2010) Recursive Directional Ligation by Plasmid Reconstruction Allows Rapid and Seamless Cloning of Oligomeric Genes, Biomacromolecules 11, 944-952.
Meyer, D.E. et al. (2002) Genetically Encoded Synthesis of Protein-Based Polymers with Precisely Specified Molecular Weight and Sequence by Recursive Directional Ligation: Examples from the Elastin-like Polypeptide System, Biomacromolecules 3:357-367.
Nairn, K.M. et al. (2008) A Synthetic Resilin Is Largely Unstructured, Biophysical Journal vol. 95 3358-3365.
Rauscher, S. et al. (2006) Proline and Glycine Control Protein Self-Organization into Elastomeric or Amyloid Fibrils, Structure 14:1667-1676.
Robinet, A. et al. (2005) Elastin-derived peptides enhance angiogenesis by promoting endothelial cell migration and tubulogenesis through upregulation of MT1-MMP, J. Cell Science 118:343-356.
Sheparovych, R. et al. (2009) Stimuli-Responsive Properties of Peptide-Based Copolymers Studied via Directional Growth of Self-Assembled Patterns on Solid Substrate, Biomacromolecules 10:1955-1961.
"Urry, D.W. et al. (1992) Hydrophobicity Scale for Proteins Based on InverseTemperature Transitions, Biopolymers 32:1243-1250.".
Bessa, P.C. et al. (2010) Thermoresponsive self-assembled elastin-based nanoparticles for delivery of BMPs, Journal of Controlled Release 142, 312-318.
United States Patent Office Notice of Allowance for U.S. Appl. No. 13/245,459 dated Feb. 27, 2013 (13 pages).

* cited by examiner

*Primary Examiner* — Jean Witz
*Assistant Examiner* — Mindy Newman
(74) *Attorney, Agent, or Firm* — Michael Best & Friedrich LLP

(57) ABSTRACT

The present disclosure describes environmentally responsive polypeptides capable of displaying stimuli-triggered conformational changes in a reversible or irreversible manner that may be accompanied by aggregation. Polypeptides include a number of repeated motifs and may be elastomeric or non-elastomeric. The polypeptides may be used to deliver therapeutics to a biological site and to develop bioactive polypeptides that are environmentally responsive.

20 Claims, 39 Drawing Sheets

PHASE TRANSITION BIOPOLYMERS AND METHODS OF USE

CROSS-REFERENCE TO RELATED APPLICATIONS

This patent application is a divisional of and claims priority to U.S. patent application Ser. No. 13/245,459 filed Sep. 26, 2011, which claims priority to U.S. Provisional Patent Application No. 61/386,002 filed Sep. 24, 2010, the entire contents of which are incorporated herein by reference in their entireties.

GOVERNMENT SUPPORT

This invention was made with government support under grant no. 5R01-GM61232-08 awarded by the National Institute of Health. The government has certain rights in this disclosure.

BACKGROUND

Elastomeric proteins, and in particular elastin, have been the subject of extensive investigations aimed at a molecular understanding of the structure-function relationship among these proteins, their mechanical properties, environmental sensitivity and self-assembly properties. These studies indicated a role for disordered protein structures in proteins and protein domains, and the identification of short recurrent peptides which were capable of forming protein-polymers with similar structural and environmental properties. A general elastic, environmentally responsive motif Val-Pro-Gly-X-Gly was found in elastin, where X is any amino acid except Proline, and was used to develop elastin-like polypeptides (ELPs) for biotechnological and biomedical uses. Similarly, resilin-like polypeptides displaying mechanical properties comparable to the native resilin protein were made.

Silks, on the other hand, constitute a complex family of proteins that encompasses both elastomeric and non-elastomeric proteins. Elastomeric silks include a highly repetitive GPGGX motif. Studies have indicated that there is an absence of Proline residues in non-elastomeric silks, and that β-sheet structures increase in proportion to the GPGGX content. However, the structures adopted by the abundant GPGGX (SEQ ID NO: 1)/GPGQQ (SEQ ID NO: 2) and GGX repeat units remain unclear. Little progress has been made on the design of recombinant silk-like biomaterials. In addition, elastin remains the only elastomeric repetitive protein successfully reduced to a short motif capable of displaying both elasticity and environmental sensitivity.

After more than three decades of research since the discovery of the environmental sensitivity of elastin monomers (tropoelastin), the more than two decades since the identification of the canonical elastomeric motif VPGXG (SEQ ID NO: 3), and the almost two decades since the generalization of this repeat unit into the canonical ELP motif VPGXG (SEQ ID NO: 3), only a handful of elastin-inspired polypeptides departing from the canonical sequence have been uncovered, namely minor modifications of the canonical motif, such as LPGXG (SEQ ID NO: 4) and IPGXG (SEQ ID NO: 5), and the repeat unit VPAVG (SEQ ID NO: 6). Recent efforts have made use of complex bioinformatics tools to search for sequence conservation, amino acid patterns, and recurrent motifs among elastin proteins from different species; these studies have hinted at the potential functional role of the PG dipeptide in elastin (see, e.g, He, D. et al. (2007) *Matrix Biology* 26:524-540). In a more general approach, studies of similarities in Proline and Glycine content between a large panel of elastomeric proteins from different species including elastin, resilin, gluten, and silks failed to identify first principles for the design of general elastomeric motifs, or to identify and reduce to practice novel motifs responsible for the elasticity and/or environmental sensitivity of these proteins. (see, e.g., Rauscher, S. et al. (2006) *Structure* 14:1667-1676).

SUMMARY

One aspect of the present disclosure describes environmentally responsive polypeptides containing at least ten repeats of an amino acid sequence $Z_1Z_2PXGZ_3$, wherein P is Proline, G is Glycine, X is from 1 to 4 amino acids that are not Proline or Glycine, and $Z_1$, $Z_2$ and, $Z_3$ are each an amino acid is described. Upon stimulation the polypeptide undergoes a conformational change that is accompanied by aggregation.

Another aspect describes environmentally responsive polypeptides that contain at least ten repeats of an amino acid sequence $Z_1PXGZ_2RGZ_3$, wherein P is proline, G is glycine, R is arginine, D is aspartate, X is from 0 to 4 amino acids that are not proline or glycine, and $Z_1$ and $Z_2$ are each an amino acid, and $Z_3$ is an amino acid such as aspartate (D). Upon stimulation the polypeptide undergoes a conformational change that is accompanied by aggregation.

Another aspect describes environmentally responsive polypeptides comprising at least ten sequences selected from VGAPVG, LGAPVG, VPSALYGVG, VGPAVG, VTPAVG, VPSDDYGQG, VPSDDYGVG, TPVAVG, VPSTDYGVG, VPAGVG, VPTGVG, VPAGLG, VPHVG, VHPGVG, VPGAVG, VPGVAG, VRPVG, GRGDSPY, GRGDSPH, GRGDSPV, GRGDSPYG, RPLGYDS, RPAGYDS, GRGDSYP, GRGDSPYQ, GRGNSPYG, GRGDAPYQ, VPHSRNGG, VPHSRNGL, VPGHSHRDFQPV-LHLVALNSPLSGGMRG, HTHQDFQPVLHLVALNT-PLSGGMRGIRPGG, FEWTPGWYQPYG or a combination thereof. Upon stimulation the polypeptide undergoes a conformational change that is accompanied by aggregation.

Another aspect describes environmentally responsive polypeptides that contain at least ten PG motifs, and at least nine spacer sequences between the PG motifs. The spacer sequences do not include a PG motif and are between five and thirty amino acid residues in length. Upon stimulation the polypeptide undergoes a conformational change that is accompanied by aggregation.

Another aspect describes an environmentally responsive polypeptide which upon stimulation undergoes a conformational change that is accompanied by aggregation and includes at least ten repeats of an amino acid sequence $Z_1PXGZ_2Z_3Z_4Z_5$, wherein P is proline, G is glycine, X is from 0 to 4 amino acids that are not proline or glycine, and $Z_1$, $Z_2$, $Z_3$, $Z_4$ and $Z_5$ are each an amino acid. $Z_2$ may be optionally absent. The amino acid sequence includes an arginine, as well as either a serine or aspartate, or both serine and aspartate, and at least one hydrophobic residue selected from valine, leucine, isoleucine, histidine, tyrosine, tryptophan and alanine. The aspartate may be optionally substituted with glutamate.

Another aspect describes methods of effecting a conformational change in a polypeptide by exposing the polypeptide to a stimulus such that the polypeptide undergoes a conformational change in response to the stimulus. The conformational change may be accompanied by aggregation or solubilization.

Another aspect describes nanoparticles formed from an environmentally responsive polypeptide which may encapsulate a therapeutic for delivery to a biological site.

Another aspect describes methods of delivering therapeutics to biological sites by contacting the biological site with a nanoparticle formed from an environmentally responsive polypeptide, wherein the nanoparticle receives a stimulus at the biological site and disassembles.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component is labeled in every drawing. The foregoing objects, features and advantages of the present disclosure will become more apparent from a reading of the following description in connection with the accompanying drawings in which:

FIG. 1C shows the localization of the VPGXG (SEQ ID NO: 3) motifs as a digital signal where all residues forming part of the motif have a value of 1 and 0 otherwise; the $P(X_n)G$ motifs are digitized such that the signal is 1 for Proline and subsequent residues within a continuous $P(X_n)G$ motif and 0 for G residues within the motif or any non-motif amino acid along the sequence.

FIG. 3C shows quantitation of VPG, VPGXG (canonical ELP motif; SEQ ID NO: 3) and PG motifs in elastin from different species. FIG. 3D shows the percentage of $P(X_n)G$ motifs preceded by Glycine to yield $GP(X_n)G$ motifs, as shown for n=0, n=1, n=2 and n≥3 (indicated as $PGX_nG$ in the figure). FIG. 3E shows the average distance between $P(X_n)G$ motifs with either n=0 or n=1 compared with average distance between a control $P(X_n)G$ motif.

Note that threonine is more hydrophobic than Gly according to Urry's hydrophobicity scale (see, Urry, D. W. et al. (1992) *Biopolymers* 32:1243-1250).

Figure 18:
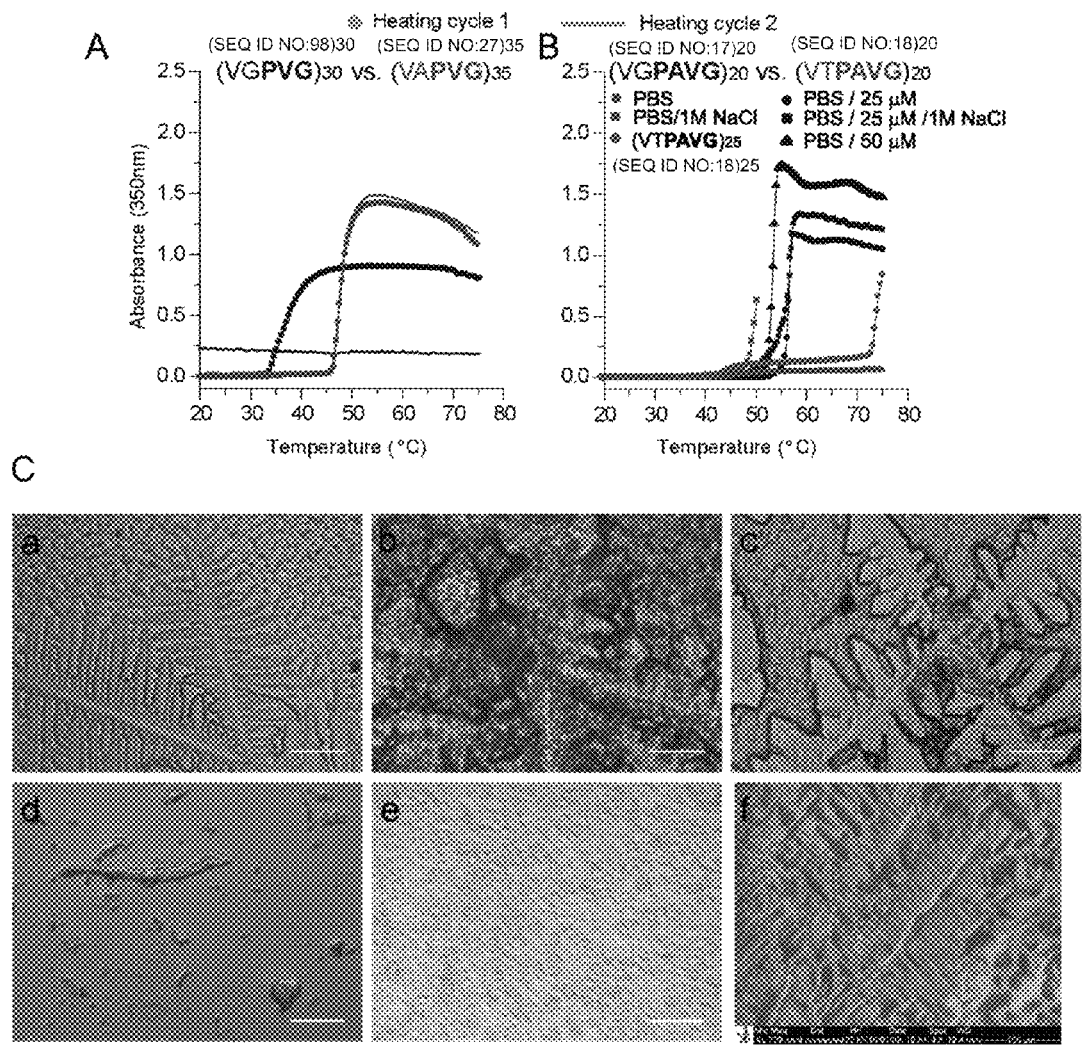
FIG. 18 depicts graphs and photographs showing modified retro-EIPs unravel the role of Gly at Pm1 in the environmental sensitivity and self-assembly properties of EIPs comprised of minima functional PX$_n$G motifs. Substituting a hydrophobic residue (relative to Gly) for Gly residue at Pm1, results in an unexpected dramatic increase in the Tt of the modified retro-EIP (shown in red), which restores the transition temperature to a value closer to that of the parent EIP (FIGS. 17A-B) and the sensitivity to changes in buffer ionic strength (B), and suppresses heat-irreversible phase transition behavior (A). (C) Phase contrast microscopic analysis of the structures formed upon self-assembly of EIP constructs drying on glass surfaces. (Ca) Self-assembled fractals formed by EIP (VPAVG)$_{45}$ (SEQ ID NO: 6)$_{45}$ with a PX$_1$X$_2$G (SEQ ID NO: 16) minima functional motif. (Cb) Retro-EIP (VGPAVG)$_{20}$ (SEQ ID NO: 17)$_{20}$ where Pm1 is Gly does not form fractal structures and assembles into fibrillar-like densely packed structures. (Cc) The modified retro-EIP (VTPAVG)$_{20}$ (SEQ ID NO: 18)$_{20}$ shows restored self-assembly into fractal structures. (Cd) Upon rehydration of the imaged droplets. Large fibrils are observed for the retro-EIP (Cd), while only small submicron aggregates (evidenced in the roughness of the surface) are observed for the modified retro-EIP (Ce). (Cf) Environmental scanning electron microscopy shows similar fractal structures formed by an elastin-like polypeptide (with motif VPGXG (SEQ ID NO: 3), where X=[A:G]) when frozen-dried above its transition temperature. Scale bar is 50 µM.
Figure 19:
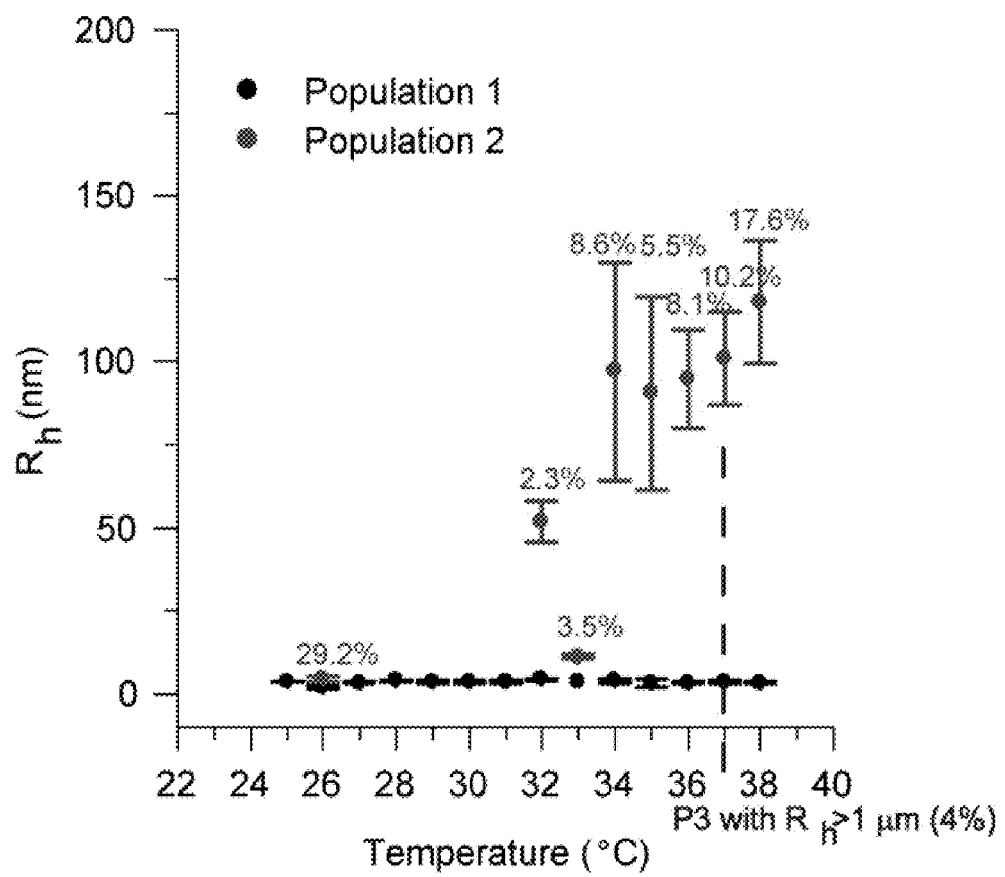

FIG. 19 is a graph showing self-assembly of EIP with sequence (VTPAVG)$_{20}$, comprised of a minima functional motif PX$_1$X$_2$G (SEQ ID NO: 16), into nano-structures. The formation of a third population (P3) (~4% mass), with hydrodynamic radius larger than 1 mm, for temperatures above 38° C., reduced the quality of the DLS data and prevented data acquisition at higher temperatures. Noteworthy, turbidity profiles demonstrate stable light scattering properties for temperature between 40° C. and 75° C., presumably arising from small micrometer sized particles; major aggregation is expected to occur at ~80° C., considering that major aggregation of (VPTAVG)$_{25}$ ((SEQ ID NO: 18)$_{25}$) occurs at ~72° C. (FIG. 18B). Sample was prepared at 50 µM in PBS.

Figure 20:
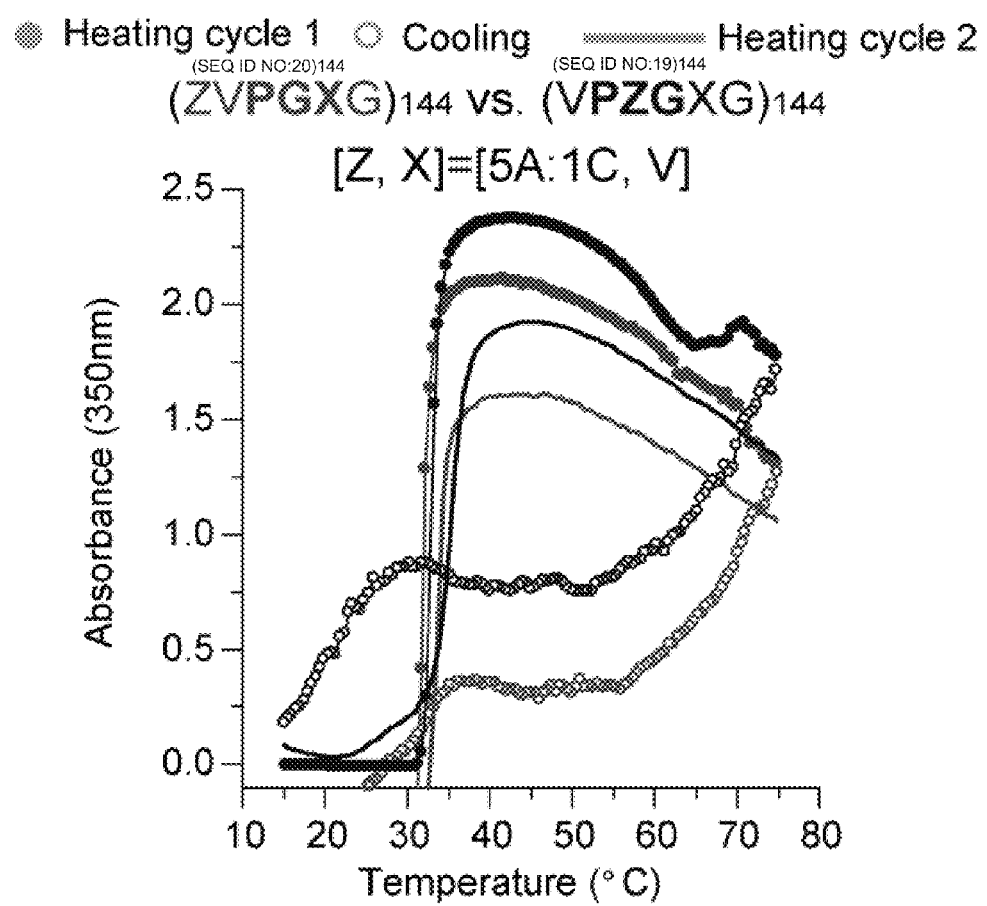

FIG. 20 is a graph showing thermoresponsive behavior of self-cross-linkable in situ gelling materials composed of elastomeric-inspired polypeptides. Cysteine residues were incorporated into EIPs displaying PG and PX$_1$G motifs to enable their self-cross-linking via disulfide bonding. The primary sequence of these protein polymers is described as (ZVPGXG)$_{144}$ and (VPZGXG)$_{144}$ ((SEQ ID NO: 19)$_{144}$), where [Z,X]=[5A:1C,V], that is 1 Cys every 5 Ala residues in the Z position, and a Cal in the X position for every repeat, for a total of 144 repeat units. Noteworthy, the EIP (ZVPGXG)$_{144}$ ((SEQ ID NO: 20)$_{144}$) was designed to display the bioactive motif GXXPG (SEQ ID NO: 21) responsible for elastin bioactivity. The inverse transition temperature of these self-cross-linkable EIPs was engineered to occur below body temperature to allow for rapid coacervation before the onset of gelation via disulfide bonding.

Figure 21:
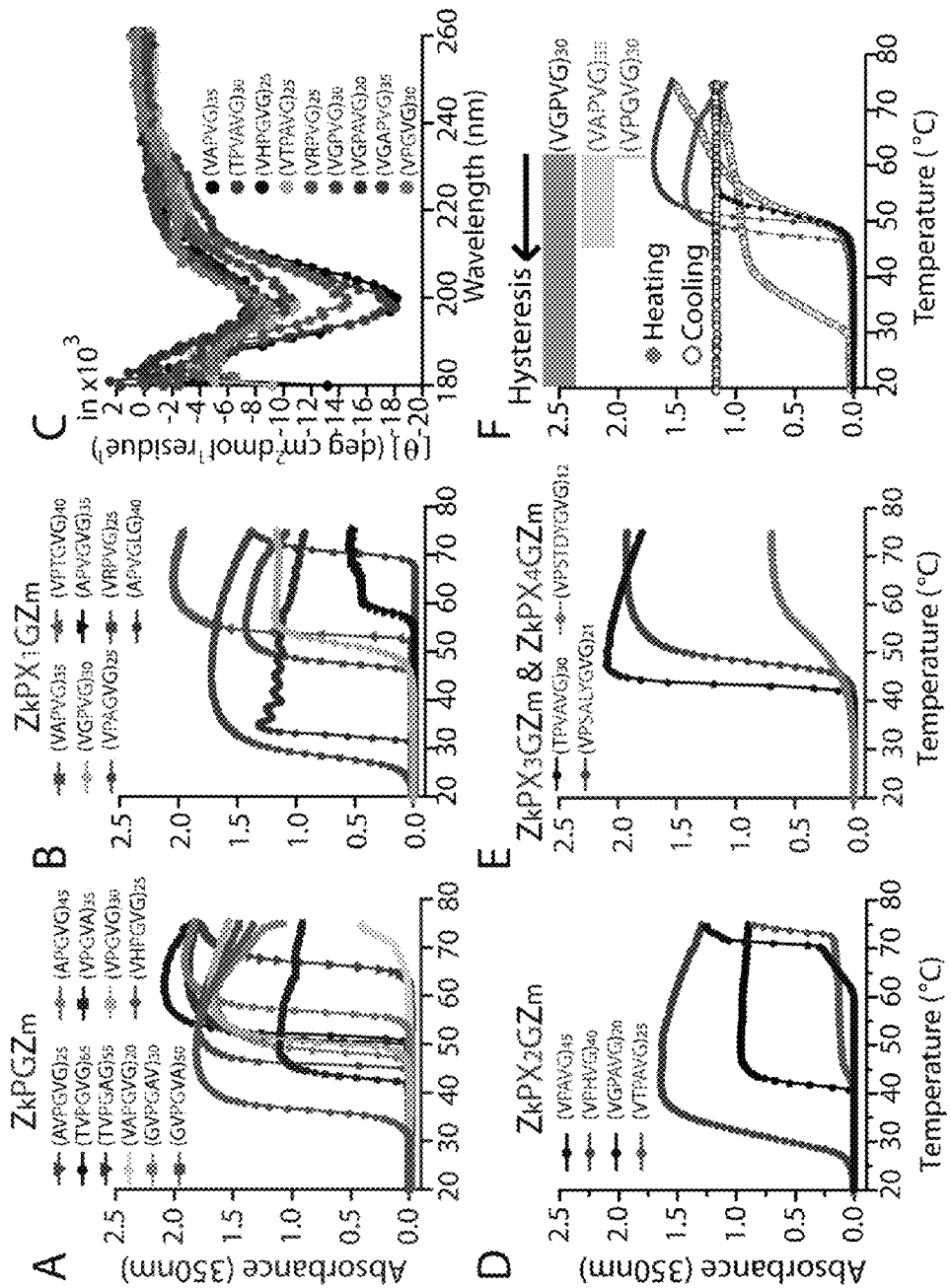

FIG. 21. depicts graphs showing multiple Pro and Gly arrangements besides the canonical Pro-Gly dipeptide are conducive to unstructured protein-polymers that display "smart" behavior. Protein-polymers with periodic Pro and Gly residues arranged as PX$_n$G units, where n=0 (A), 1 (B), 2 (D), 3 and 4 (E), and having pentapeptide, hexapeptide and nonapeptide repeat units display thermally-triggered phase transition behavior. These protein-polymers lack ordered secondary structures as shown by their circular dichroism spectra characteristic of disordered proteins (C). We found that protein-polymers in A, B, D and E fall within any of three types of phase transition behavior, corresponding to three degrees of hysteresis in the reversibility of their thermally-triggered phase transition: zero, finite and heat-sensitive, infinite hysteresis (F). All turbidity measurements were conducted in PBS at a polypeptide concentration of 50 µM, except for VRPVG (+1M NaCl), VAPGVG (+0.5 M NaCl), APGVG (+2 M NaCl) and VPSALYGVG (+8 M urea). CD studies were conducted in water at a polypeptide concentration of 5 µM.

Figure 22:
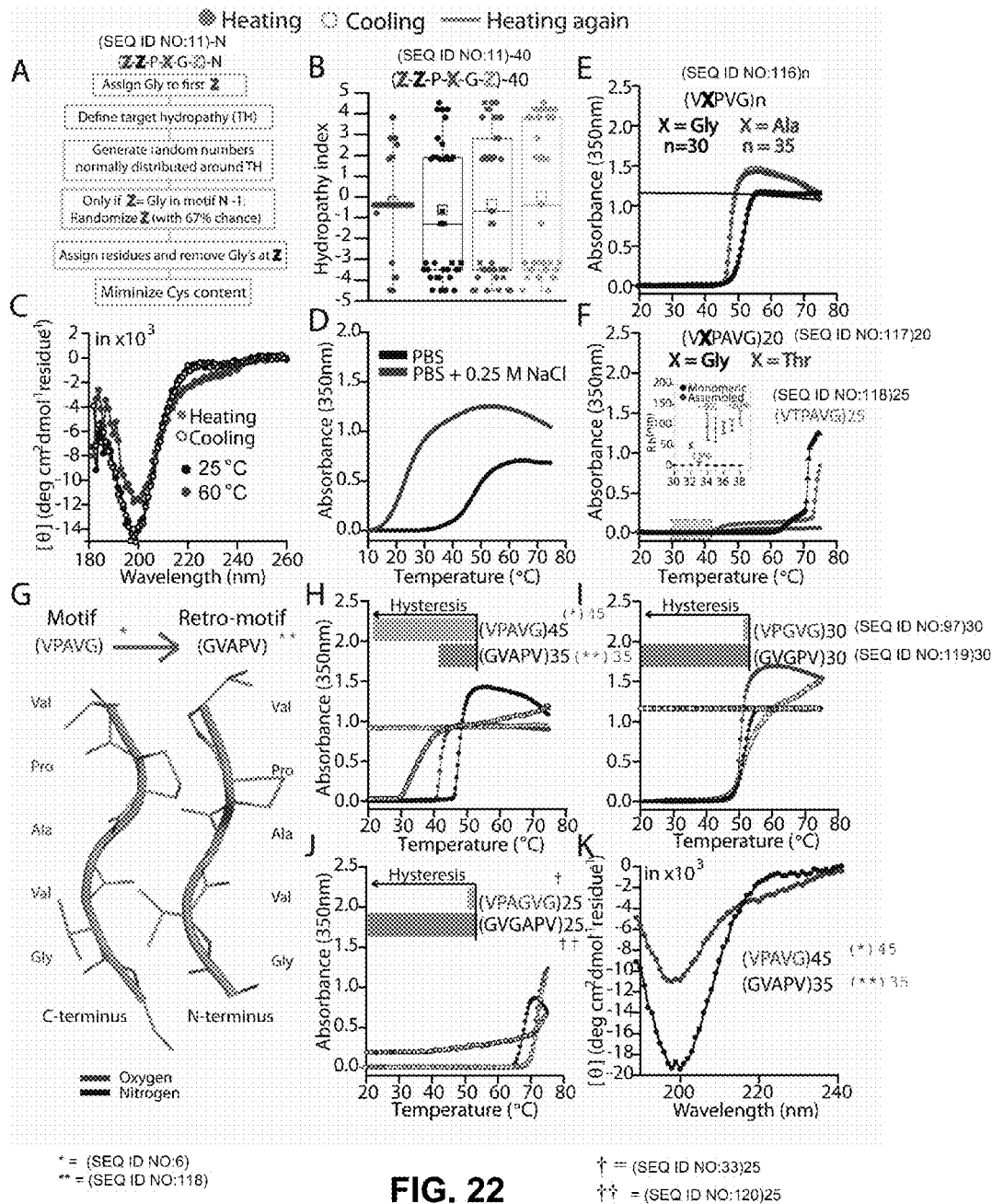

FIG. 22. Depicts graphs showing that "smart" biopolymers exhibit protein-like features. A simple method (A) was applied which was inspired in the do's and don'ts of non-fibrillar Pro and Gly-rich proteins to favor protein disorder, to engineer a protein-sized, 240-residue-long protein-polymer with a target hydropathy—equivalent to transition temperature in of 37° C. and composed of 40 hexapeptide motifs containing Pro-X-Gly units with randomly selected amino acids spanning a broad range of hydropathies (B). This protein-sized biopolymer behaved as an intrinsically disordered protein (C) and exhibited "smart", phase transition behavior (D). Gly residues preceding a PX$_n$G unit modulated the phase transition behavior of "smart" protein-polymers (E-F). The inset of (F) shows the thermally-triggered assembly of a n environmentally responsive polypeptide with repeat unit VTPAVG that was not observed for the Gly-variant VGPAVG. (G) Backbone-reversed protein-polymers present identical amino acid patterns, which were exemplified with the structure of a "smart" pentapeptide motif and its retro-motif as observed in the crystal structure of two different proteins (PDB id 3MKR_B and 1OZP, respectively). Changes in the phase behavior of "smart" protein-polymers on backbone-reversal (H-J) were observed—mostly changes in the hysteresis of the transition—as well as large changes in the ensemble of dynamic conformers that characterize their secondary structure (K).

Figure 23:
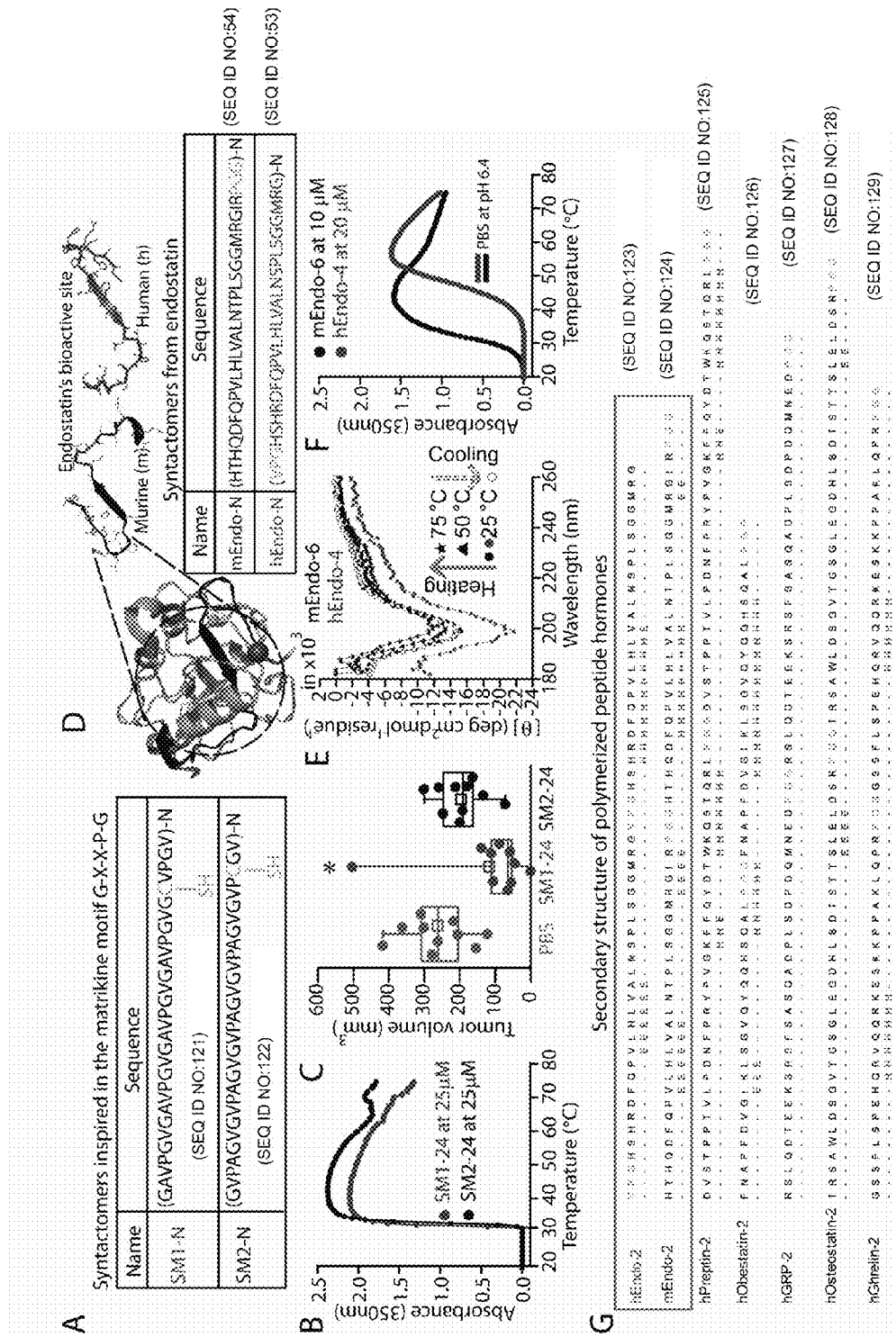
Figure 27:
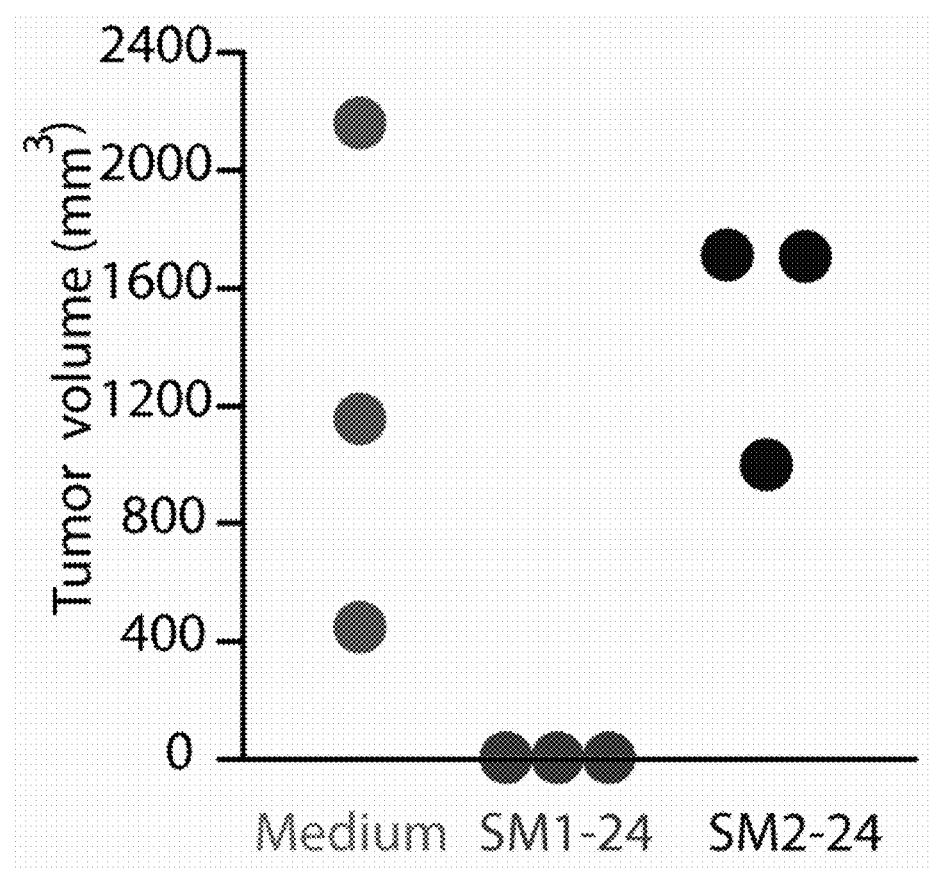

FIG. 23. Depicts graphs showing environmentally responsive polypeptides having a syntax that is truly protein-like. First, two protein-polymers were designed with identical amino acid composition (A), "smart" matrikine 1 (SM1) and SM2, where only SM1 conforms to a bioactive motif GXXPG found in various extracellular matrix proteins. These materials were engineered to self-gel upon subcutaneous injection by enabling the formation of disulfide bonds upon phase transition through carefully spaced Cys residues. (B) SM1 and SM2 displayed identical phase transition behavior in PBS (pH 7.4) and coacervated below body temperature. (C) The bioactive SM1 (at 350 µM in PBS) prevented tumor growth when used as vehicle for the inoculation of 0.5×10$^5$ HT-1080 tumor cells into the leg (n=10) of nude mice, whereas the nonbioactive SM2 (at 350 µM in PBS) had no effect on tumor growth. Asterisk (*) indicates statistical significance with a 95% confidence using a Bonferroni test to compare the mean tumor volumes after 17 days of tumor inoculation. FIG. 27 shows the anti-tumor activity of SM1-24 for tumors inoculated in the back of nude mice. In a second example, the complex and long peptide sequences forming the bioactive sites of murine (PDB file: 1DY0) and human endostatin (PDB file: 1BNL) (D), which amino acid sequences are shown in blue and red, respectively, are conferred with "smart" behavior on polymerization. These environmentally responsive polypeptides behave as intrinsically disordered proteins and are highly stable in aqueous solution (E), and display inverse phase transition behavior (FIG. 38) (F). The ability to design "smart" protein-polymers with monomer units that have defined, local secondary structure propensities, as in human and murine endostatin (G, within the box), may enable the development of a broader set of "smart", drug-like protein-polymers derived from the growing list of polypeptide hormones that remain partially disordered on polymerization (G). Additional peptide hormones of interest were studied. Secondary structures were predicted using the Jnet algorithm, where 'H' is α-helix, 'E' is β-sheet, and '-' is random coil. Circular dichroism data were obtained in water at a polypeptide concentration of 5 µM. Images of the 3D structures of endostatin were rendered using PyMOL.

Figure 24:
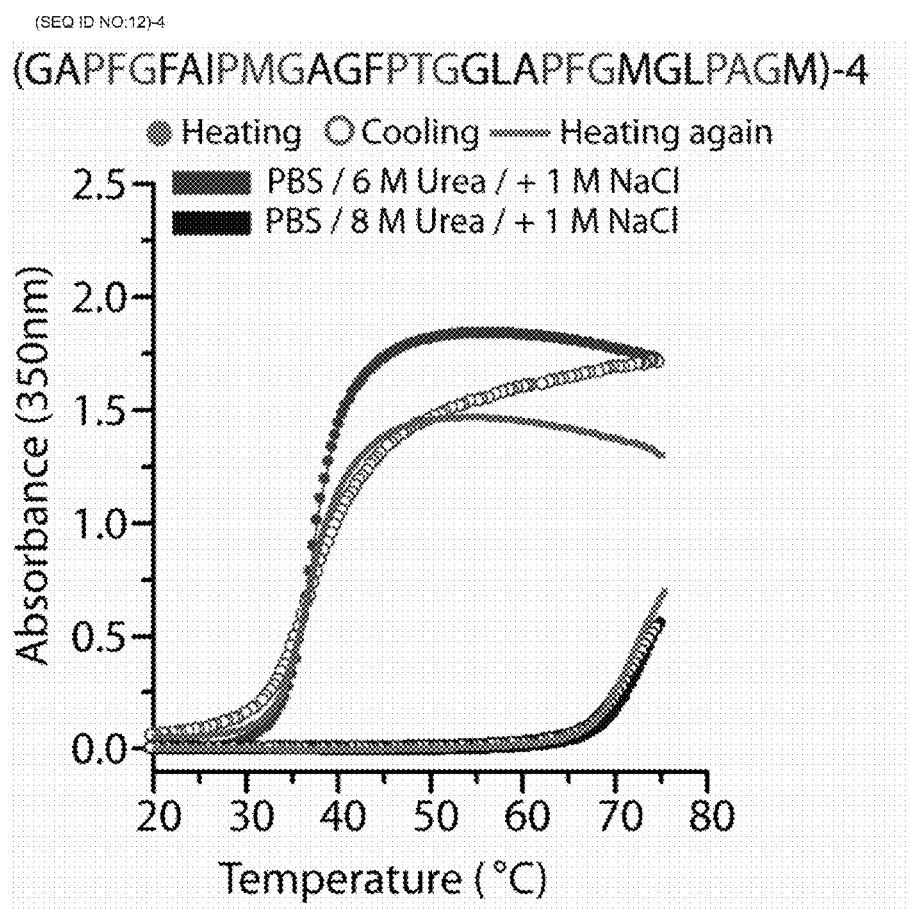

FIG. 24 is a graph showing environmentally responsive "smart" behavior of a polypeptide with a non-repetitive, 36 amino acid long repeat unit, designed as in FIG. 22A, but using a target hydropathy of 2, according to Kyte-Dolittle's scale.

Figure 25:
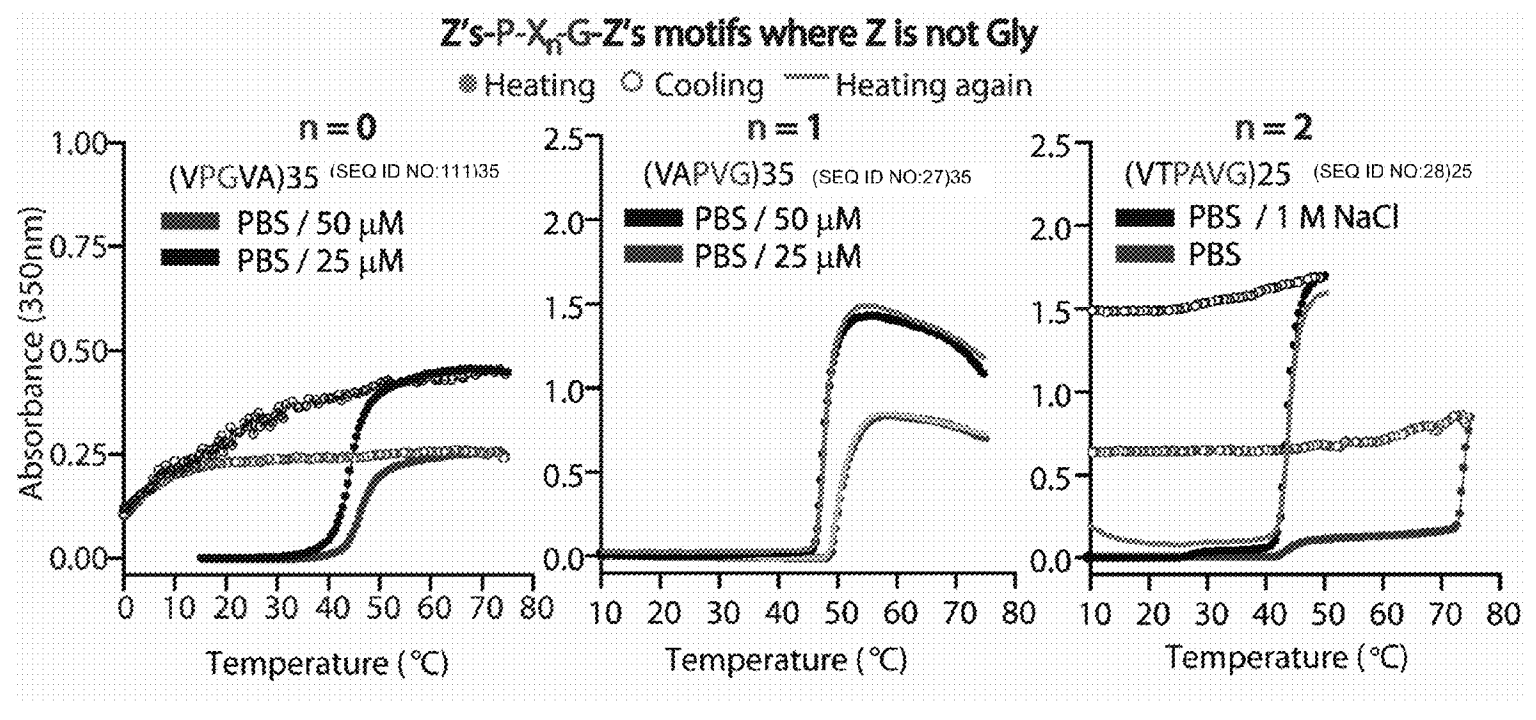

FIG. 25 depicts graphs showing that high Gly content is not a prerequisite for the design of environmentally responsive polypeptides. Gly residues are not a sine qua non element for the design of protein-polymers that display fully reversible phase transition behavior. Protein-polymer concentration was 50 µM unless otherwise indicated.

Figure 26:
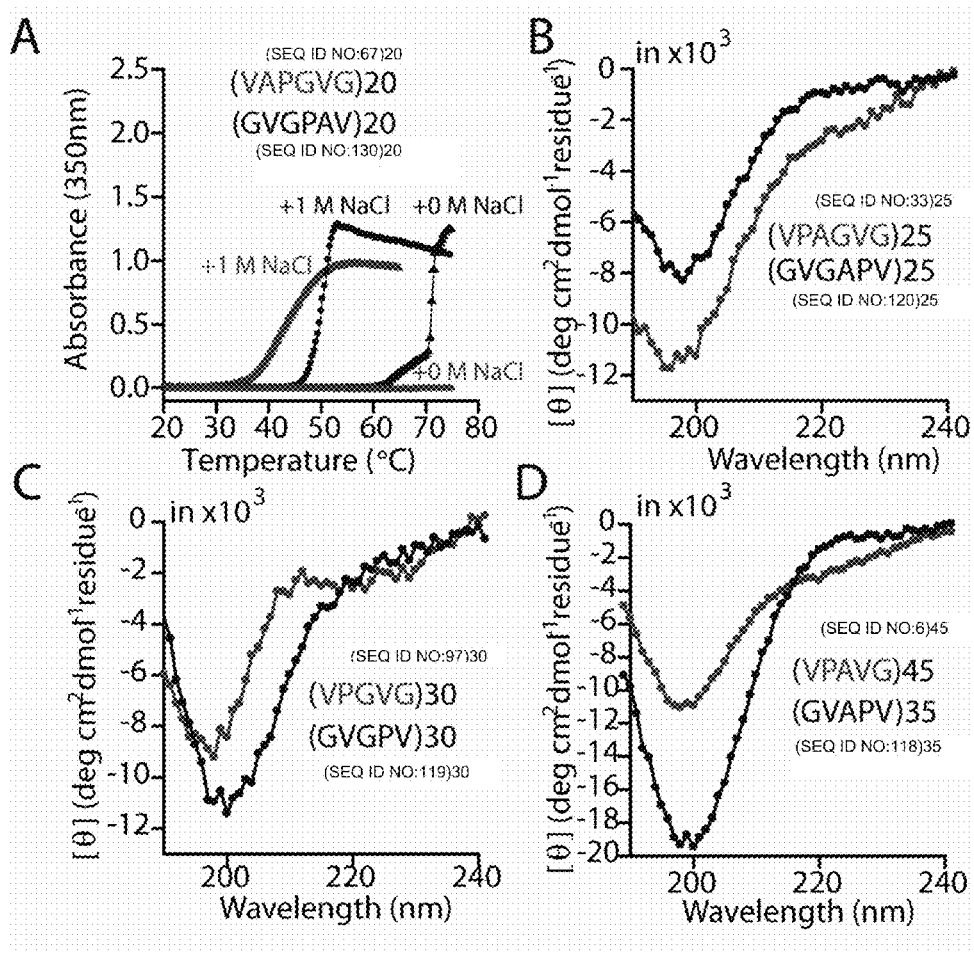

FIG. 26 depicts graphs showing backbone reversal of an environmentally responsive polypeptide results in pronounced changes in phase behavior and secondary structure propensities. (A) Changes in phase behavior for a fourth test-in-case of the effect of backbone reversal on phase behavior. The retro-polypeptide showed a greater propensity for coacervation but reduced sensitivity to ionic strength. (B-D) The circular dichroism spectra of three pairs of environmentally responsive polypeptides and their respective retro-motifs revealed significant changes in the overall disorder of the structures (negative peak at ~200 nm) and β-turn content (negative region around 210 nm). Turbidity studies were conducted in PBS (with salt concentrations as indicated) at a polypeptide concentration of 50 µM. CD studies were done in water at a polypeptide concentration of 5 µM.

FIG. 27 is a graph showing that a polypeptide containing a matrikine motif GXXPG, SM1-24 (250 µM in PBS), prevented the grafting of 1×10⁶ HT1080 tumor cells inoculated into the back of nude mice. A control polypeptide, SM2-24 (250 µM in PBS), with a disrupted motif but identical phase transition behavior (FIG. 23) had no effect on tumor growth. Tumor volumes were measured 19 days after inoculation.

Figure 28:
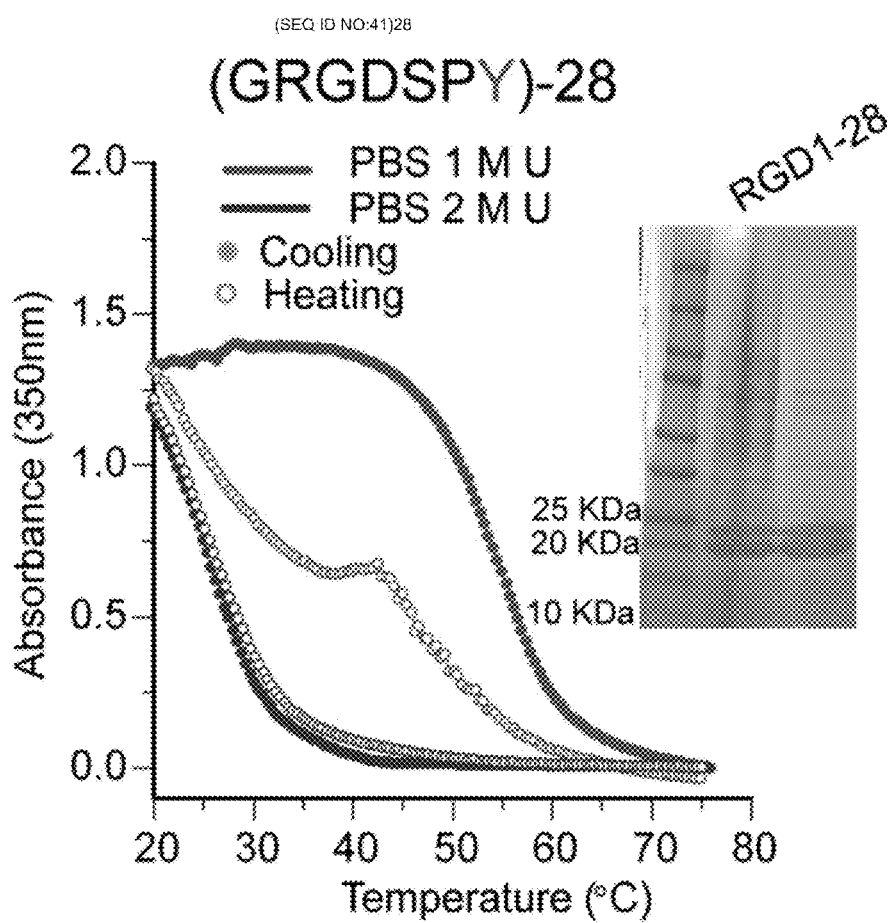

FIG. 28 depicts a graph and photograph showing that environmentally responsive polypeptides may be designed to display UCST behavior.

Figure 29:
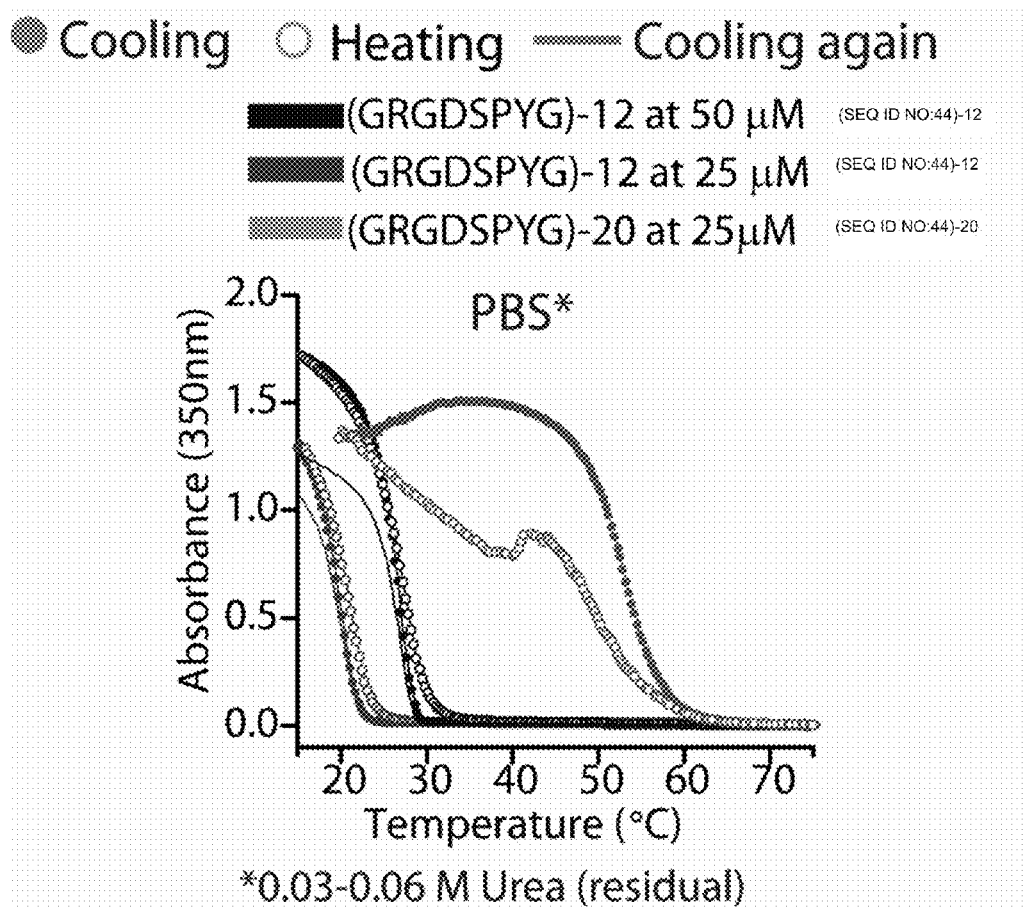

FIG. 29 is a graph showing reversible UCST behavior in PBS which behavior may be tuned by polypeptide concentration and the number of repeating units.

Figure 30:
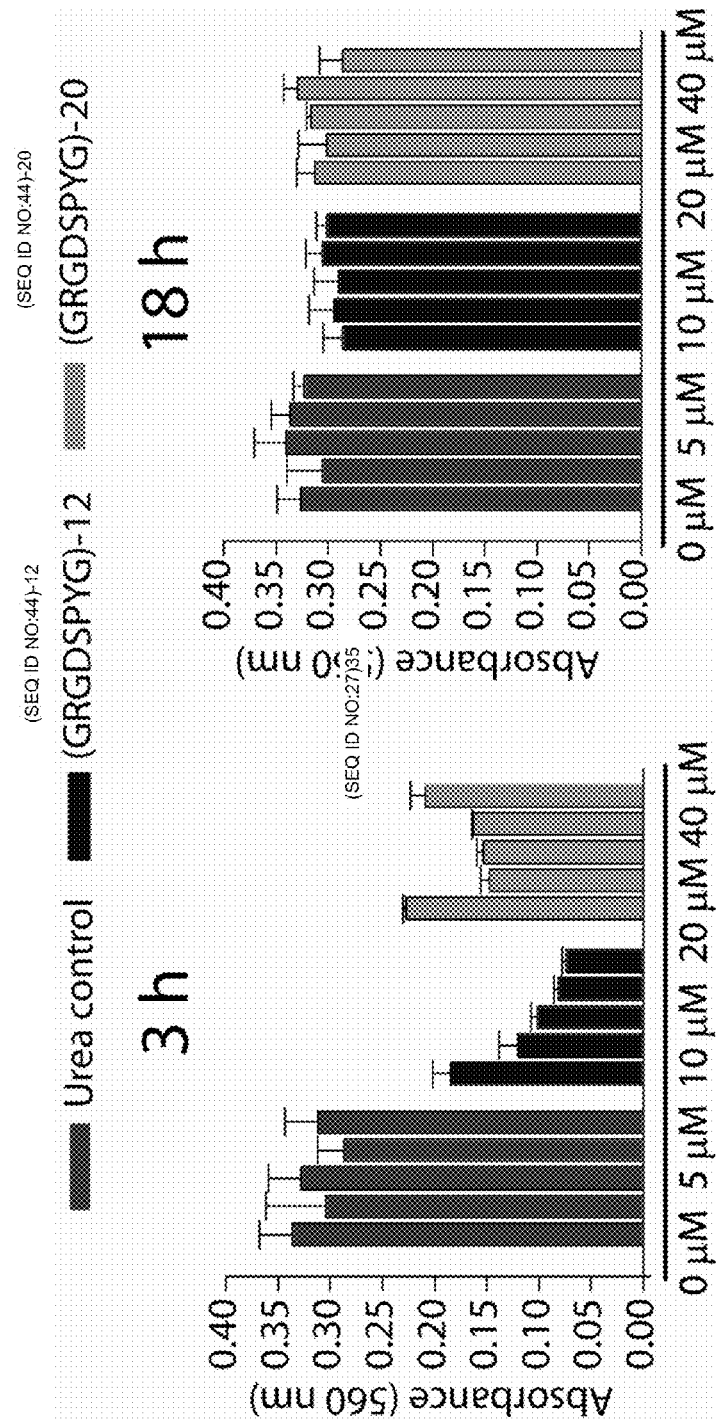

FIG. 30 is a graph showing bioactive environmentally responsive polypeptides incorporating the peptide drug GRGDSP.

Figure 31:
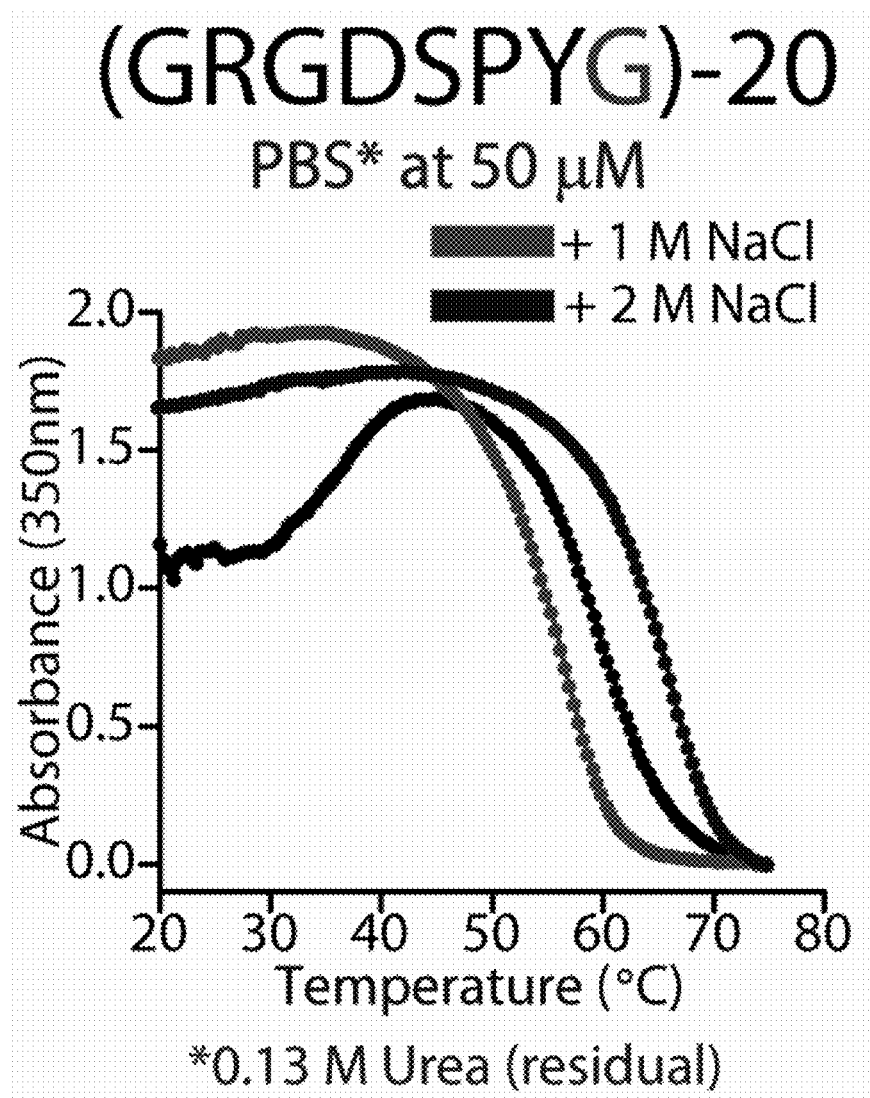

FIG. 31. is a graph showing the UCST behavior of environmentally responsive polypeptides containing RGD tripeptides.

Figure 32:
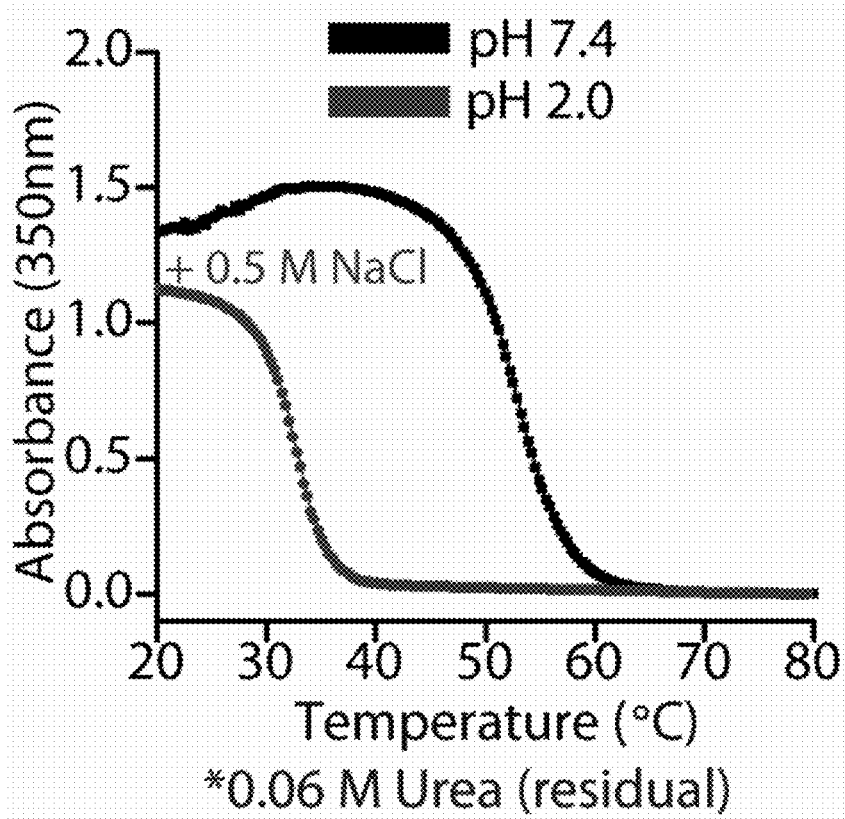

FIG. 32 is a graph showing the UCST behavior of environmentally responsive polypeptides may be modulated by electrostatic interactions between positively and negatively charged amino acids within the sequence.

Figure 33:
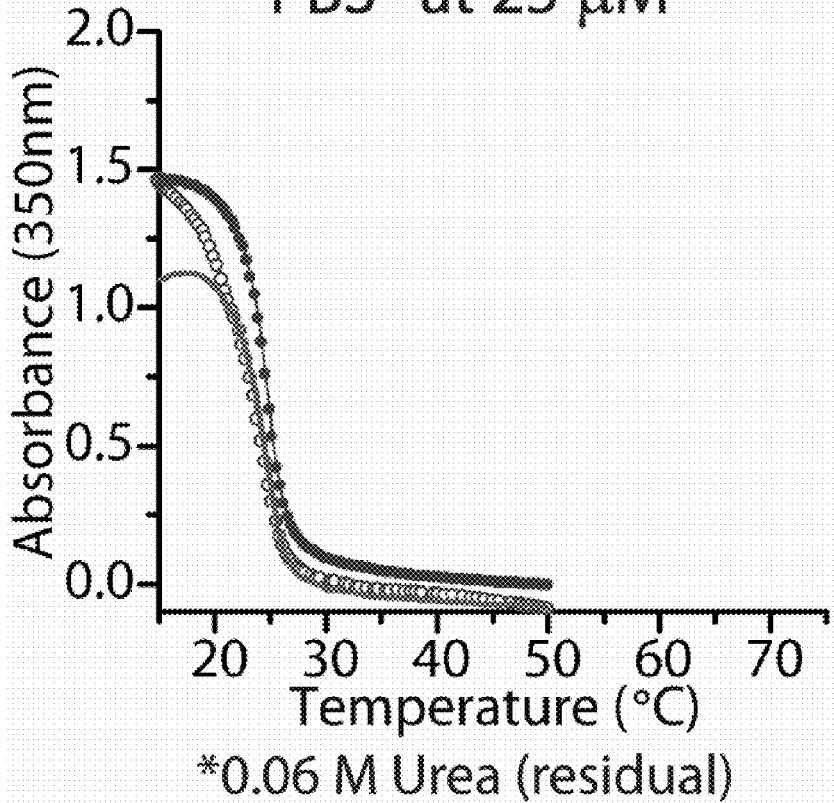

FIG. 33 is a graph showing the UCST behavior of environmentally responsive polypeptides does not require electrostatic interactions.

Figure 34:
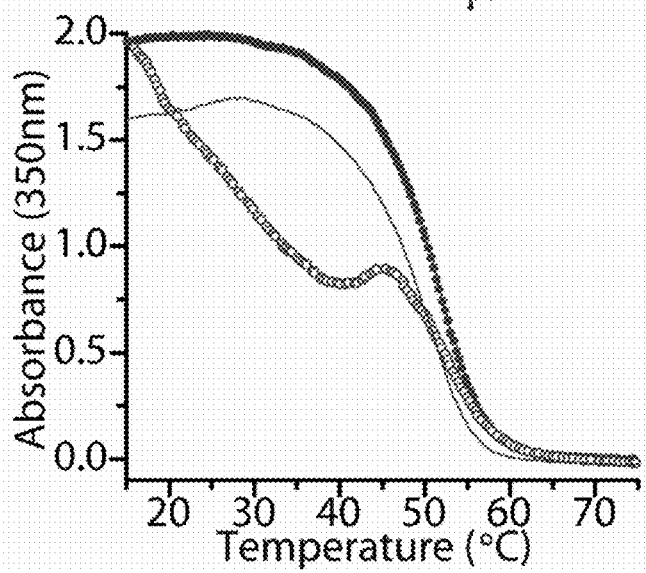

FIG. 34 is a graph showing that RGD-containing environmentally responsive polypeptides that display UCST behavior are compatible with multiple arrangements of Pro and Gly residues.

Figure 35:
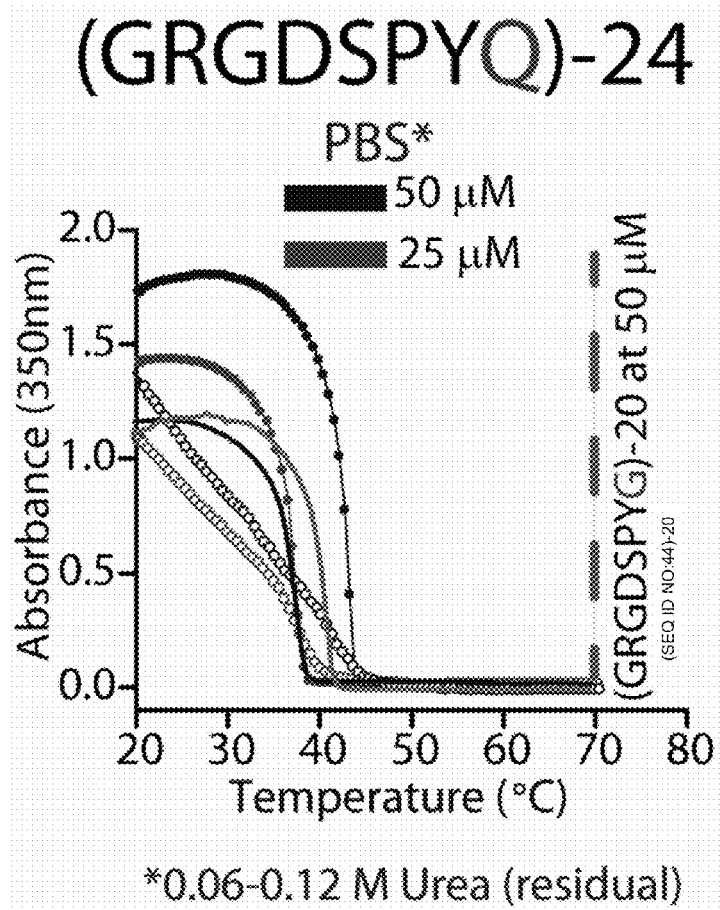

FIG. 35 is a graph showing that the UCST behavior of environmentally responsive polypeptides can be tuned by adjusting the hydrophobicity of the residues comprising the repeating unit.

Figure 36:
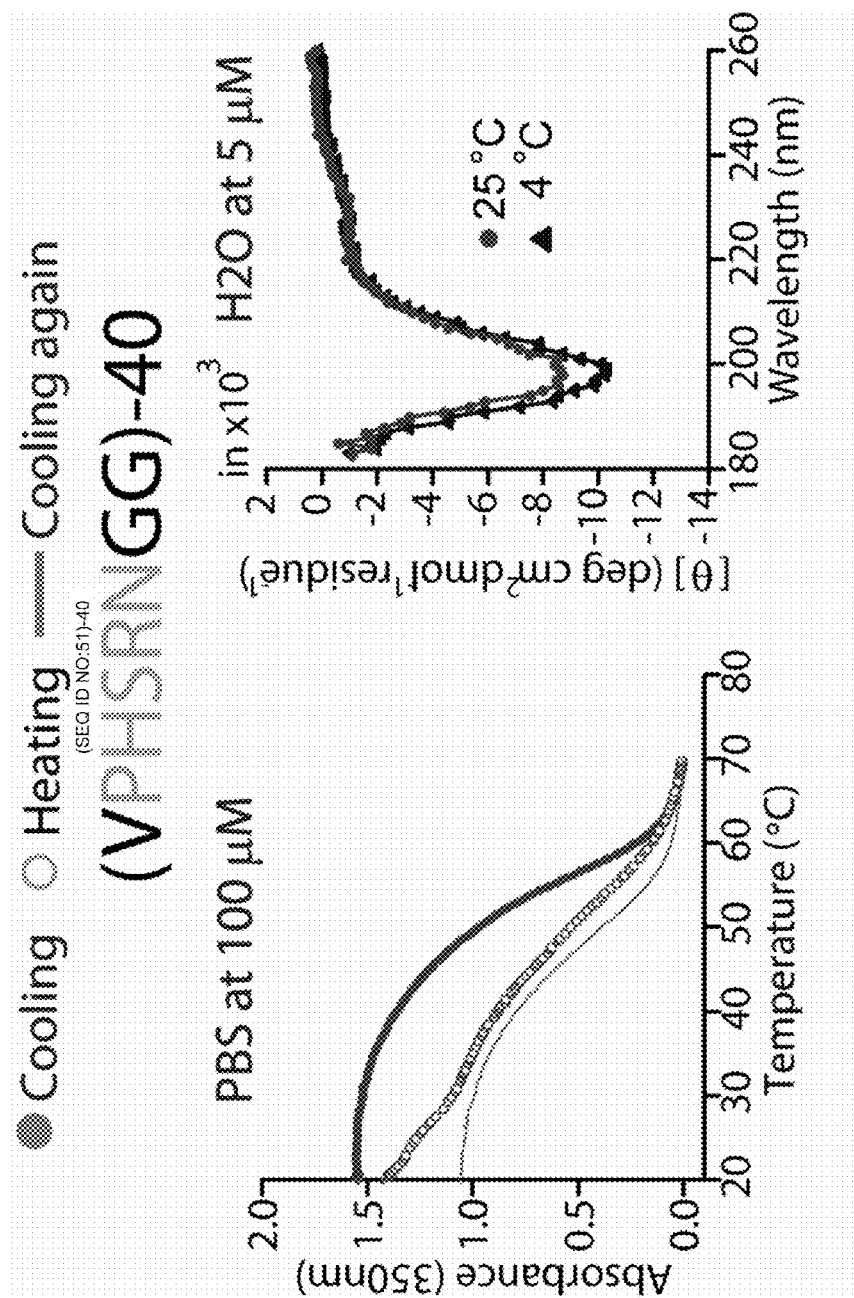

FIG. 36 is a graph showing that environmentally responsive polypeptides that contain the peptide drug PHSRN display UCST behavior.

Figure 37:
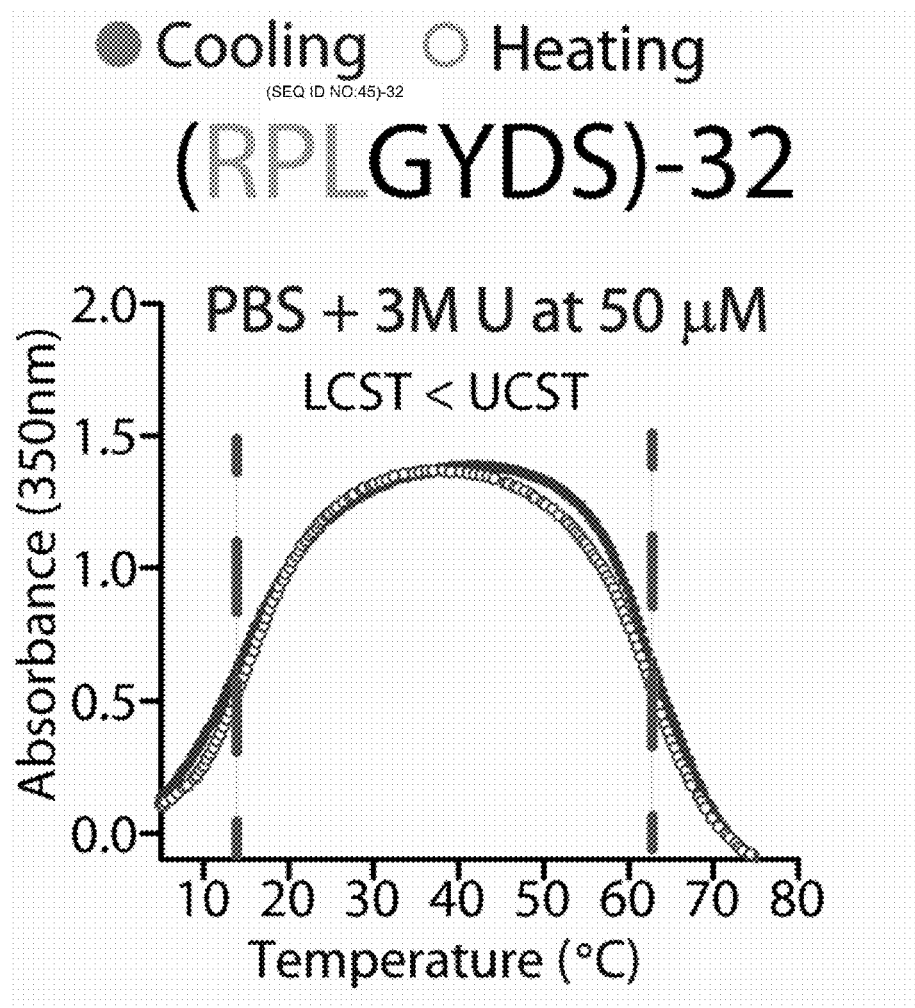

FIG. 37 is a graph showing that environmentally responsive polypeptides may be designed to display complex phase behaviors.

Figure 38:
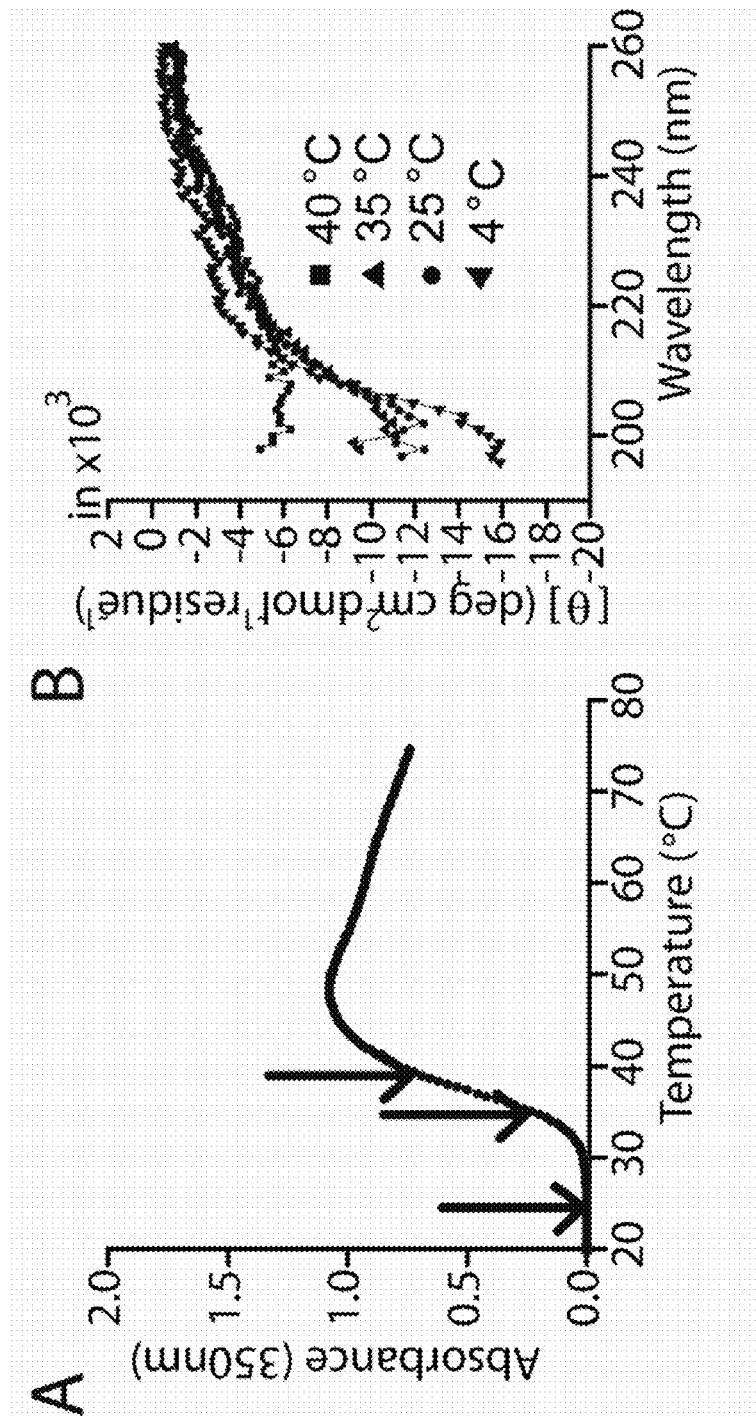

FIG. 38 is a graph showing that an environmentally responsive polypeptide based on the bioactive site of murine Endostatin displayed an inverse phase transition temperature reminiscent of other environmentally responsive polypeptides with simpler syntax. The phase transition of a 5 µM solution of mEndo1-6 in PBS (pH 6.4) (A) was accompanied by a decrease in the disorder of the polypeptide conformation (B), as measured by circular dichroism under identical conditions as in (A).

DETAILED DESCRIPTION

The present disclosure describes a model for the design of elastomeric and non-elastomeric protein-polymers and polypeptides which are environmentally responsive, by introducing repeats of functional motifs of the form $Z_1Z_2PXGZ_3$ (SEQ ID NO: 22) or $Z_1Z_2PXGZ_3Z_4$ (SEQ ID NO: 22), wherein in each case P is Proline, G is Glycine, X is from 1 to 4 amino acids that are not Proline or Glycine, and $Z_1$, $Z_2$, $Z_3$ and $Z_4$ are any amino acid. In certain embodiments, $Z_1$, $Z_2$, $Z_3$ and $Z_4$ do not generate a PG (proline-glycine) motif. The present disclosure also describes environmentally responsive polypeptides which include ten or more sequences selected from VGAPVG (SEQ ID NO: 24), LGAPVG (SEQ ID NO: 25), VPSALYGVG (SEQ ID NO: 26), VGPAVG (SEQ ID NO: 27), VTPAVG (SEQ ID NO: 28), VPSDDYGQG (SEQ ID NO: 29), VPSDDYGVG (SEQ ID NO: 30), TPVAVG (SEQ ID NO: 31), VPSTDYGVG (SEQ ID NO: 32), VPAGVG (SEQ ID NO: 33), VPTGVG (SEQ ID NO: 34), VPAGLG (SEQ ID NO: 35), VPHVG (SEQ ID NO: 36), VHPGVG (SEQ ID NO: 37), VPGAVG (SEQ ID NO: 38), VPGVAG (SEQ ID NO: 39), VRPVG (SEQ ID NO: 40), GRGDSPY (SEQ ID NO: 41), GRGDSPH (SEQ ID NO: 42), GRGDSPV (SEQ ID NO: 43), GRGDSPYG (SEQ ID NO: 44), RPLGYDS (SEQ ID NO: 45), RPAGYDS (SEQ ID NO: 46), GRGDSYP (SEQ ID NO: 47), GRGDSPYQ (SEQ ID NO: 48), GRGNSPYG (SEQ ID NO: 49), GRGDAPYQ (SEQ ID NO: 50), VPHSRNGG (SEQ ID NO: 51), VPHSRNGL (SEQ ID NO: 52), VPGHSHRDFQPVLHLVALNSPLSGGMRG (SEQ ID NO: 53), HTHQDFQPVLHLVALNTPLSGGMRGIRPGG (SEQ ID NO: 54), FEWTPGWYQPYG (SEQ ID NO: 55), or any combination thereof.

Environmentally responsive polypeptides including the motif $(Z_1Z_2PGZ_3G)_n$ (SEQ ID NO: 56)$_n$ may also be formed, where $Z_1$, $Z_2$ and $Z_3$ are any amino acid. These polypeptides may be bioactive, elastic or a combination thereof. This motif, when repeated consecutively, includes the bioactive motif GXXPG (SEQ ID NO: 21) responsible for elastin's ability to control various physiological processes including inflammation, chemotaxis, cell proliferation and differentiation, extracellular matrix remodeling and the like. Polypeptides containing the motif $(Z_1Z_2PGZ_3G)_n$ (SEQ ID NO: 56)$_n$ may be elastic and environmentally responsive and provide a bioactive signal when used to form recombinant elastin-like materials.

Also described are polypeptides in which the cell adhesion peptide GRGDSP is modified to conform to a $P(X_n)G$ motif. The phase transition temperature of a polypeptide containing such a motif may be controlled by adding or modifying residues incorporated into the motif, such that the original cell adhesion signal is modulated to signal, for example, exclusively through integrins or through both integrins and the elastin-binding receptor. Examples of such polypeptides include those containing the octapeptides $(GRGDSPZG)_n$ ((SEQ ID NO: 57)$_n$) and $(GRGDSPGZ)_n$ ((SEQ ID NO: 58)$_n$), and FEWTPGWYQPY (SEQ ID NO: 59). Environmentally responsive polypeptides may include one or more of a PG motif, $PX_1G$ motif (where $X_1$ is an amino acid), or combination thereof.

The protein polymers produced are environmentally responsive, and may be elastomeric or non-elastomeric. The present disclosure demonstrates minima functional motifs that confer environmental responsiveness to polypeptides thereof. The environmental sensitivity may be tuned by varying polypeptide molecular weight, polypeptide concentration, buffer ionic strength, hydrophobicity of amino acids in non-essential positions within the motif, the number of residues separating Pro and Gly, and the precise localization of additional Gly residues which may surround the $P(X_n)G$ unit. Polypeptides incorporating the motifs may be elastomeric or non-elastomeric protein-polymers, and may display reversible inverse phase transition behavior and/or heat-irreversible inverse phase transition above a critical temperature, typically higher than body temperature.

Environmentally responsive refers to the property of a given polypeptide to undergo conformational changes, such as coacervation or aggregation, in response to an external stimulus. Aggregation may be reversible or irreversible. The environmentally responsive polypeptide may respond to a small change in stimulus with a pronounced physical change in one or more properties, such as a sharp change in solubility. Without limiting the scope of this disclosure, examples of stimuli include changes in temperature, pH, chemicals, electric field, and buffer ionic strength.

Polypeptides described herein may undergo a reversible phase transition or an irreversible soluble-to-insoluble phase transition in aqueous solution upon heating through a characteristic transition temperature (lower critical phase transition or LCST). If reversible, the transition temperature at which the polypeptide resolubilizes and transitions from insoluble-to-soluble may be the same as, or different from the soluble-to-insoluble phase transition temperature. Polypeptides may exhibit phase separation when exposed to a threshold temperature that is above a lower critical solution temperature (LCST) of the polypeptide, or may exhibit phase separation when exposed to temperatures below an upper critical solution temperature (UCST) of the polypeptide. Polypeptides described herein may also exhibit phase separation when exposed to threshold temperatures both above the lower critical solution temperature (LCST) and below the upper critical solution temperature (UCST). Phase separation may reversible or irreversible. In certain embodiments, a polypeptide may exhibit a reversible phase separation in response to a one stimulus and an irreversible phase separation in response to a different stimulus. The different stimulus may be different in type or degree.

The difference between the two transition temperatures may be at least about 1° C., at least about 2° C., at least about 3° C., at least about 4° C., at least about 5° C., at least about 6° C., at least about 7° C., at least about 8° C., at least about 9° C., at least about 10° C., at least about 12° C., or at least about 15° C. The resolubilization transition temperature may be higher or lower than the soluble-to-insoluble phase transition temperature. The polypeptides may undergo inverse temperature transition, becoming more ordered as the temperature increases.

The compositions and polypeptides described herein display a surprising environmentally responsive profile. For example, it has been alleged that the pentapeptide motif VPXVG displays inverse temperature transition only if X=A, where A is Alanine (see, e.g., Bessa, P. C. et al. (2010; J Control Release. 142(3):312-8). The inventors surprisingly found that this was not the case. The present disclosure introduces functional motifs that facilitate formation of stable, ordered, secondary structures in a given dynamic range of stimuli sensed by the polypeptides (e.g., below the LCST of a polypeptide, or the UCST of a polypeptide). Furthermore, the present disclosure describes elastomeric and/or environmentally responsive polypeptides which are protein polymers containing pentapeptide, hexapeptide, septaheptide, octapeptide, nonapeptide motifs, or a combination thereof. The motifs may be at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, or at least 150 amino acids in length. Suitable amino acids include naturally occurring amino acids, D-amino acids, L-amino acids, and synthesized amino acids, such as unnatural amino acids. Table 1 displays the transition behavior of certain exemplary motifs disclosed herein, with respect to displaying UCST, LCST or both.

TABLE 1

LCST and USCT Behavior of Exemplary Polypeptide Motifs

| Sequence Motifs | Transition Behavior |
|---|---|
| VAPVG (SEQ ID NO: 27) | LCST |
| VGAPVG (SEQ ID NO: 24) | LCST |
| LGAPVG (SEQ ID NO: 25) | |
| VPSALYGVG (SEQ ID NO: 26) | LCST |
| VGPAVG (SEQ ID NO: 17) | LCST |
| VTPAVG (SEQ ID NO: 18) | LCST |
| TVPGAG (SEQ ID NO: 71) | LCST |
| AVPGVG (SEQ ID NO: 8) | |
| TVPGVG (SEQ ID NO: 70) | |
| AVPGVGAVPGVGAVPGVGAVPGVGAVPGVGCVPGVG (SEQ ID NO: 64) | |
| GAPFGFAIPMGAGFPTGGLAPFGMGLPAGM (SEQ ID NO: 12) | LCST |
| VPSDDYGQG (SEQ ID NO: 29) | LCST and UCST |
| VPSDDYGVG (SEQ ID NO: 30) | LCST |
| TPVAVG (SEQ ID NO: 31) | LCST |
| VPSTDYGVG (SEQ ID NO: 32) | LCST |
| VPAGVG (SEQ ID NO: 33) | LCST (for each) |
| VPTGVG (SEQ ID NO: 34) | |
| VPAGLG (SEQ ID NO: 35) | |
| VPAGVGVPAGVGVPAGVGVPAGVGVPAGVGVPCGVG (SEQ ID NO: 65) | |
| GVPAGHRYPIGGGQPHGKGCPDGVFRPVGLGAPYGHGAPNGMHRPLGIGKPRGHMYPKGQGQPMGHLVPDGVGFPRGRKKPVGVGKPIGNGHPIGARTPLGYGMPDGVGMPMGLFLPNGHGAPHGQGYPAGKLIPKGKGHPFGKGRPLGAGRPTGFKMPKGLGKPMGVGQPQGHFVPFGLGQPTGQGAPRGGSQPAGLGHPLGAGAPAGRCHPYGMGVPRGLAMPRGHGQPRGVGYPKGH (positions 5-244 of SEQ ID NO: 105) | |
| GVGPAGHRYPIGGQPHGKCGPDGVFRPVGLAGPYGHAGPNGMHRPLGIKGPRGHMYPKGQQGPMGHLVPDGVGFPRGRKKPVGVGKPIGNHGPIGARTPLGYMGPDGVMGPMGLFLPNGHAGPHGQYGPAGKLIPKGKHGPFGKRGPLGARGPTGFKMPKGLKGPMGVQGPQGHFVPFGLQGPTGQAGPRGGSQPAGLHGPLGAAGPAGRCHPYGMVGPRGLAMPRGHQGPRGVYGPKGH (SEQ ID NO: 110) | |
| VPHVG (SEQ ID NO: 36) | LCST |
| VHPGVG (SEQ ID NO: 37) | LCST |
| VPGAVG (SEQ ID NO: 38) | LCST |
| VPGVAG (SEQ ID NO: 39) | LCST |

TABLE 1-continued

LCST and USCT Behavior of Exemplary Polypeptide Motifs

| Sequence Motifs | Transition Behavior |
|---|---|
| APGVG (SEQ ID NO: 99) | LCST |
| VPGVA (SEQ ID NO: 111) | LCST |
| VRPVG (SEQ ID NO: 40) | LCST |
| GRGDSPY (SEQ ID NO: 41) | UCST (for each) |
| GRGDSPH (SEQ ID NO: 42) | |
| GRGDSPV (SEQ ID NO: 43) | |
| GRGDSPYG (SEQ ID NO: 44) | UCST |
| RPLGYDS (SEQ ID NO: 45) | UCST and LCST (for each) |
| RPAGYDS (SEQ ID NO: 46) | |
| GRGDSYP (SEQ ID NO: 47) | UCST |
| GRGDSPYQ (SEQ ID NO: 48) | UCST |
| GRGNSPYG (SEQ ID NO: 27) | UCST |
| GRGDAPYQ (SEQ ID NO: 49) | UCST (predicted) |
| VPHSRNGG (SEQ ID NO: 51) | UCST |
| VPHSRNGL (SEQ ID NO: 52) | |
| VPGHSHRDFQPVLHLVALNSPLSGGMRG (SEQ ID NO: 53) | LCST |
| HTHQDFQPVLHLVALNTPLSGGMRGIRPGG (SEQ ID NO: 54) | LCST |

The polypeptides may include a combination of LCST and UCST motifs which may convey both UCST and LCST transition behavior to the polypeptide. The LCST and UCST motifs may be interspersed in the polypeptide. For example, the LCST and USCT motifs may be randomly distributed in the polypeptide, may alternate with each other, may be consecutive, or may include spacer sequences between them, or any possible combination thereof.

The polypeptides may include at least about 5, at least about 10, at least about 11, at least about 12, at least about 13, at least about 14, at least about 15, at least about 16, at least about 17, at least about 18, at least about 19, at least about 20, or at least about 25 of the motifs described herein and less than about 1000, less than about 500, less than about 400, less than about 300, less than about 275, less than about 250, less than about 225, less than about 200, less than about 150, less than about 100, less than about 75, less than about 50, or less than about 30 of the motifs described herein. The polypeptides may include only one repeated motif, or may include a number of different motifs, as set forth above, which may or may not be repeated. Polypeptides may be formed which are homopolymers of the repeating units, or heteropolymers, including alternating copolymers, periodic copolymers, block copolymers, and statistical copolymers. Block polymers may include diblocks or triblocks of the motifs described herein.

The motifs may be consecutive within the polypeptide, may be separated by one or more spacer sequences, or a combination thereof. The spacer sequences may include at least 1, at least 2, least 3, at least 4, least 5, at least 6, least 7, at least 8, least 9, at least 10, least 11, at least 12, least 13, at least 14, least 15, at least 16, at least 17, at least 18, least 19, at least 20, at least 21, at least 22, least 23, at least 24, least 25, at least 26, at least 27, at least 28, at least 29, at least 30, at least 35, at least 40, at least 45, at least 50, at least 60, at least 70, at least 80, at least 90, at least 100, at least 150, at least 200, at least 250, or at least 300 amino acids.

Polypeptides may also be retro-polypeptides, including the polypeptides or one or more of the motifs disclosed herein as a reverse sequence reading from the C-terminus to the N-terminus, rather than the N-terminus to the C-terminus.

The present disclosure facilitates the design of biologically inspired polypeptides based on the identification and reverse engineering of minima functional motifs found in natural repetitive proteins, which confer a variety of structural or functional properties. The present inventors discovered that amino acid sequences seen to recur in natural repetitive proteins occur as a subspace of particular sequences, which have been selected through evolution, within a larger space of sequences displaying similar properties.

The compositions disclosed herein can be used as materials for a variety of biomedical and biotechnological applications, including, without limitation, those pertaining to the uses of elastin-derived biomaterials, silk-like biomaterials, resilin-like biomaterials and elastin-like biomaterials (see, e.g., U.S. Pat. No. 7,429,458; U.S. Pat. No. 6,852,834; U.S. Pat. No. 5,336,256; U.S. Patent Application No. 2010/0015070; U.S. Pat. No. 7,674,882; and U.S. Pat. No. 4,976,734, the disclosures of each of which are herein incorporated by reference in their entireties).

Amino acid motifs and polypeptides disclosed herein may be used in the design and synthesis of elastomeric-inspired polypeptides, which may be engineered to confer or possess environmental sensitivity and/or elasticity to protein-polymers, while maintaining sequence diversity. A variety of useful properties and applications are envisaged, including those presented below.

The functional motifs described are sufficiently flexible to be incorporated directly into bioactive polypeptides to confer environmental sensitivity and elasticity to such polypeptides. For example, the present disclosure makes it possible to transform a protein bioactive peptide signal (e.g., cell adhesion peptides, integrin inhibitors, anti-inflammation peptides, cell differentiation, proliferation, angiogenic and anti-angiogentic signals, etc.) into an environmentally responsive polypeptide capable of acting as a "smart" drug that is environmentally responsive.

Functional motifs may also be included in combination with one or more other drugs or therapeutics transported as part of an engineered self-assembled therapeutic delivery vehicle wherein the vehicle itself may constitute an environmentally responsive polypeptide based biodrug. The polypeptide may become bioactive after undergoing a conformational change at the biological target site. Functional motifs may also be included or introduced into a scaffolding material wherein the functional motifs carry biochemical cues for controlling cell-cell and cell-surface interactions, inflammation, chemotaxis or any other relevant biological process.

Environmentally responsive, bioactive polypeptides, may be used as integrin inhibitors for anti-angiogenic therapy or as active pro-angiogenic materials for tissue engineering applications. The sequence diversity of the polypeptides described herein may be exploited because different integrins recognize alternative peptide sequences. For example, a4131 can recognize EILDV (SEQ ID NO: 60) and REDV (SEQ ID NO:

61). Polypeptides described herein having an unordered structure are suitable for displaying these signals. Anti-inflammatory environmentally responsive polypeptides may include one or more of a PG motif, $PX_1G$ motif, or combination thereof. The motif may be an anti-inflammatory peptide, such as FEWTPGWYQPY (SEQ ID NO: 59) and modifications thereof, that prevent scaffold immunorejection.

The polypeptides described herein display similar elasticity and environmental sensitivity to other elastin-like polypeptides (ELPs), and may be utilized in applications which exploit the properties of ELPs. The use of the motifs described herein allows for control of the hydrophobicity profile of the polypeptides or blocks within block-copolymer polypeptides, by substituting a variety of residues in any of the positions available for substitution within the functional motif. Polypeptides may thus be designed, for example, to self-assemble into more complex and/or defined structures, to gain control on the elastic force (correlated with Pro content and hydrophobicity), or to improve the environmental sensitivity of tags for protein purification.

Polypeptides described herein may also be used in drug and therapeutic delivery applications for treating patients suffering from a disease or condition. Such vehicle delivery applications may include the formation of nanoparticles from environmentally responsive polypeptides and their delivery to a biological site such as an organ, tissue, tumor, wound site or disease site. The tumor, wound or disease site may be localized or systemic in a patient. Targeted delivery may be achieved by recognition, binding or affinity of a particular receptor or other molecule that is associated with the tumor, wound or disease by the nanoparticle. The nanoparticles may self-assemble around a therapeutic. The therapeutic may be hydrophobic or hydrophilic. For example, drug and therapeutic delivery vehicles comprising polypeptides described herein that respond to a pH stimulus or temperature change at the microenvironment of the biological site, may be triggered to release a chemotherapeutic cargo in the biological site. The ability to fine tune the pH responsiveness of drug and therapeutic delivery vehicles may be achieved by selecting a polypeptide having amino acid residues in the motifs which have appropriate pKa values, such that they change their ionization state at relevant pH values.

Polypeptides described herein may be bioactive, or may lose bioactivity or become bioactive after delivery to a biological site. Bioactive refers to the ability to have biological activity at a biological site, and may include the ability to induce biological effects, therapeutic activity, or a combination thereof.

Fusion proteins may be formed which include an environmentally responsive polypeptide operably connected to a polypeptide of interest. Fusion proteins may be generated by generating a polynucleotide which includes a polynucleotide encoding an environmentally responsive polypeptide operably connected to a polynucleotide encoding a polypeptide of interest and expressing a polypeptide from the polynucleotides. The expressed polypeptide contains the environmentally responsive polypeptide connected or fused to the polypeptide of interest. Optionally a linker sequence may be included between the polynucleotides and fused polypeptides. The linker sequence may be at least 1, least 2, least 3, least 4, least 5, least 6, least 7, least 8, least 9, least 10, least 15 amino acids and less than 200, 150, 100, 75, 50, 40, 30 or 20 amino acids. Expression may be carried out, for example in a bacterial, yeast or mammalian cell, with the appropriate promoter sequence. Fusion proteins may also be generated by chemical synthesis, or by chemically attaching naturally or chemically synthesized peptides and polypeptides together.

The environmentally sensitive polypeptide may also be chemically conjugated to molecules such as therapeutics, carbohydrates, synthetic polymers, polynucleotides and oligonucleotides, including DNA, RNA, as well chemically synthesized small molecules.

The present disclosure is not limited in its application to the details of construction and the arrangement of components set forth in the following description or illustrated in the drawings. The invention described in the present disclosure is capable of other embodiments and of being practiced or of being carried out in various ways. Also, the phraseology and terminology used herein is for the purpose of description and should not be regarded as limiting.

The use of "including," "comprising," "having," "containing," "involving," and variations thereof herein, is meant to encompass the items listed thereafter and equivalents thereof as well as additional items. For the purposes of promoting an understanding of the principles of the present disclosure, reference will now be made to preferred embodiments and specific language will be used to describe the same.

The articles "a" and "an" are used herein to refer to one or to more than one (i.e. at least one) of the grammatical object of the article. By way of example, "an element" means at least one element and can include more than one element.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, and in some embodiments ±0.1% from the specified amount, as such variations are appropriate to perform the disclosed methods.

EXAMPLES

Materials and Methods

Gene Synthesis of EIPs:

EIPs can be synthesized by standard molecular biology techniques suitable for the synthesis of genes encoding repetitive protein-polymers, some of which have been previously described (see, e.g., McDaniel, J. R. et al. (2010) *Biomacromolecules* 10.1021/bm901387t; Meyer, D. E. et al. (2002) *Biomacromolecules* 3:357-367). Many of the EIP genes herein reported were synthesized by a novel method recently developed by the inventors, which are described elsewhere herein. Regardless of the gene synthesis method used for their construction, the DNA sequence of all of the genes encoding EIP protein-polymers characterized herein were verified by direct DNA sequencing (Eton Bioscience Inc., NC, USA). Before expression, an N-terminal leader sequence encoding for Met-Ser-Lys-Gly-Pro (SEQ ID NO: 62) and a C-terminal His-tag tail encoding for His-His-His-His-His-His-Y (SEQ ID NO: 63) were incorporated into the genes, unless indicated. The properties of the compositions subject to the present disclosure are independent of the aforementioned leader and trailer sequences; however, the incorporation of a His-tag sequence typically results in a significant increase in the transition temperature of polypeptides, particularly those of low molecular weight (e.g., <20 KDa).

Expression and Characterization of EIPs:

Before large-scale expression, starter cultures (3-5 mL) of TB media supplemented with 100 µg/mL ampicillin were inoculated with transformed cells from DMSO stocks stored at −80° C., and incubated overnight at 37° C. while shaking at 250 rpm. The starter cultures were then centrifuged at 3000 g for 2 min, and resuspended in 1 mL of fresh TB medium.

Expression cultures (4 L flasks containing 1 L of TB media with 100 μg/mL ampicillin) were inoculated with the resuspended starter culture and incubated at 37° C. with shaking at 200 rpm. After 6-7 h of growth, expression was induced by the addition of IPTG to a final concentration of 1 mM. The cells were harvested 24 h after inoculation, and purified by inverse transition cycling (ITC) as previously described, or, in a limited number of cases, by His-tag purification following the instructions of the manufacturer (Pierce, USA) (see, e.g., Christensen, T. et al. (2009) *Protein Science* 18:1377-1387). To characterize the inverse transition temperature of EIPs, the optical density of EIP solutions (25-50 μM), prepared in PBS or PBS supplemented with NaCl and/or 8M Urea as indicated, was monitored at a wavelength of 350 nm ($OD_{350}$) as a function of temperature, at a heating rate of 1° C. $min^{-1}$, on a Cary 300 UV-visible spectrophotometer equipped with a multicell thermoelectric temperature controller (Varian Instruments, Walnut Creek, Calif.). The derivative of the optical density with respect to temperature was numerically calculated, and the Tt was defined as the temperature at the maximum of the turbidity gradient.

Bioinformatics Studies:

The amino acid sequence of different elastomeric and non-elastomeric proteins was retrieved as FASTA (.txt) filed from the National Center for Biotechnology Information protein database. In-house custom methods were implemented in MATLAB software (MathWorks, Natick, Mass.) to map the location of elastin-like polypeptide motifs (e.g., VPGXG (SEQ ID NO: 3), IPGXG (SEQ ID NO: 5)) among the sequence of these proteins, the occurrence of generalized $P(X_n)G$ motifs (where n indicated the number of X residues separating a given Proline and Glycine residue, and varies as 1≤n≤5), the hydrophobicity profiles of amino acids associated with residues participating or surrounding these motifs, the distance between them, and the precise location of Glycine residues in relation to Glycine residues participating in $P(X_n)G$ motifs. Two different hydrophobicity scales were considered in these analyses, the scale proposed by Kyte and Doolittle and Urry et al. (see, e.g., Kyte, J. et al. (1982) *J. Mol. Biol.* 157:105-132; Urry D. W. (1992) supra).

TABLE 1

Sequence information of the different polypeptides used in the bioinformatics studies.

| Protein | Species | Accession Number (GI) |
|---|---|---|
| Elastin | Homo sapiens | 182021 |
| Elastin | Bos taurus | 28461173 |
| Elastin | Mus musculus | 31542606 |
| Elastin | Rattus norvegicus | 55715827 |
| Elastin | Macaca mulatta | 13182892 |
| Elastin b | Danio rerio (Zebrafish) | 114326248 |
| Elastin a | Danio rerio (Zebrafish) | 121583675 |
| Alpha-1 Collagen Type I | Homo sapiens | 553615 |
| Collagen Type III alpha 1 | Homo sapiens | 4502951 |
| Collagen Type II alpha 1 | Homo sapiens | 111118974 |
| Collagen Type X alpha 1 | Homo sapiens | 120659966 |
| Collagen Type VIII alpha 2 | Homo sapiens | 32964830 |
| Fibrillin 1 | Homo sapiens | 46559358 |
| Dragline silk fibroin (Spidroin 2) | Nephila clavipes | 159714 |
| flagelliform silk protein | Nephila clavipes | 2833649 |
| Fibulin 5 precursor | Homo sapiens | 19743803 |
| Fibrillin | Homo sapiens | 1335064 |
| Resilin Isoform B | Drosophila melanogaster | 45552671 |
| Resilin Isoform A | Drosophila melanogaster | 7302880 |
| High molecular weight gluten subunit | Elymus alashanicus | 84181091 |
| Titin | Homo sapiens | 1212992 |
| Fibroin-3 (ADF-3) | Araneus Diadematus | 1263287 |
| Protein PRQFV-amide | Aplysia californica | 74842069 |
| FMRFamide-related neuropeptides | Lymnaea stagnalis | 1169643 |
| Transcription elongation factor spt5 | Schizosaccharomyces pombe | 74581925 |

Gene Synthesis:

The phase transition biopolymers described in the present invention were synthesized by standard molecular biology techniques suitable for the synthesis and expression of genes encoding repetitive protein-polymers. The genes encoding for the biopolymers herein reported were synthesized by three different methods, described below.

1. All genes, unless indicated, were synthesized using OERCA. Briefly, single stranded DNA sequences were designed encoding for 1 to 5 copies of the amino acid motif of interest—depending on the motif length—, which were then circularized using a ligase. The circular DNA was amplified and extended using primers specific for the 5' and 3' ends of the linear DNA using a polymerase with strand displacement activity in a PCR-type reaction that resulted in gene polymerization by two means: first, by way of rolling circle amplification, and second, by overlap elongation of the extended genes that had rolled from the circle. This resulted in a library containing oligomers with various numbers of repeats of the starting monomer unit (that already included 1-5 copies of the motif of interest), which were blunt ligated into a modified pET25 vector and transformed into BL21 cells. Clones having genes of various sizes and that were inserted in the correct orientation were screened, by way of colony PCR and direct DNA sequencing (Eton Bioscience Inc., NC, USA). DMSO stocks of all clones that harbored one gene that encoded for any number of repeats of the motif of interest were prepared.

2. Genes encoding for biopolymers with repeat units longer than 50 amino acids and with randomized composition were purchased from Mr. Gene and cloned into a modified pET24 vector for expression in *E. coli*. We prepared DMSO stocks of the clones that harbored the gene of interest.

3. Genes encoding for biopolymers with the following motifs were synthesized by Pre-RDL as recently described by the inventors [McDaniel et al. 2010]: GRGDSPYQ (SEQ ID NO: 48), GRGNSPYG (SEQ ID NO: 49), LGAPVG (SEQ ID NO: 25), AVPGVGAVPGVGAVPGVGAVPGV-GAVPGVGCVPGVG (SEQ ID NO: 64), and VPAGVGVPAGVGVPAGVGVPAGVGVPAGVGVPCGVG (SEQ ID NO: 65). Briefly, we designed oligonucleotides for the sense and antisense strands of genes encoding for 1-5 copies of the motifs of interest, which annealed leaving a 3' GG overhang on the sense strand and a 3' CC overhang on the antisense stand to allow for concatemerization. The concatemers were ligated into a modified pET24 vector and transformed into *E. coli*, and the resulting colonies were screened by colony PCR and direct DNA sequencing (Eton Bioscience Inc., NC, USA). We prepared DMSO stocks of all clones that harbored one gene that encoded for any number of repeats of the motif of interest.

Before expression, an N-terminal leader sequence encoding for Met-Ser-Lys-Gly-Pro (SEQ ID NO: 62) and a C-terminal His-tag tail encoding for His-His-His-His-His-His-Y (SEQ ID NO: 63) were incorporated into the genes, except for the genes synthesized by (2) and (3), which lacked the His-tag sequence. The properties of the compositions subject of the present invention are independent of the aforementioned leader and trailer sequences; however, the incorporation of a His-tag sequence typically results in a significant increase in the transition temperature of polypeptides, particularly those of low molecular weight (e.g., <20 KDa).

Expression and Characterization of EIPs.

Before large-scale expression, starter cultures (3-5 mL) of TB media supplemented with 100 µg/mL ampicillin were inoculated with transformed cells from DMSO stocks stored at −80° C., and incubated overnight at 37° C. while shaking at 250 rpm. The starter cultures were then centrifuged at 3000 g for 2 min, and resuspended in 1 mL of fresh TB medium. Expression cultures (4 L flasks containing 1 L of TB media with 100 µg/mL ampicillin) were inoculated with the resuspended starter culture and incubated at 37° C. with shaking at 200 rpm. After 6-7 h of growth, expression was induced by the addition of IPTG to a final concentration of 1 mM. The cells were harvested 24 h after inoculation, and purified by inverse transition cycling (ITC) as previously described (Christensen et al. 2009). To characterize the inverse transition temperature of phase transition biopolymers, the optical density of biopolymer solutions (25-50 µM), prepared in PBS or PBS supplemented with NaCl and/or 1-8M Urea as indicated, was monitored at a wavelength of 350 nm (OD350) as a function of temperature, at a heating rate of 1° C. min-1, on a Cary 300 UV-visible spectrophotometer equipped with a multicell thermoelectric temperature controller (Varian Instruments, Walnut Creek, Calif.). The derivative of the optical density with respect to temperature was numerically calculated, and the Tt was defined as the temperature at the maximum of the turbidity gradient.

Bioinformatics Studies.

The amino acid sequence of different Pro- and Gly-rich proteins was retrieved as FASTA (.txt) files from the National Center for Biotechnology Information protein database. In-house custom methods were implemented in MATLAB software (MathWorks, Natick, Mass.) to map the location of elastin-like polypeptide motifs (e.g., VPGXG (SEQ ID NO: 3), IPGXG (SEQ ID NO: 5)) among the sequence of these proteins, the occurrence of generalized $P(X_n)G$ motifs (where n indicates the number of X resides separating a given Proline and Glycine reside, and varies as $1 \le n \le 5$), the hydrophobicity profiles of amino acids associated with residues participating or surrounding these motifs, the distance between them, and the precise location of Glycine residues in relation to Glycine residues participating in $P(X_n)G$ motifs. Two different hydrophobicity scales were considered in these analyses, the scale proposed by Kyte and Doolittle (1982) and the scale proposed by Urry et al. 1992.

Results

Figure 1:
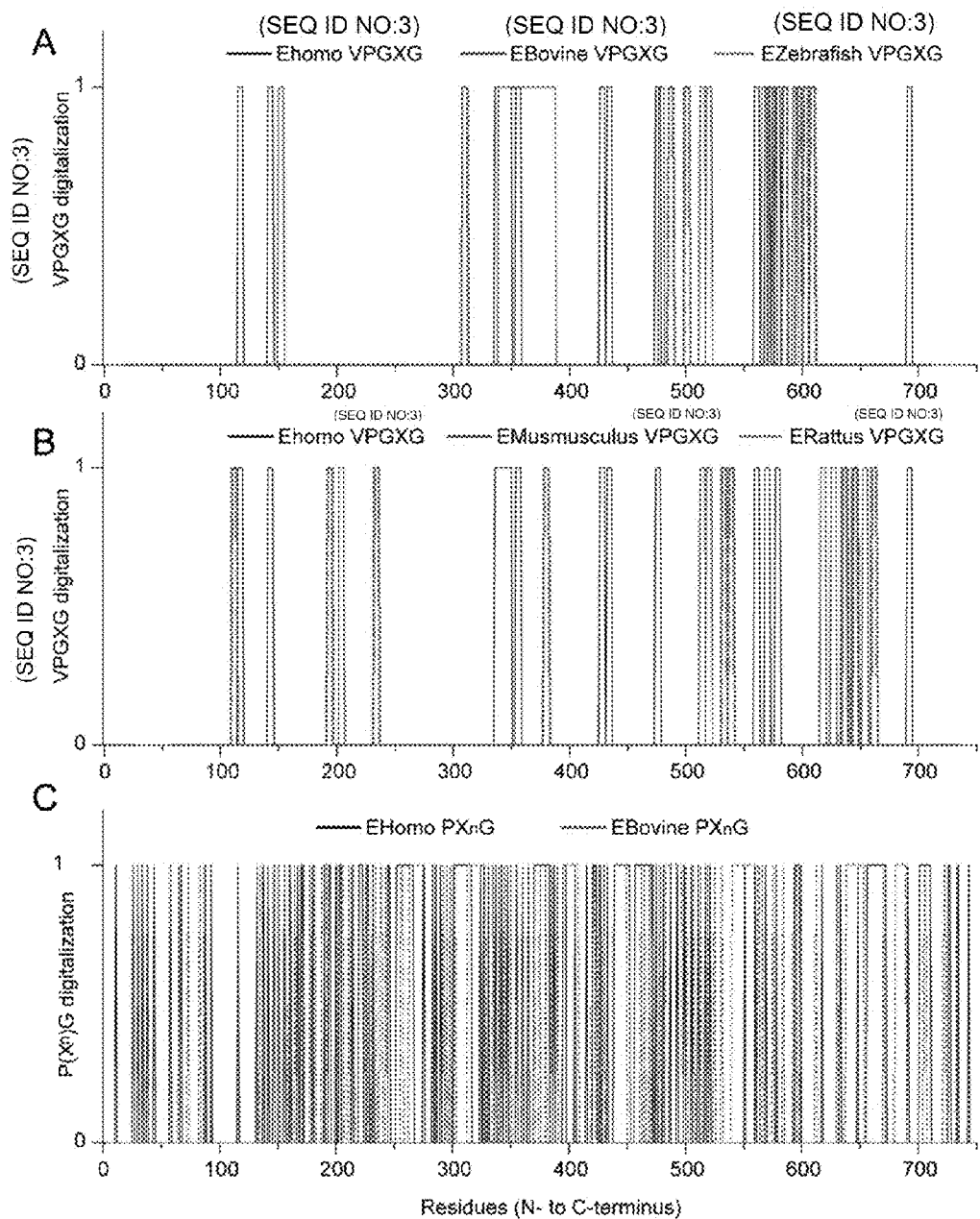
FIG. 1 depicts graphs showing the distribution of the VPGXG motif along the sequence of elastins from different species: *Homo sapiens*, Bovine, Zebrafish, *Mus musculus* and *Rattus* (FIGS. 1A and B); motifs such as VPGXG (SEQ ID NO: 3), LPGXG (SEQ ID NO: 4) and IPGXG (SEQ ID NO: 5) altogether account for only 10-20% of the amino acids in these sequences; sequence conservation among species is limited. Mapping of minima functional $P(X_n)G$ motifs along the sequences of Bovine and *Homo sapiens* elastin shows predominance of highly conserved PG motifs (i.e., sharp peaks) covering the entire sequence as evidenced by abundant overlapping peaks.
Figure 2:
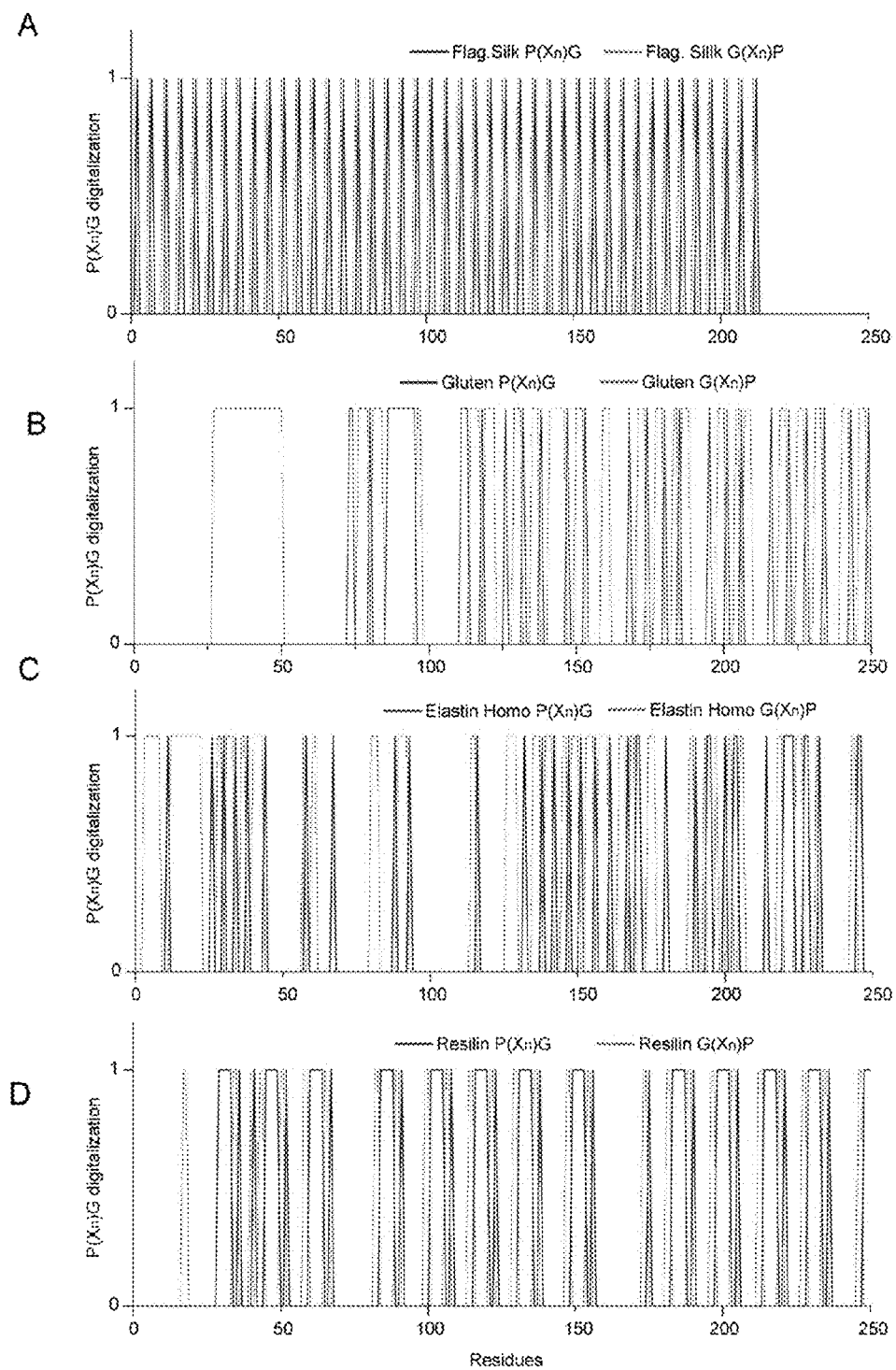
FIG. 2 depicts graphs showing the mapping of minima functional $P(X_n)G$ motifs and corresponding reversed $G(X_n)P$ motifs along the sequence (only shown for residues 0-250) of Flagelliform silk (A), elastin (B), gluten (C) and resilin (D). Similar analyses were performed for other proteins listed in Table 2. The directionality of the motif is evidenced for all proteins, except Flagelliform silk (and Dragline silk, not shown here), where GP and PG motifs (i.e., sharp red and blue peaks, respectively) show the same distribution as a result of the abundant GPGXX (SEQ ID NO: 7) motif, which displays both minima motifs. Increasing frequency of $P(X_n)G$ motifs with larger n values is observed when comparing the elastomeric proteins Flagelliform silk, gluten, elastin and resilin (FIG. 2 A-D).
Figure 3:
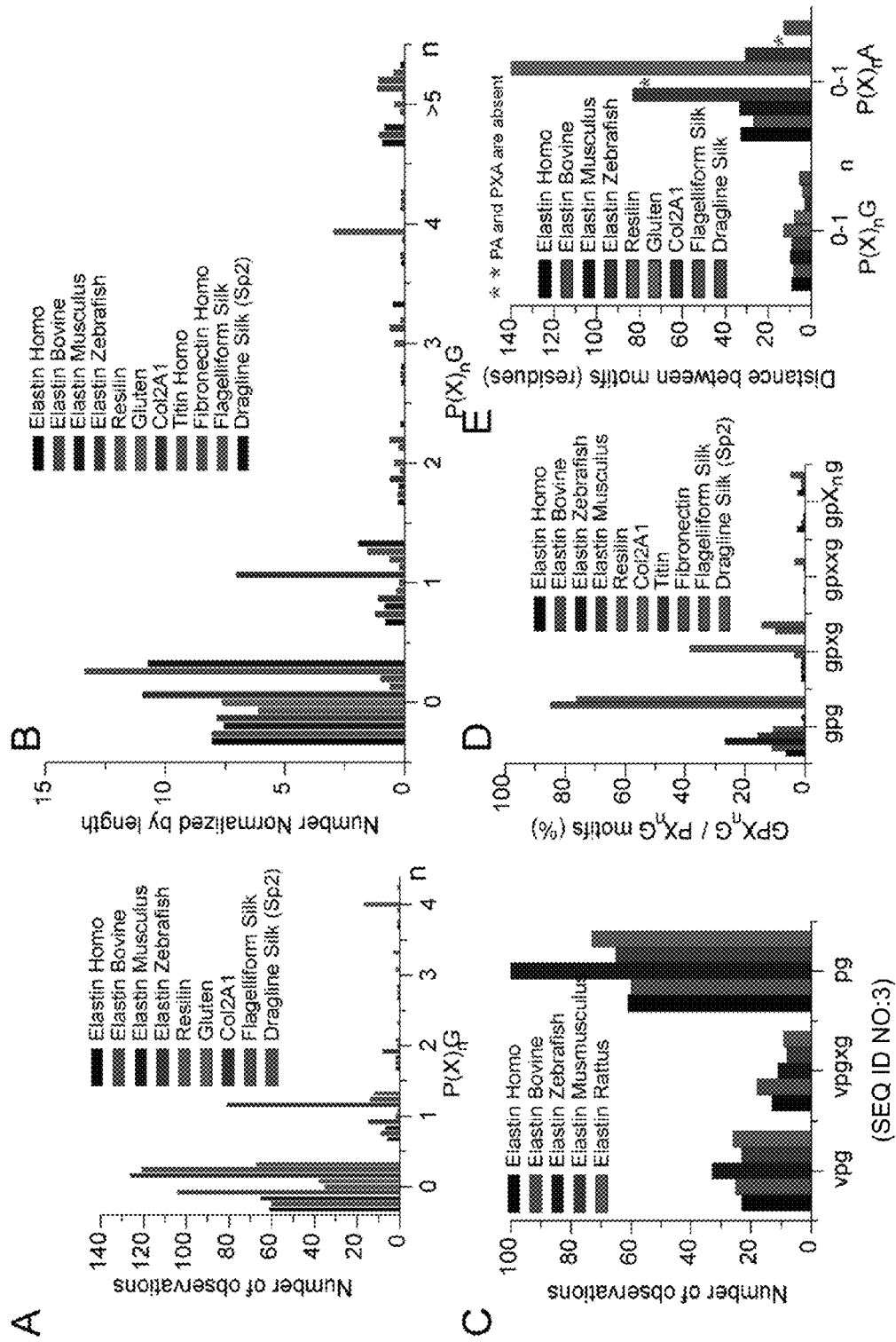
FIG. 3 depicts graphs showing quantitation of minima functional motifs among different elastomeric and non-elastomeric proteins. Occurrence of $P(X_n)G$ motifs before (A) and after (B) normalizing to the total length of the protein.

Simple bioinformatics methods were developed and implemented to visualize and quantify minima functional motifs in elastomeric proteins. FIG. 1 shows a digital map of the distribution and conservation of the canonical ELP motif VPGXG (SEQ ID NO: 3) along the sequence of elastin from various species. Relatively poor sequence conservation and low sequence coverage were observed. A minima functional $P(X_n)G$ motif was mapped, which encompasses multiple potential arrangement of Proline and Glycine residues, among elastin sequences. The results showed a surprisingly high degree of sequence conservation and sequence coverage, mostly corresponding to PG units (i.e., n=0) (FIG. 1C). A similar map was drawn from other elastomeric and non-elastomeric proteins where Proline and Glycine residues occur with high frequency. The occurrence of $P(X_n)G$ motifs other than the one observed in elastin sequences, particularly those where n=1 and n=4, were observed (see FIG. 2). Moreover, the distribution of these residues was random, as contrasting maps were observed for $P(X_n)G$ and $G(X_n)P$ motifs (see FIG. 2). These maps also uncovered a potential role for Gly residues closely positioned surrounding the $P(X_n)G$ motif, as observed when comparing the elastomeric flagelliform silk (FIG. 2A), where Gly usually occurs one residue before Proline, with elastin, gluten or resilin (FIG. 2B-D), where Gly occurs two or more positions before Proline. There was also evidence of a high abundance of a $PX_4G$ motif in resilin, but no evidence for $PX_2G$ and $PX_3G$ motifs was observed (see FIG. 3). Only silk proteins had a large percentage of $GPX_n$ motifs.

Figure 7:
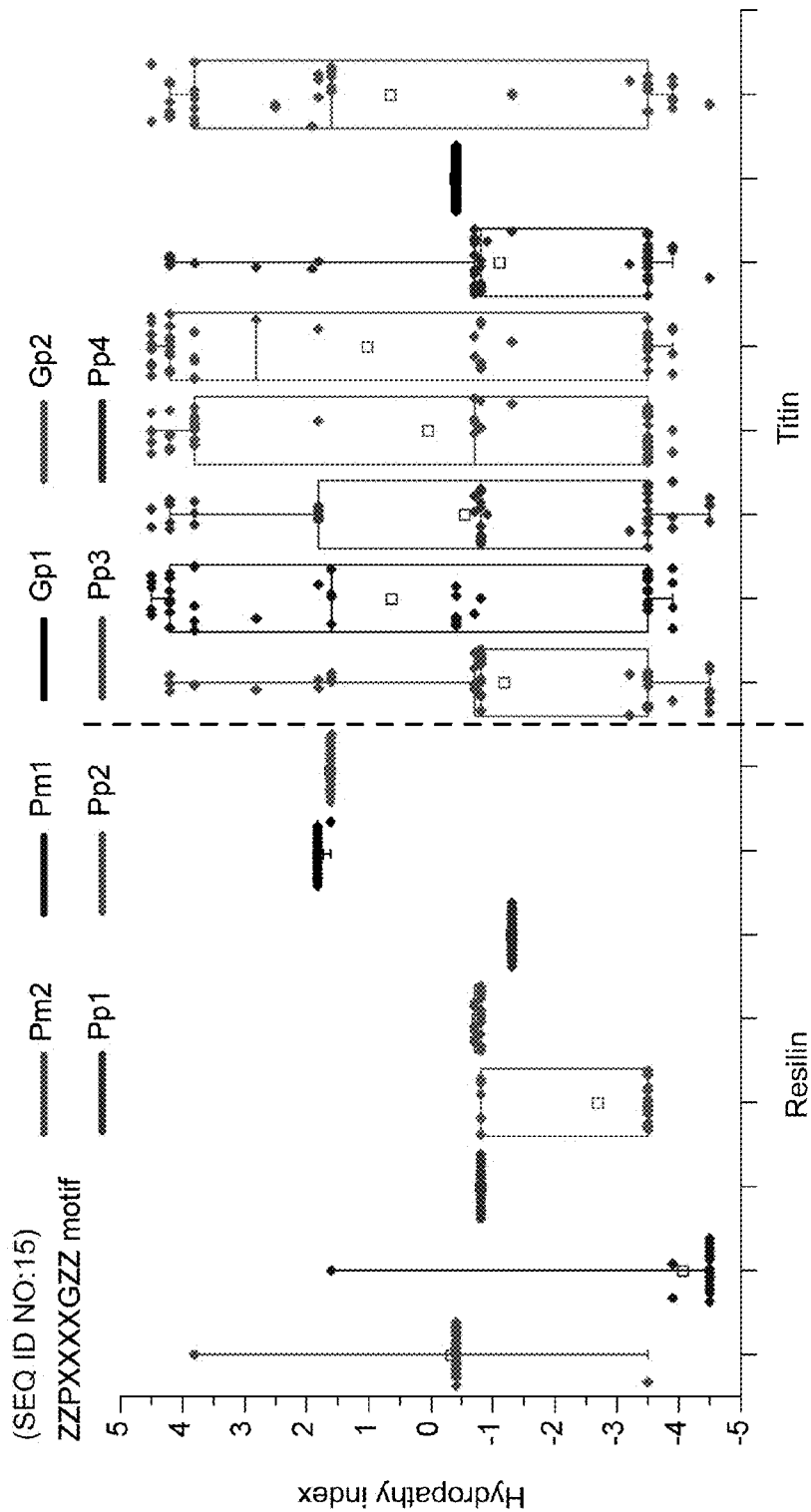
FIG. 7 is a graph showing hydropathy index (Hi) distribution for residues comprising and surrounding $P(X_n)G$ motifs (n=4) in resilin and titin. Whereas resilin shows a very tight Hi distribution in all positions comprising and surrounding the $P(X_4)G$ motif, accounting for 29.5% of the full protein sequence, the same motif accounts for only 1.6% of the amino acid sequence of titin, which was used for comparison due to its elasticity and remarkable length (26916 residues). Fibronectin and Col2A1 (*Homo sapiens*) have 0.12% and 0%, respectively. Titin shows a broad distribution of Hi indices, with the exception of Gp1 where only Gly occurs. In addition to Pm2, Pm1, Gp1 and Gp2, this analysis considers the residues Pp1 (for "Pro plus 1 position"), Pp2, Pp3, Pp4, which are equivalent to the 4× residues constituting the $P(X_n)G$ motif. The Hi was defined as proposed by Kyte and Doolittle (1982). The identity of the residues at a given position can be easily read from this figure (e.g., Glu=−0.4; Val=4.2; A=1.8, etc.). The box delineates the 25 and 95 percentile, and the men hydropathy is indicated by a square; raw data is also included for each residue position as filled diamonds.
Figure 8:
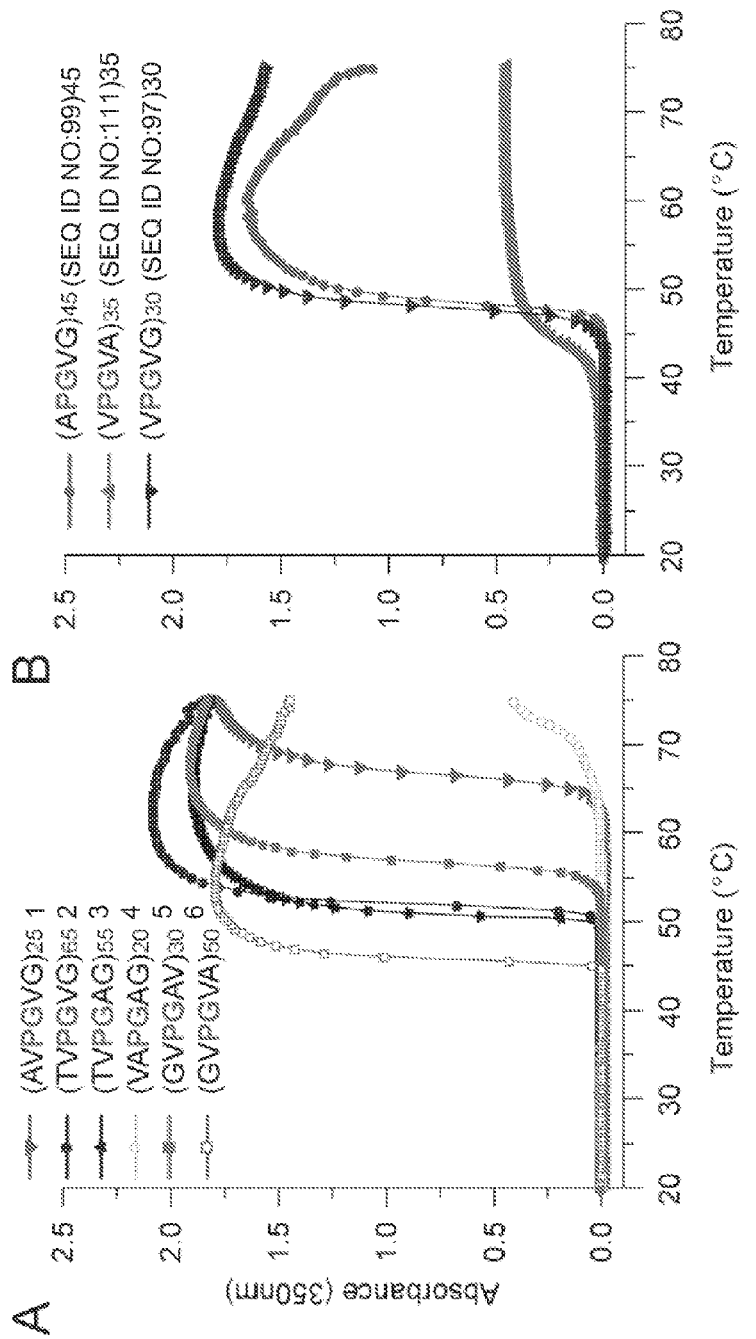
FIG. 8 depicts graphs showing environmental sensitivities of EIPs with $Z_1Z_2PGZ_3Z_4$ motif, exemplified for both hexapeptide (A) and pentapeptide (B) repeat units. This family of EIPs displays inverse phase transition behavior characterized by a sharp phase separation and self-assembly upon heating above the LCST or Tt of these polypeptides. The number of repeats in each protein-polymer is indicated in the legend. All samples were prepared at a concentration of 50 µM in PBS, with the exception of (APGVGP) and (TVPGAG) that were diluted in PBS supplemented with 2M NaCl, at 50 and 100 µM, respectively.
Figure 9:
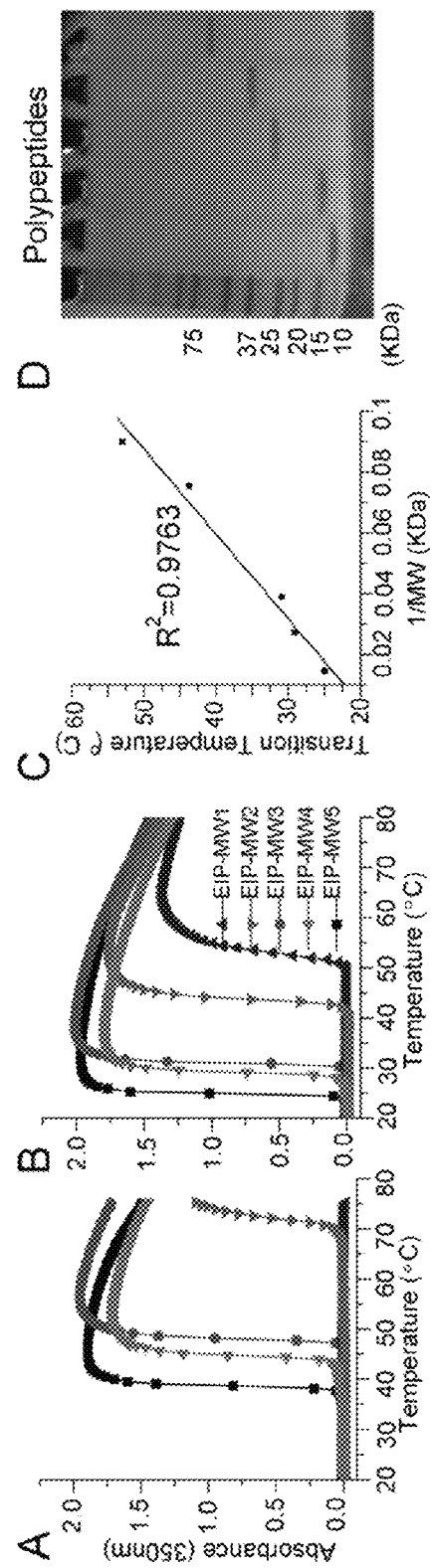
FIG. 9 depicts graphs and a photograph showing the characterization of a library of EIPs with the AVPGVG (SEQ ID NO: 8) repeat. Turbidity profiles for 5 constructs in this library at 25 µM in PBS (A) and PBS supplemented with 1M NaCl (B). The transition temperatures calculated from (B) varied linearly as the reciprocal of molecular weight of the EIP as expected for canonical ELP sequences (C). The distribution of molecular weights in this library is illustrated in (D), where EIP-MW1 corresponds to the lowest and EIP-MW5 to the highest molecular weight.
Figure 10:
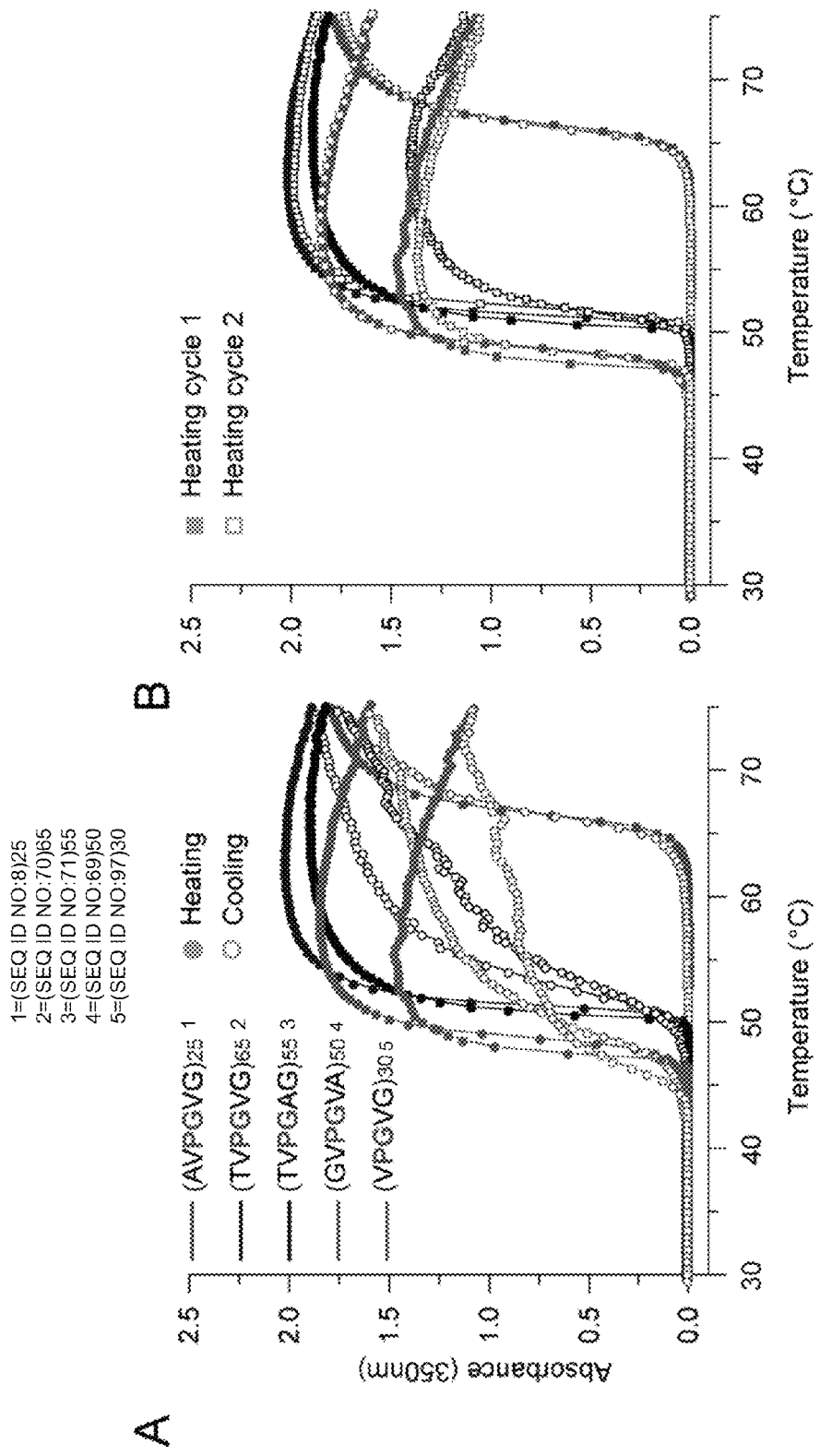
FIG. 10 depicts graphs showing reversible phase transition behavior displayed by EIPs with $Z_1Z_2PGZ_3Z_4$ (SEQ ID NO: 9) motif. This family of EIPs displays reversible inverse phase transition behavior characterized by a sharp phase separation and self-assembly upon heating above the LCST or Tt of these polypeptides, followed by disassembly upon lowering the temperature below the LCST (A). Furthermore, upon heating in a second heating cycle (B), these EIPs retain their environmental sensitivity. The number of repeats in each protein-polymer is indicated in the legend. All samples were prepared at a concentration of 50 µM in PBS, with the exception of (TVPGAG; SEQ ID NO: 10) that was diluted to 100 µM in PBS supplemented with 2M NaCl.

Elastomeric proteins display different properties and several mechanisms may be responsible for such differences; one such mechanism may relate to protein hydrophobicity. Elastomeric proteins, particularly elastin, may include an association of hydrophobic and hydrophilic (cross-linking) domains. A more detailed profiling of the hydrophobicity of key residues participating in the identified $PX_nG$ motifs was conducted. The hydrophobicity of these residues among elastin proteins, showed a distribution of hydropathy indices, which remained largely hydrophobic for bovine and *Homo sapiens*, but extended into more hydrophilic values for elastin proteins from Zebrafish and *Mus musculus* (see FIG. 4). Different evolutionary constraints experienced by these species may have resulted in the selection of amino acids covering various regions of a space of sequences all ascribing to a general $PX_nG$ motif. Evolutionary bias toward the localization of Gly residues two positions before the Pro (Pm2; Proline minus 2 residues) and one (Gp1; Gly plus 2 residues) or two (Gp2; Gly plus 2 residues) positions after the Gly in the $PX_nG$ motif was observed, along with a very low frequency of Gly residues occurring one position before the Pro (Pm1; Proline minus 1 residue). The abundant $PX_1G$ motif in collagen (FIG. 3B), however, occurs almost entirely with Gly at Pm1, with no other position surrounding the motif being biased toward any particular residue or hydropathy (see FIG. 5). Similar analyses were performed on a larger pool of elastomeric proteins and amino acids covering a broader range of hydropathy indices were explored; a similar bias in the distribution of Gly residues was found. For instance, resilin and gluten $PX_0G$ motifs are surrounded primarily by hydrophilic residues, such that the selection of hydrophobic amino acids in these positions may not be a prerequisite for the elastic behavior of these proteins. Similarly, the overall hydropathy of Dragline silk and Flagelliform silk are almost identical, being −0.40 and 0.37 (Kyte-Doolittle scale), respectively. The hydrophobicity of the residues surrounding the abundant $PX_0G$ motif in Dragline silk and Flagelliform silk (i.e., Pm2, Pm1, Gp1 and Gp2 in FIG. 5) show an average hydropathy for the neighboring residues of −0.16 and −1.2, respectively. Resilin shows an abundant (FIG. 3B) highly conserved $PX_4G$ motif populated by hydrophilic residues (FIG. 7); the conserved $PX_4G$ motif is a continuous motif not abundant in related elastomeric proteins (FIG. 3 A-B; FIG. 7).

The results revealed that distribution of Pro and Gly residues may be responsible for the elasticity and/or environmental responsiveness displayed by these proteins. Collagen, although not elastomeric, is thermoresponsive and presents a large number of both $PX_0G$ and $PX_1G$ motifs, and has a much larger Pro content than the proteins analyzed herein, particularly Pro residues at Pm1 and Pm2 at $PX_0G$ and $PX_1G$ motifs, respectively. The $PX_1G$ motifs have relatively low abundance in most elastomeric proteins described.

Figure 4:
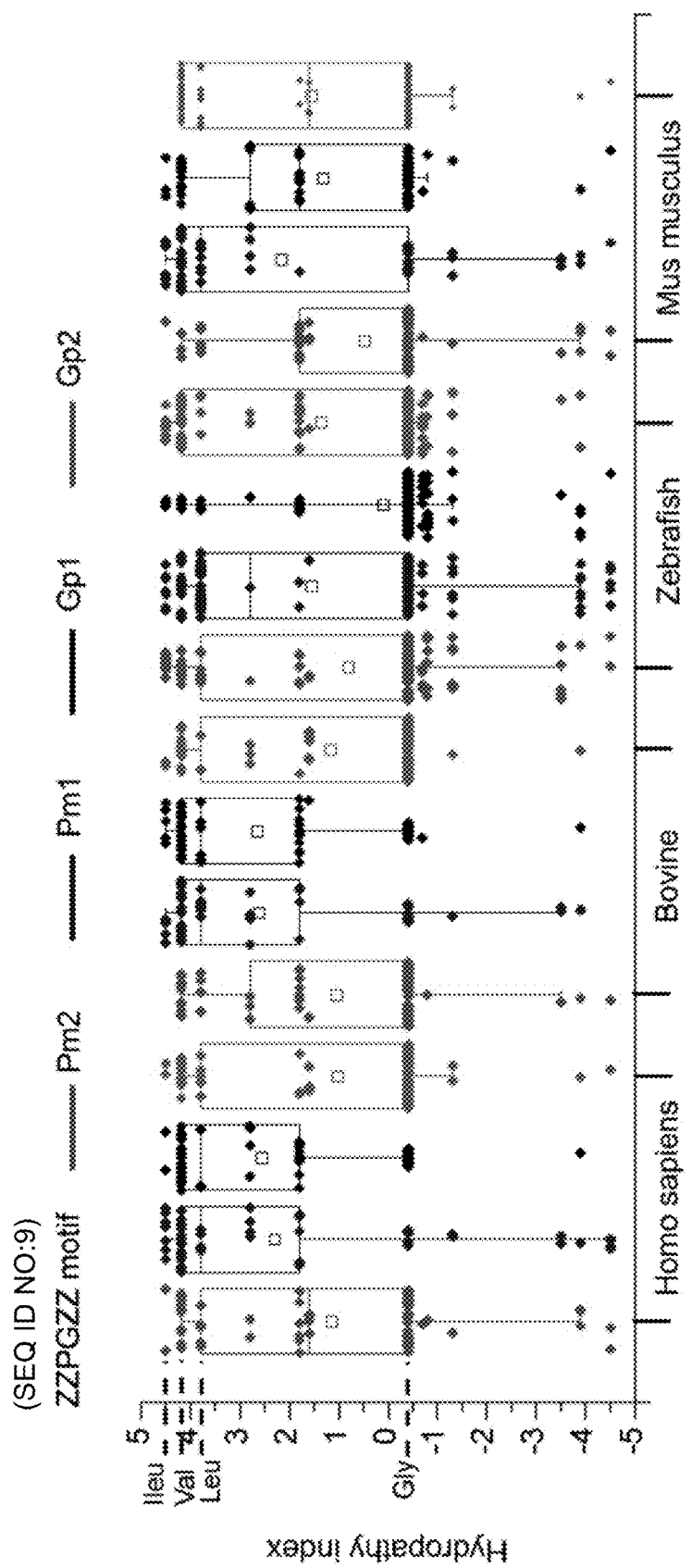
FIG. 4 is a graph showing the hydropathy index (Hi) distribution for residues surrounding $P(X_n)G$ motifs (n=0) in elastin sequences from *Homo sapiens*, Bovine, Zebrafish and *Mus musculus*. This analysis considers residues one position before (Pm1, for "Proline minus 1 residue") and 2 positions before (Pm2) a Proline residue in a $P(X_n)G$ motif, as well as residues one position after (Gp1, for "Gly plus 1 residue") and two positions after (Gp2) a Gly residue in a $P(X_n)G$ motif. The Hi was defined as proposed by Kyte and Doolittle (1982). The identity of the residues at a given position can be easily read from this figure (e.g., Gly=−0.4; Val=4.2; A=1.8, etc.). The box delineates the 25 and 95 percentile, and the mean hydropathy is indicated by a square; raw data is also included for each residue position as filled diamonds.
Figure 5:
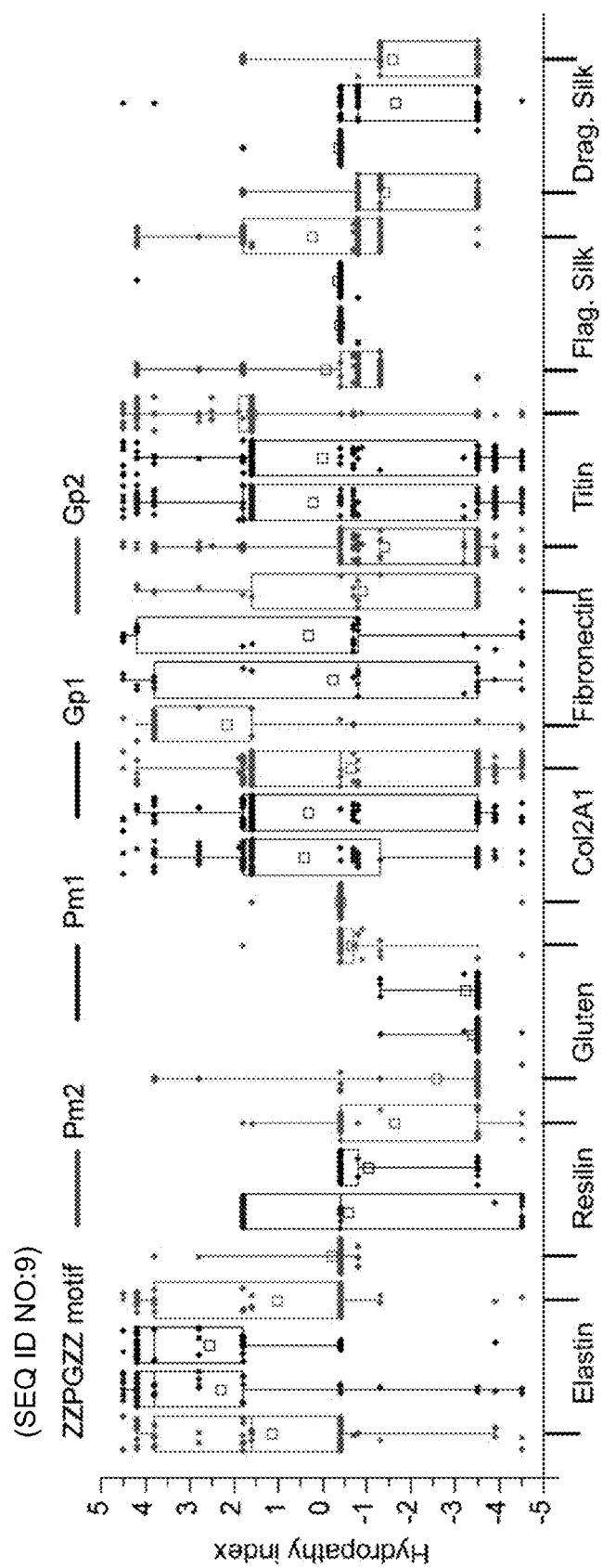
FIG. 5 is a graph showing hydropathy index (Hi) distribution for residues surrounding $P(X_n)G$ motifs (n=0) in elastin (*Homo sapiens*), resilin, gluten, collagen (type IIα1, Col2A1), fibronectin, titin, Flagelliform and Dragline silks. This analysis considers residues one position before (Pm1, for "Proline minus 1 residue") and 2 positions before (Pm2) a Proline residue on a $P(X_n)G$ motif, as well as residues one position after (Gp1, for "Gly plus 1 residue") and two positions after (Gp2) a Gly residue in a $P(X_n)G$ motif. The Hi was defined as proposed by Kyte and Doolittle (1982). The identity of the residues at a given position can be easily read from this figure (e.g., Gly=−0.4; Val=4.2; A=1.8, etc.). The box delineates the 25 and 95 percentile, and the mean hydropathy is indicated by a square; raw data is also included for each residue position as filled diamonds.

The canonical elastin-like motif includes $PX_0G$, where only the X residue in the pentapeptide motif VPGXG (SEQ ID NO: 3) was previously believed to be able to accept amino acids of any hydrophobicity. However, bioinformatic studies showed the occurrence of $PX_0G$ motifs with at least 4 positions surrounding the PG dipeptide covering a broad spectrum of hydropathy indices; indeed, there was no evidence for larger sequence diversity at Gp1 (equivalent to X in VPGXG; SEQ ID NO: 3) among elastin sequences and other elastomeric proteins (FIGS. 4 and 5). Therefore, to further test the hypothesis, a large data set of polypeptides were created incorporating PG, $PX_1G$, $PX_1X_2G$ (SEQ ID NO: 16) and $PX_1X_2X_3X_4G$ (SEQ ID NO: 66) motifs while varying the residues that surround or constitute the $P(X_n)G$ motifs, and engineering Gly residues at different positions around the $P(X_n)G$ motif to study the role of Gly at these positions, as suggested by the bioinformatics study below in Table 2.

TABLE 2

Minima functional environmentally sensitive motifs that were reverse engineered from the sequence of a variety of elastomeric and non-elastomeric proteins (see Table 2), and the experimental evidence from corresponding EIP motifs demonstrated to display elasticity and/or environmental sensitivity. EIPs of various lengths for a single repeat unit were generated to study the role of molecular weight on their behavior.

| Minimum functional motif | Repeat unit* | Z and X values | Equivalent EIP constructs Gp2, Pm2, Pm1 |
|---|---|---|---|
| $P(X_0)G$ $Z_1Z_2\mathbf{PG}Z_3Z_4$ | AVPGVG (SEQ ID NO: 8) | $Z_1 = A$, $Z_2 = V$, $Z_3 = V$, $Z_4 = G$ | Gp2 = G |
| | VAPGVG (SEQ ID NO: 67) | $Z_1 = V$, $Z_2 = A$, $Z_3 = V$, $Z_4 = G$ | Gp2 = G |
| | GVPGAV (SEQ ID NO: 68) | $Z_1 = G$, $Z_2 = V$, $Z_3 = A$, $Z_4 = V$ | Pm2 = G |
| | GVPGVA (SEQ ID NO: 69) | $Z_1 = G$, $Z_2 = V$, $Z_3 = V$, $Z_4 = A$ | Pm2 = G |
| | TVPGVG (SEQ ID NO: 70) | $Z_1 = T$, $Z_2 = V$, $Z_3 = V$, $Z_4 = G$ | Gp2 = G |
| | TVPGAG (SEQ ID NO: 71) | $Z_1 = T$, $Z_2 = V$, $Z_3 = A$, $Z_4 = G$ | Gp2 = G |
| | GAPGVG (SEQ ID NO: 72) | $Z_1 = G$, $Z_2 = A$, $Z_3 = V$, $Z_4 = G$ | Gp2 = G & Pm2 = G |
| | AVPGVA (SEQ ID NO: 73) | $Z_1 = A$, $Z_2 = V$, $Z_3 = V$, $Z_4 = A$ | Gp2 <> G & Pm2 <> G |
| | GAPGGG (SEQ ID NO: 74) | $Z_1 = G$, $Z_2 = A$, $Z_3 = G$, $Z_4 = G$ | Gp2 = G & Pm2 = G |
| | GAPGAG (SEQ ID NO: 75) | $Z_1 = G$, $Z_2 = A$, $Z_3 = A$, $Z_4 = G$ | Gp2 = G & Pm2 = G |
| | GGPGAG (SEQ ID NO: 76) | $Z_1 = G$, $Z_2 = G$, $Z_3 = A$, $Z_4 = G$ | Gp2 = G & Pm2 = G & Pm1 = G |
| $P(X_1)G$ $Z_1Z_2\mathbf{PX_1G}Z_3Z_4$ | GVPAGVG (SEQ ID NO: 77) | $Z_1 = G$, $Z_2 = V$, $X = A$, $Z_3 = V$, $Z_4 = G$ | Gp2 = G & Pm2 = G |
| | VGPVGVG (SEQ ID NO: 78) | $Z_1 = V$, $Z_2 = G$, $X = V$, $Z_3 = V$, $Z_4 = G$ | Gp2 = G & Pm1 = G |
| | GVPTGVG (SEQ ID NO: 79) | $Z_1 = G$, $Z_2 = V$, $X = T$, $Z_3 = V$, $Z_4 = G$ | Gp2 = G & Pm2 = G |

TABLE 2-continued

Minima functional environmentally sensitive motifs that were reverse engineered from the sequence of a variety of elastomeric and non-elastomeric proteins (see Table 2), and the experimental evidence from corresponding EIP motifs demonstrated to display elasticity and/or environmental sensitivity. EIPs of various lengths for a single repeat unit were generated to study the role of molecular weight on their behavior.

| Minimum functional motif | Equivalent EIP constructs | | |
|---|---|---|---|
| | Repeat unit* | Z and X values | Gp2, Pm2, Pm1 |
| | GAPGVG (SEQ ID NO: 80) | $Z_1 = G$, $Z_2 = A$, $X = V$, $Z_3 = V$, $Z_4 = G$ | Gp2 = G & Pm2 = G |
| | VAPVGVA (SEQ ID NO: 81) | $Z_1 = V$, $Z_2 = A$, $X = V$, $Z_3 = V$, $Z_4 = A$ | Gp2 <> G & Pm2 <> G |
| | GAPFGFA (SEQ ID NO: 82) | $Z_1 = G$, $Z_2 = A$, $X = F$, $Z_3 = F$, $Z_4 = A$ | Pm2 = G$^\Psi$ |
| | AIPMGAG (SEQ ID NO: 83) | $Z_1 = A$, $Z_2 = I$, $X = M$, $Z_3 = A$, $Z_4 = G$ | Gp2 = G$^\Psi$ |
| | GFPTGGL (SEQ ID NO: 84) | $Z_1 = G$, $Z_2 = F$, $X = T$, $Z_3 = G$, $Z_4 = L$ | Pm2 = G$^\Psi$ |
| | LAPFGMG (SEQ ID NO: 85) | $Z_1 = L$, $Z_2 = A$, $X = F$, $Z_3 = M$, $Z_4 = G$ | Gp2 = G$^\Psi$ |
| | GLPAGMG (SEQ ID NO: 86) | $Z_1 = G$, $Z_2 = L$, $X = A$, $Z_3 = M$, $Z_4 = G$ | Gp2 = G & Pm2 = G$^\Psi$ |
| P(X$_2$)G $Z_1Z_2PX_1X_2GZ_3$ | GVPAVGV (SEQ ID NO: 87) | $Z_1 = G$, $Z_2 = V$, $X_1 = A$, $X_2 = V$, $Z_3 = V$ | Pm2 = G |
| | GVPHVGV (SEQ ID NO: 88) | $Z_1 = G$, $Z_2 = V$, $X_1 = H$, $X_2 = V$, $Z_3 = V$ | Pm2 = G |
| | VGPAVGV (SEQ ID NO: 89) | $Z_1 = V$, $Z_2 = G$, $X_1 = A$, $X_2 = V$, $Z_3 = V$ | Gp2 = G & Pm1 = G |
| | VTPAVGV (SEQ ID NO: 90) | $Z_1 = V$, $Z_2 = T$, $X_1 = A$, $X_2 = V$, $Z_3 = V$ | Gp2 <> G & Pm2 <> G |
| P(X$_4$)G $Z_1Z_2PX_1X_2X_3X_4GZ_3Z_4$ | GVPSALYGVG (SEQ ID NO: 91) | $Z_1 = G$, $Z_2 = V$, $X_1 = S$, $X_2 = A$, $X_3 = L$, $X_4 = Y$, $Z_3 = V$, $Z_4 = G$ | Gp2 = G & Pm2 = G |
| | GVPSDDYGQG (SEQ ID NO: 92) | $Z_1 = G$, $Z_2 = V$, $X_1 = S$, $X_2 = D$, $X_3 = D$, $X_4 = Y$, $Z_3 = Q$, $Z_4 = G$ | Gp2 = G & Pm2 = G** |
| | GVPSDDYGVG (SEQ ID NO: 93) | $Z_1 = G$, $Z_2 = V$, $X_1 = S$, $X_2 = D$, $X_3 = D$, $X_4 = Y$, $Z_3 = V$, $Z_4 = G$ | Gp2 = G & Pm2 = G** |

*Letters underlined are not part of the EIP repeat unit in the constructed polypeptides, but correspond to a residue in the n ± 1 repeat unit as it is presented in tandem.
$^\Psi$The functionality of these motifs was assessed as part of a single polypeptide generated by using a method that randomized the selection of amino acids for 5 hexapeptides following a $Z_1Z_2PX_1GZ_3$ (SEQ ID NO: 22) motif, which were then repeated in tandem. The design principle entailed having a G residue at either Pm2 or Gp2. A normal distribution was used for selection of residues with a target Hi of 2 for both X and Z residues and a standard deviation of 1.5. The sequence of such randomized polypeptide is: (GAPFGFAIPMGAGFPTGGLAPFGMGLPAGM)$_n$ ((SEQ ID NO: 12)$_n$).
**These elastic sequences display thermal stability and solubility due to the large contribution of the hydrophilic aspartate residues confined within the PXXXXG (SEQ ID NO: 94) motif to the inverse transition temperature of these sequences.

The environmental responsiveness of the motifs in Table 2 (see FIGS. 8-16) was characterized and demonstrated the robustness of the P(X$_n$)G motifs to confer environmental sensitivity and elasticity to polypeptides, and the possibility to engineer flexible functional $Z_mP(X_n)GZ_k$ (SEQ ID NO: 95) motifs, wherein $Z_m$ and $Z_k$ are each amino acids of any hydrophobicity which surround the P(X$_n$)G functional unit and n, m, k≤4. For simplicity and clarity, the data in FIG. 8 through 16 is presented by grouping all the polypeptides described by a common $Z_mP(X_n)GZ_k$ (SEQ ID NO: 95) motif.

Figure 17:
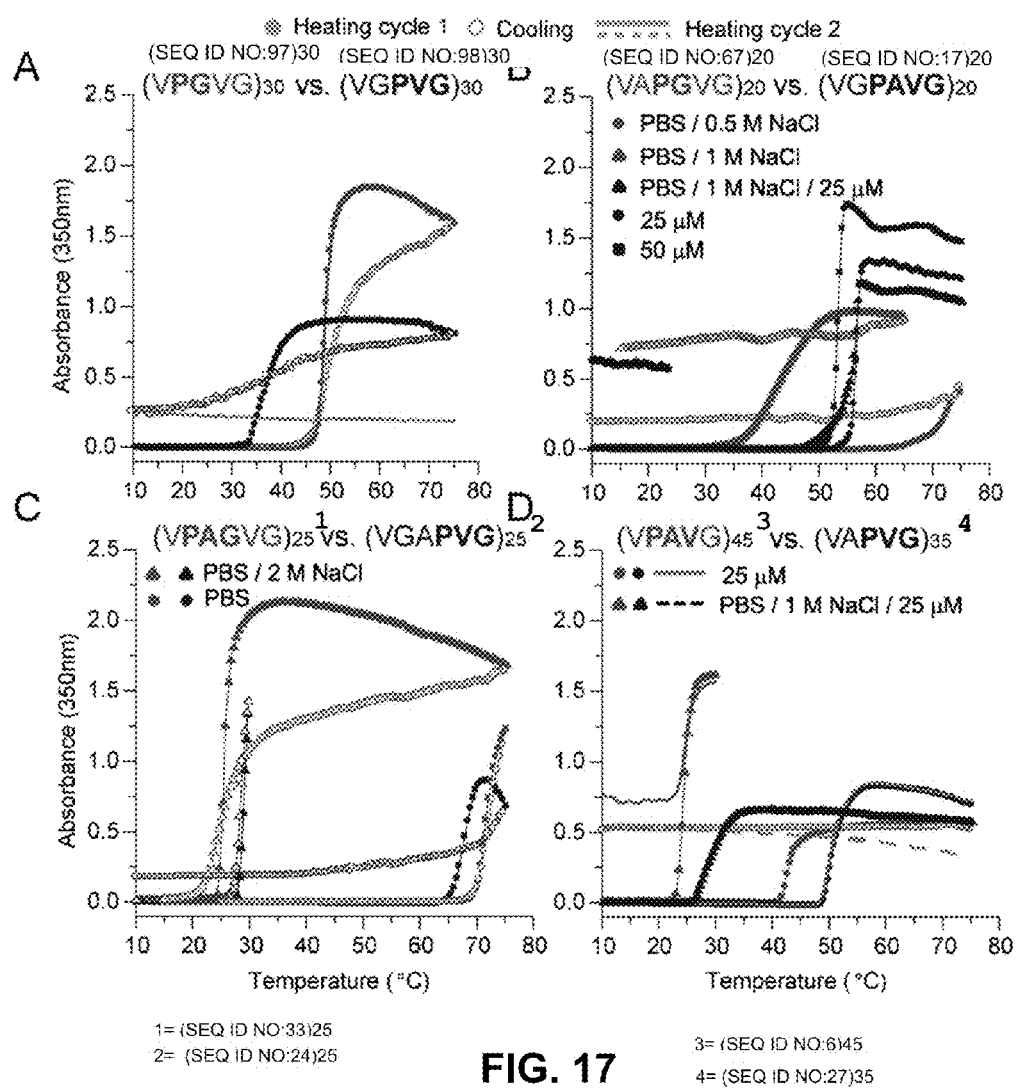
FIG. 17 depicts graphs showing retro-EIPs display thermoresponsive behavior distinct to the observed in the parent EIP (shown in red) despite having the same hydrophobicity profiles and amino acid side-chain relationships. Occurrence of Gly at Pm1 (GP motif) upon backbone reversal resulted in a pronounced decrease in the Tt and the emergence of heat-irreversible phase separation upon heating above a threshold temperature (A-B). Noteworthy, the difference in the Tt observed in (A) is underestimated, as the Tt of (VPGVG)$_{30}$ is likely to be ~10° C. higher than shown, since this construct lacks a His-tag present in (VGPVG)$_{30}$; then, the overall ΔTt in (A) is ~30° C., which is likely to be similar to the ΔTt observed in (B). Retro-EIP in (C), wherein the parent PX$_1$G motif was conserved, suggests that overall hydrophobicity is a good predictor of the inverse transition temperature of $Z_1Z_2PX_1GZ_1Z_2$ (SEQ ID NO: 13) motifs. The large hysteresis displayed by VPAVG (SEQ ID NO: 6) (See FIG. 15A), is absent in the corresponding retro-EIP (D). Samples were prepared in PBS at 50 µM unless indicated.

The characterization of retro-EIPs, in which the sequence of the motif was backbone reversed (see Table 3 below) while regenerating a $PX_nG$ motif typically with different n value, further demonstrated the robustness of these motifs since environmentally sensitivity was maintained in all cases (see FIG. 17). Backbone reversal of the motif APGVG (Table 2) would result in an EIP with a $PX_1X_2X_3G$ (SEQ ID NO: 96) motif, which constitutes an additional minima functional motif $Z_mP(X_n)GZ_k$ where n=3.

structure, particularly their helical conformation, is key to the self-assembly process in this fractal manner (Sheparavych, R. et al. (2009) *Biomacromolecules* 10:1955-1961). Interestingly, the bioinformatics analyses only pointed to the occurrence of Gly at Pm1 for collagen and silks, and in both cases, abundant secondary and tertiary structures are present, which is in agreement with the finding that Gly at Pm1 increases the propensity of these motifs to drive irreversible phase separation and disruption of elasticity above a critical temperature.

TABLE 3

Backbone-reversed -retro- EIPs. The sequence of an EIP motif as read from the N- to C-terminus was reversed so that the sequence was identical when read from the C- to N- terminus. In addition, whenever a Gly residue occurred at Pm1 as a result of backbone reversal, a modified retro-motif was synthesized in which an Ala or Thr residue was substituted for Gly, in order to study the effect of Gly at Pm1.

| Motif | | Retro-motif | | Modified retro-motif* | |
|---|---|---|---|---|---|
| Minimum unit | EIP | Minimum unit | EIP | Minimum unit | EIP |
| $PX_0G$ | VPGVG (SEQ ID NO: 97) | $PX_1G$ | VGPVG (SEQ ID NO: 98) | $PX_1G$ | V<u>A</u>PVG |
| $PX_0G$ | VAPGVG (SEQ ID NO: 67) | $PX_2G$ | VGPAVG (SEQ ID NO: 17) | $PX_2G$ | V<u>T</u>PAVG |
| $PX_1G$ | VPAGVG (SEQ ID NO: 33) | $PX_1G$ | VGAPVG (SEQ ID NO: 24) | | — |
| $PX_2G$ | VPAVG (SEQ ID NO: 6) | $PX_1G$ | VAPVG (SEQ ID NO: 27) | | — |

*The modified (substituted or inserted) residue from the original retro-motif is shown underlined.

Figure 6:
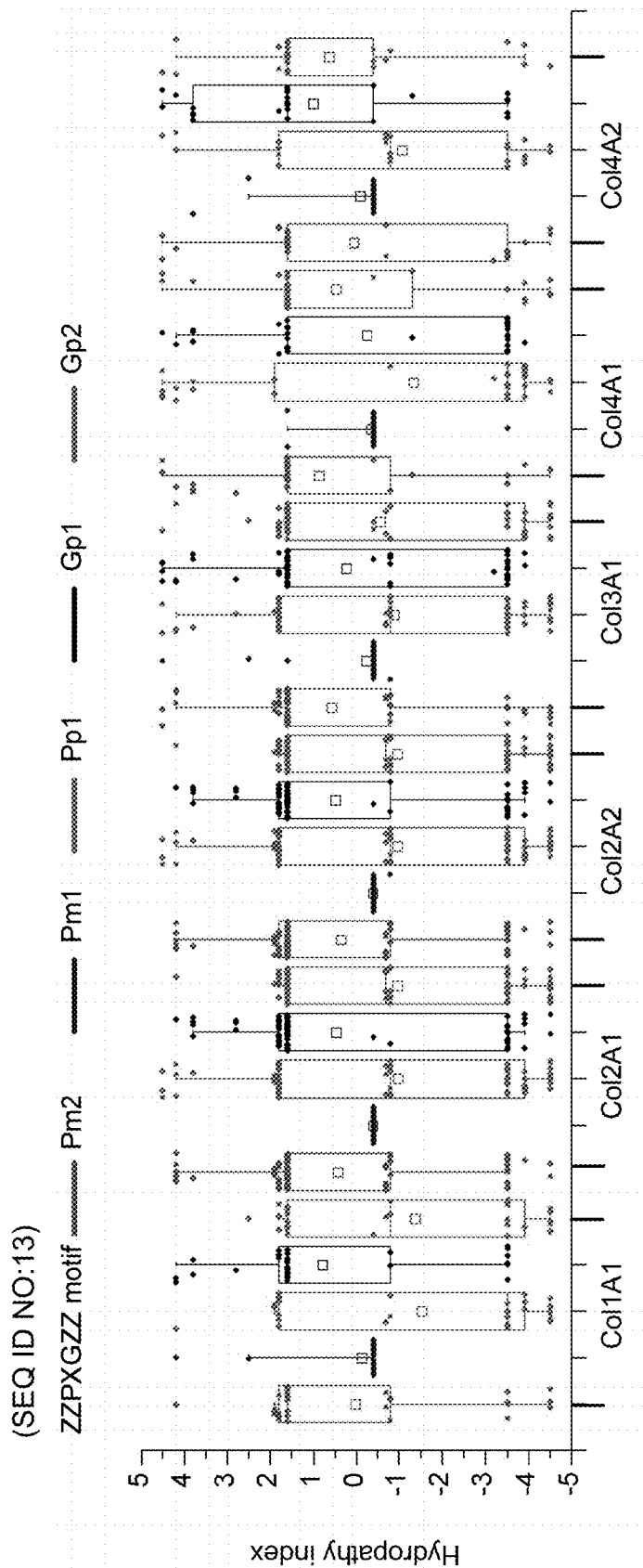
FIG. 6 is a graph showing hydropathy index (Hi) distribution for residues comprising and surrounding $P(X_n)G$ motifs (n=1) in collagen. In addition to Pm2, Pm1, Gp1 and Gp2, this analysis considers the residue Pp1 (for "Pro plus 1 position"), which is equivalent to the X residue constituting the $P(X_n)G$ motif. The Hi was defined as proposed by Kyte and Doolittle (1982). The identity of the residues at a given position can be easily read from this figure (e.g., Gly=−0.4; Val=4.2; A=1.8, etc.). The box delineates the 25 and 95 percentile, and the mean hydropathy is indicated by a square, raw data is also included for each residue position as filled diamonds.
Figure 11:
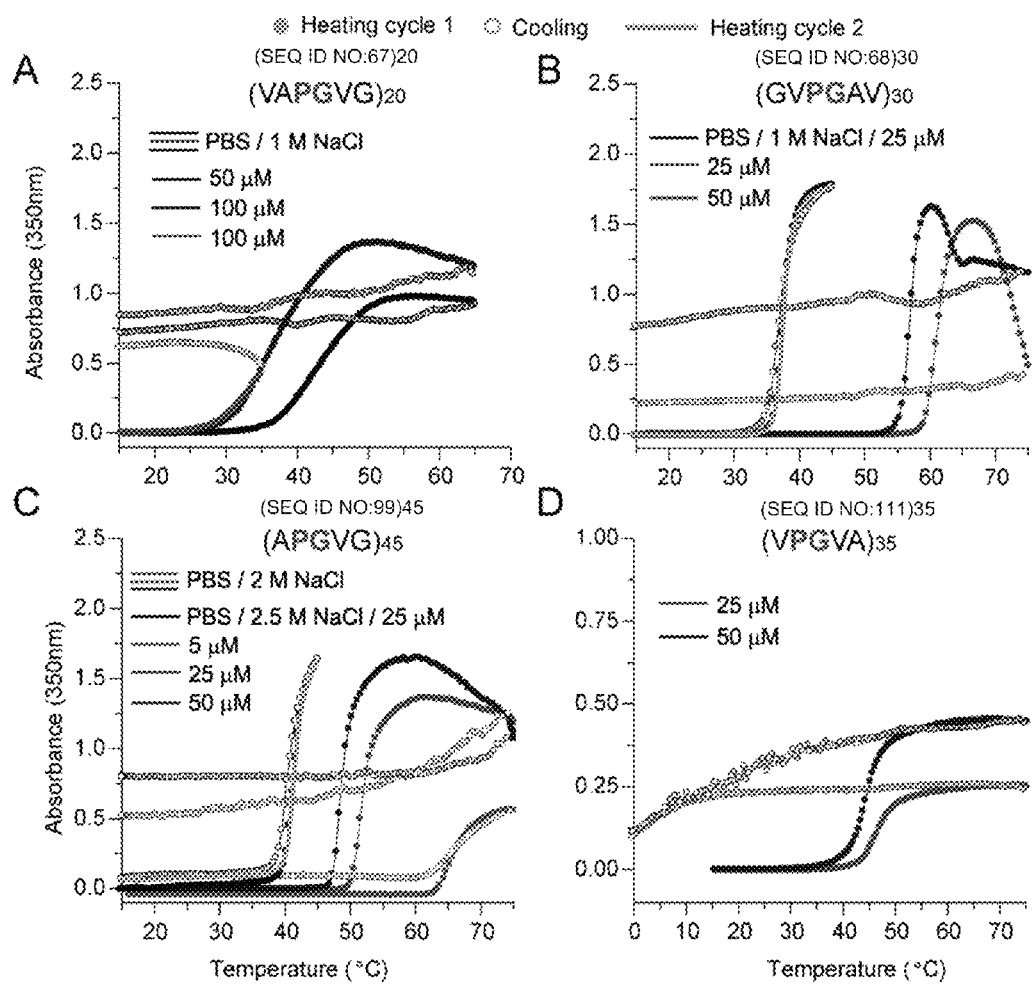
FIG. 11 depicts graphs showing reversible and heat-irreversible phase transition behavior displayed by some EIPs with $Z_1Z_2PGZ_3Z_4$ (SEQ ID NO: 9) motif. This family of EIPs displays inverse phase transition behavior characterized by a sharp phase separation and self-assembly upon heating above their LCST or Tt, which may be reversible or irreversible for temperatures below or above a threshold temperature (A-D), and which may also be concentration dependent (C). The number of repeats in each protein-polymer is shown in the legend. Unless indicated in the legend, the samples were prepared at 50 µM in PBS.
Figure 12:
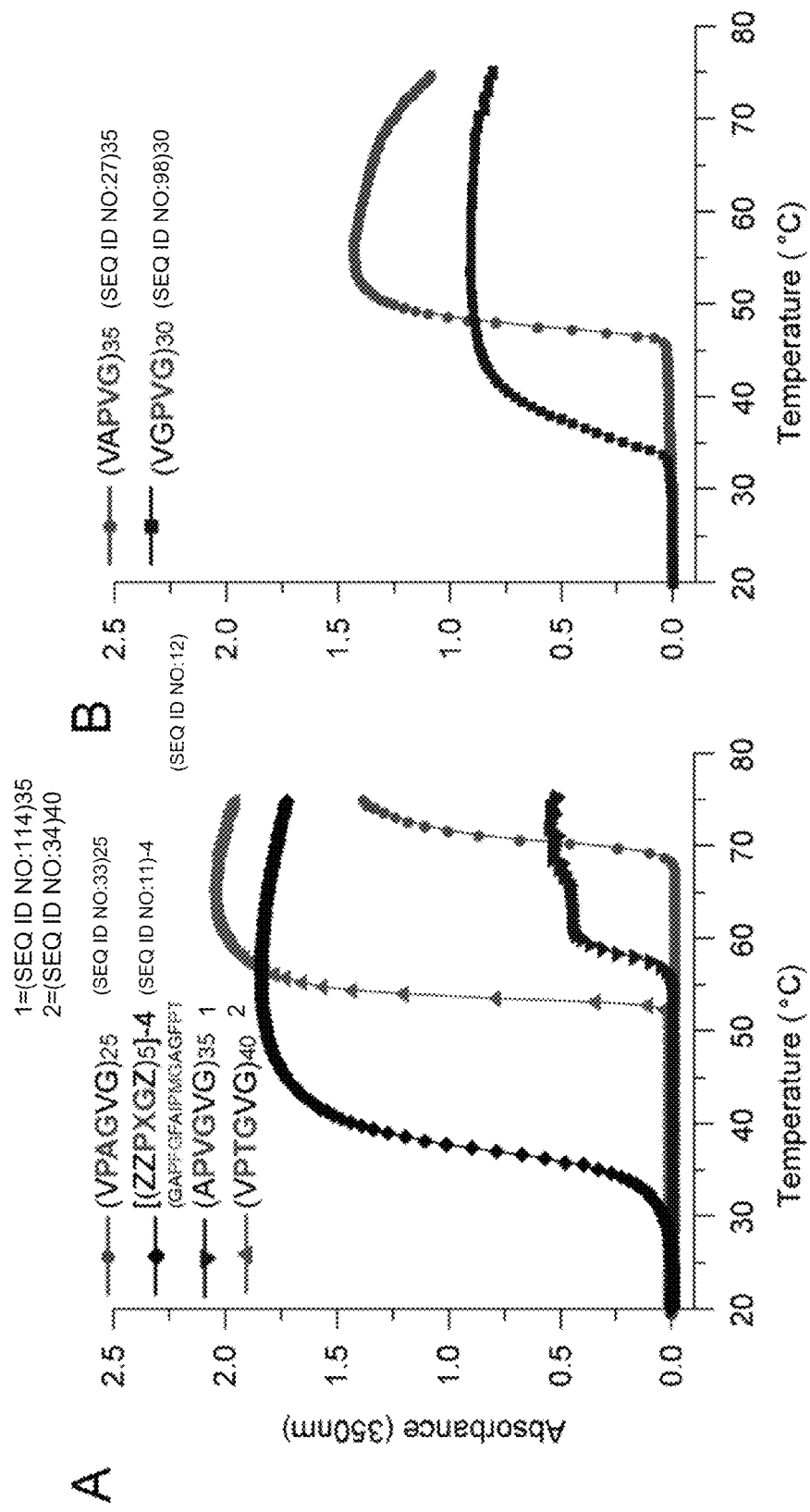
FIG. 12 depicts graphs showing results of environmental sensitivity of EIPs with $Z_1Z_2PGZ_3Z_4$ (SEQ ID NO: 9) motif, exemplified for both hexapeptide (A) and pentapeptide (B) repeat units. This family of EIPs displays inverse phase transition behavior characterized by a sharp phase separation and self-assembly upon heating above the LCST or Tt of each polypeptide. The number of repeats in each protein-polymer is indicated in the legend. All samples were prepared at a concentration of 50 µM in PBS, with the exception of the randomized EIP ([(ZZPXGZ)$_5$]-$_4$) [(SEQ ID NO: 11)$_5$]-$_4$ with sequence (GAPFGFAIPMGAGFPTGGLAPFG-MGLPAGM)$_4$, (SEQ ID NO: 12)$_4$ which was prepared in PBS with 6 M Urea and 1M NaCl.
Figure 13:
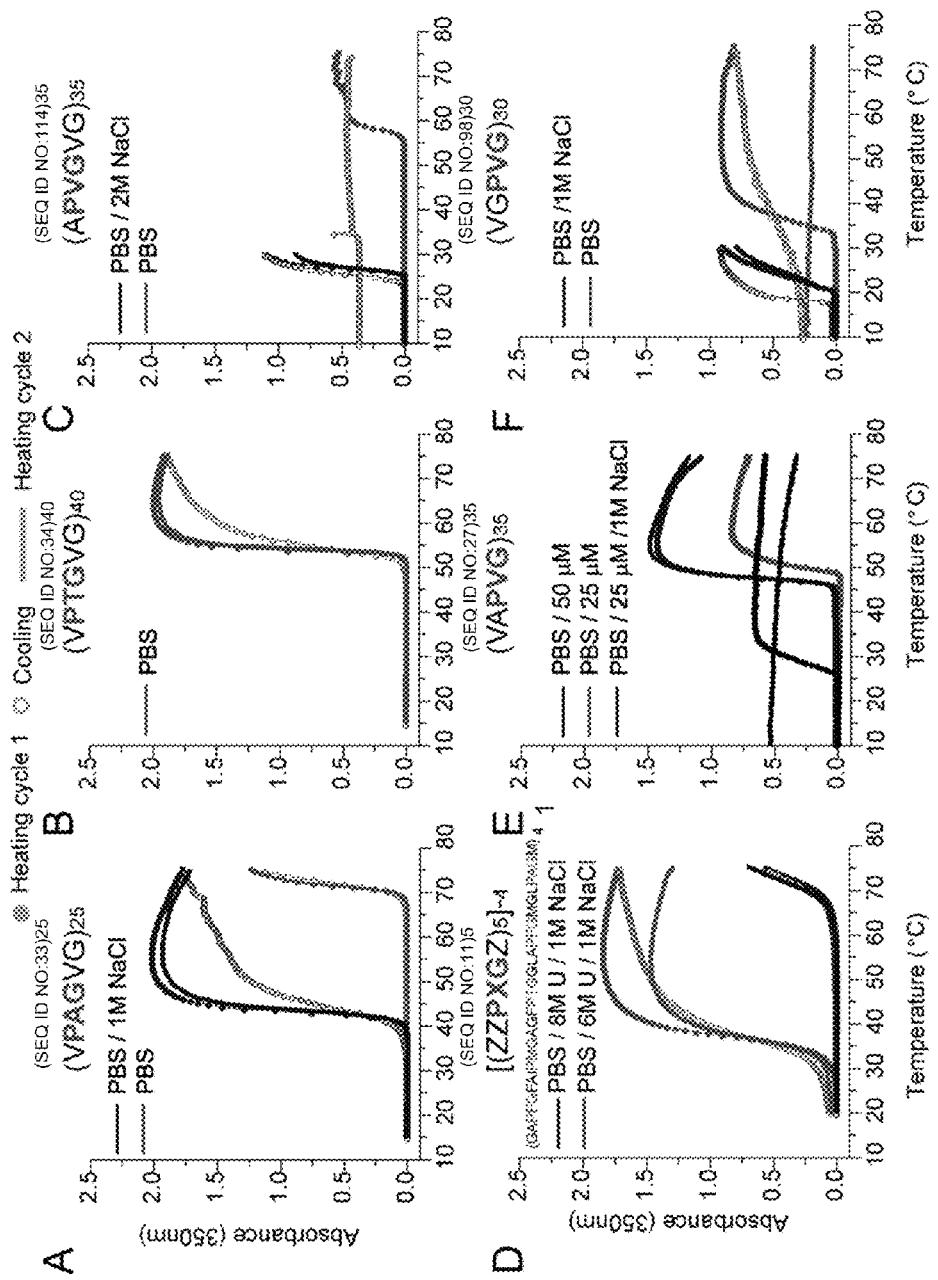
FIG. 13 depicts graphs showing the reversible and heat-irreversible phase transition behavior displayed by different EIPs with $Z_1Z_2PX_1GZ_3Z_4$ (SEQ ID NO: 13) motif. This family of EIPs displays inverse phase transition behavior characterized by a sharp phase separation and self-assembly upon heating above the polypeptides LCST or Tt, which may be reversible (A, B, D, E), or irreversible (C, F) for temperatures above a threshold temperature or for buffer ionic strengths above a threshold ionic strength (E). The number of repeats in each protein-polymer is shown in the legend. Unless indicated in the legend, the samples were prepared in PBS at 50 µM.
Figure 14:
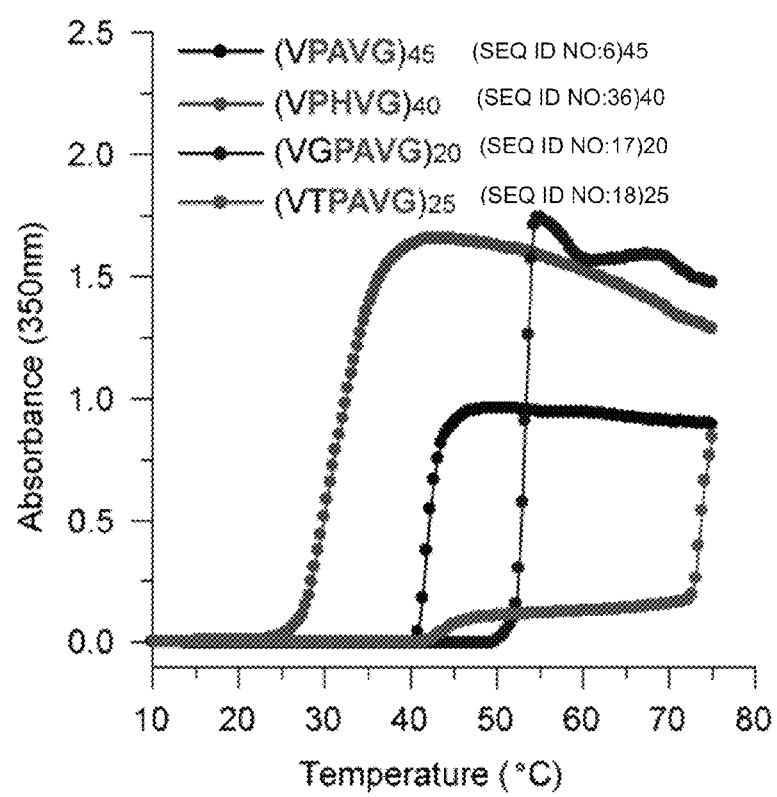
FIG. 14 is a graph showing results of environmental sensitivity of EIPs with $Z_1Z_2PX_1X_2GZ_3Z_4$ (SEQ ID NO: 14) motif, exemplified for both hexapeptide and pentapeptide repeat units. This family of EIPs displays inverse phase transition behavior characterized by a sharp phase separation and self-assembly upon heating above the LCST or Tt of each polypeptide. The number of repeats in each protein-polymer is indicated in the legend. All samples were prepared at a concentration of 50 µM in PBS.
Figure 15:
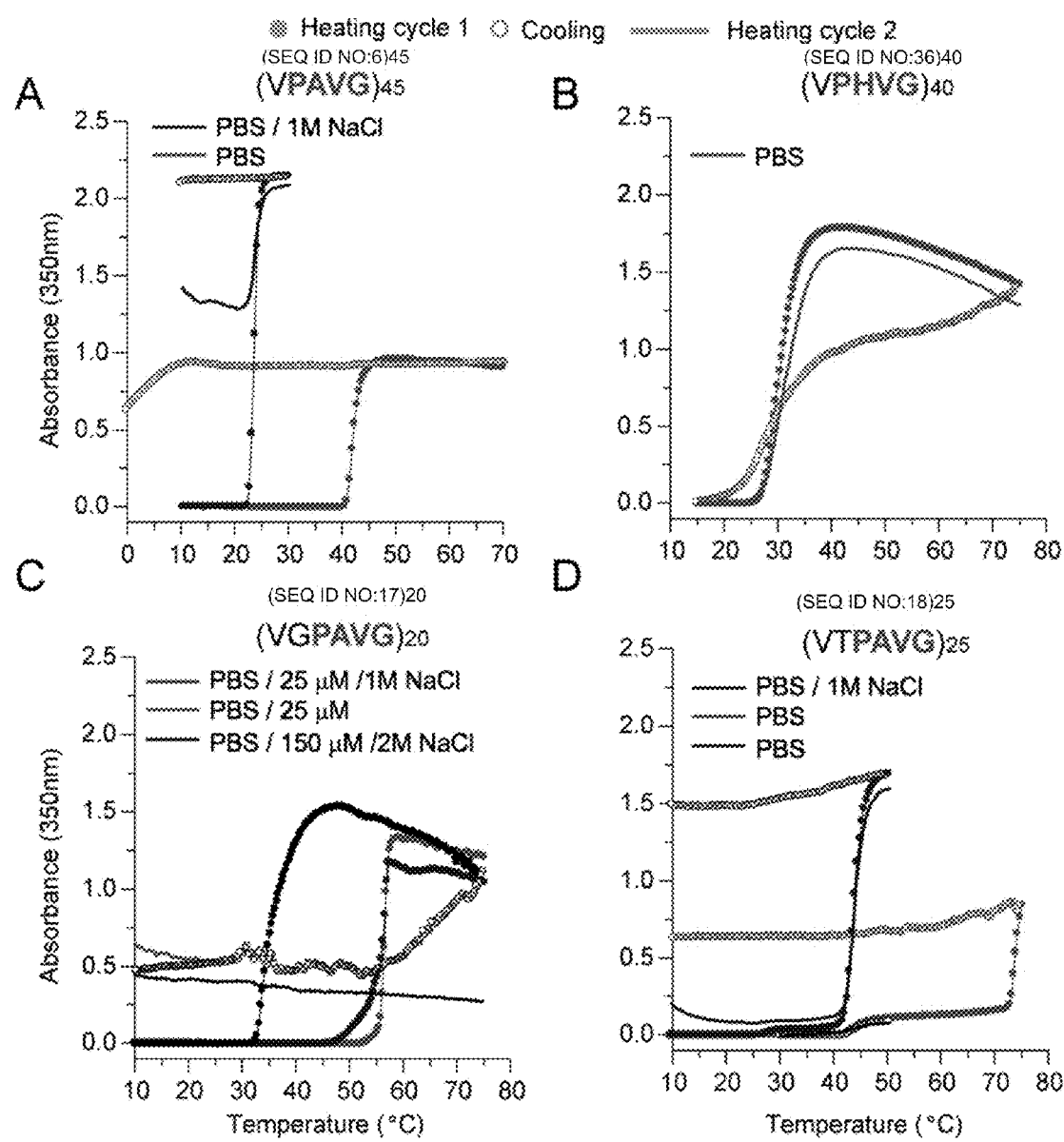
FIG. 15 depicts graphs showing the reversible and heat-irreversible phase transition behavior displayed by different EIPs with $Z_1Z_2PX_1X_2GZ_3Z_4$ (SEQ ID NO: 14) motif. This family of EIPs displays inverse phase transition behavior characterized by a sharp phase separation and self-assembly upon heating above the polypeptide LCST or Tt, which may be reversible (A, B), or irreversible (C, D) for temperatures above a threshold temperature. The number of repeats in each protein-polymer is shown in the legend. Unless indicated in the legend, the samples were prepared in PBS at 50 µM.
Figure 16:
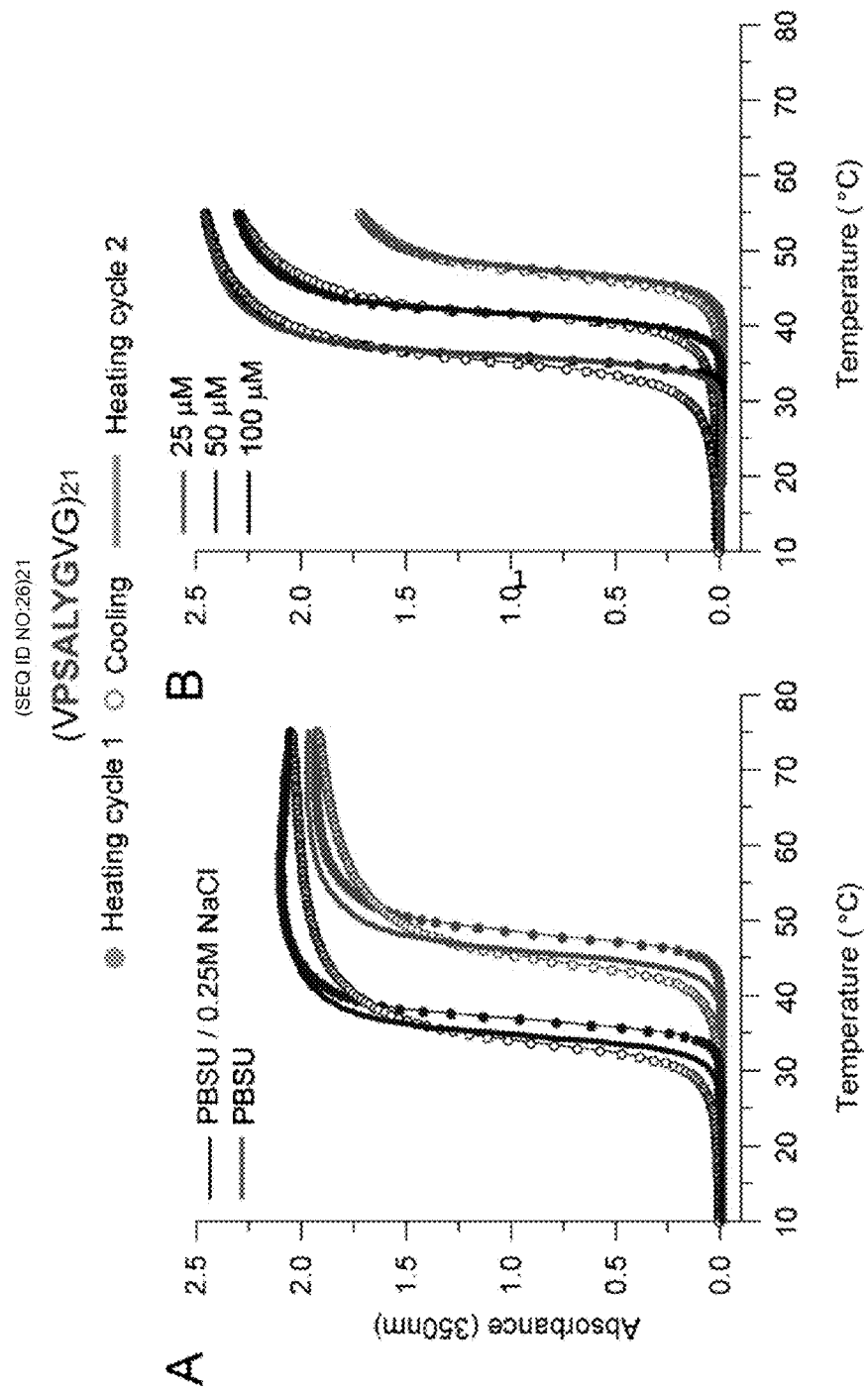
FIG. 16 depicts graphs showing reversible phase transition behavior by an EIP with $Z_1Z_2PX_1X_2X_3X_4GZ_3Z_4$ (SEQ ID NO: 15) motif. This EIP displays reversible inverse phase transition behavior characterized by a sharp phase separation and self-assembly upon heating above its LCST or Tt, followed by disassembly upon lowering the temperature below the LCST (A-B). Furthermore, upon heating in a second heating cycle (A-B), this EIP retains its environmental sensitivity. Samples in (A) were prepared at 25 µM in PBS and 8 M Urea, pH 7 (PBSU), and samples in (B) were prepared in PBS 8 M Urea at pH 9 at the indicated concentrations.

The data showed that biased selection of amino acids in key motifs observed in repetitive proteins is representative of the evolutionary constraints experienced by different species. A surprising bias in the localization of Gly residues at Pm2 and Gp2 (at either position or simultaneously occurring for a given $PX_nG$ repeat unit) surrounding $PX_nG$ motifs in elastomeric proteins (see FIGS. 4-6) is not a prerequisite for the reversible phase transition behavior displayed by elastomeric-inspired polypeptides, as demonstrated by EIPs with motifs VAPVG (SEQ ID NO: 27) (FIG. 13) and APGVG (SEQ ID NO: 99) (FIG. 11). This observation reinforces the possibility of constructing truly general motifs as described in Table 2, where Z residues do not have to be restricted to Gly at either Pm1 or GP2, while still preserving the environmental sensitivity and elasticity observed in other $Z_mP(X_1)GZ_k$ (SEQ ID NO: 95) and $Z_mPGZ_k$ (SEQ ID NO: 100) motifs. In addition, the demonstration of the environmental sensitivity of a randomized EIP with repeat unit $Z_1Z_2PX_1GZ_2Z_3Z_4PX_2GZ_6Z_7Z_8PX_3GZ_9Z_{10}Z_nPX_4GZ_{12}Z_0Z_{14}PX_5GZ_{15}$ (SEQ ID NO: 101) displaying a minima functional $PX_1G$ motif constitutes a step further in the design of "smart" protein-polymers (see FIG. 12A).

Regarding the role of neighboring Gly residues in the functionality of the $P(X_n)G$ motif, FIG. 18 demonstrates that Gly at Pm1 of a $P(X_n)G$ facilitates self-assembly, presumably by making the packing of the polypeptide chains more efficient due to reduced steric hinderance provided by the side-chain motifs having a more hydrophobic residue at Pm1, and by promoting the formation of stable non-reversible fibrillar structures rather than driving the self-assembly of fractal structures. Sheparavych et al. have shown that for other self-assembling peptides, the disruption of the peptide secondary In addition, it has also been shown that other interesting self-assembly properties for $PX_1X_2G$ motifs, as shown in FIG. 19, and as reported in the literature for the ELP with sequence VPAVG (SEQ ID NO: 6), which also carries a $PX_1X_2G$ (SEQ ID NO: 102) motif (see, e.g, Bessa, P. C. et al. (2009) supra).

An additional feature of the EIP motifs disclosed in the present disclosure is the possibility to exploit their environmental sensitivity for their efficient purification, in an analogous manner to the purification schemes in use for the preparation of ELPs. It has been observed by the inventors that even those EIPs that display heat-irreversible phase separation, typically display reversible phase separation in response to changes in buffer ionic strength, and this property has been exploited for their high yield purification. However, the expression (in *E. coli*) and purification of EIPs with Gly at Pm1 is somewhat more difficult compared with the ease of purification of other EIPS, primarily due to their tendency to form insoluble aggregates and form inclusion bodies during protein expression. Interestingly, although Gly at Pm1 may drive the heat-irreversible phase separation, it does not necessarily disrupt the reversible phase separation when using an orthoganol stimulus, such as buffer ionic strength.

It was reasoned that EIPs displaying heat-irreversible inverse phase transition can be engineered as elastomeric or non-elastomeric materials if cross-linked below or above the threshold temperature for the heat-irreversible phase separation of a given EIP. This is in accordance with Urry's observation that potential elastomers display reversible aggregation, whereas non-elastomeric polypeptides display irreversible aggregations (U.S. Pat. No. 5,250,516). Noteworthy, the cross-linking conditions could be readily adjusted to tune the transition temperature (Tt) of the polypeptide to a temperature range below the threshold temperature, by exploiting the sensitivity of EIPs to changes in buffer ionic strength. In addition, it has also been observed by the inventors that such threshold temperature is typically above body temperature, so that devices composed of EIPs displaying heat-irreversible phase separation should not be compromised upon implantation, especially if cross-linked. In addition, heat-irreversible phase separation or non-elastomeric behavior may be favored by engineering Gly residues at Pm1 or $PX_nG$ minima functional motifs that would promote the formation of stable perhaps crystallizable structures above a threshold temperature above the Tt. A recent study by Chen and Guan supports the idea that the localization of Pro and Gly residues in the canonical ELP motif VPGXG (SEQ ID NO: 3) serves a role in disrupting secondary structures that would otherwise prevent the highly elastic behavior and dynamic nature of these polypeptides, and rather promote the formation of random coils or dynamic low stability conformations as those based on β-turns and Polyproline-II conformations (Chen, Y. et al. (2009) *J. Am. Chem. Soc.* DOI:1021/ja9104446). Therefore, the ability to engineer the development of such ordered structures in unordered EIPs may provide additional means to control the elasticity of a protein-polymer in a stimuli-controlled manner.

In addition, the present disclosure describes the thermally responsive behavior of resilin-inspired polypeptides. Resilin-like polypeptides with the 11 residue repeat AQTPSSQYGAP (SEQ ID NO: 103) have been regarded in the literature as unordered polypeptides and were not reported to show thermally responsive behavior. A highly conserved YGAP (SEQ ID NO: 104) motif was suspected to be required for the properties, namely elasticity and resilience, of this polypeptide (see, e.g., Nairn, K. M. et al. (2008) supra). In contrast, the present disclosure indentifies a functional $PX_4G$ motif in resilin, which can also be identified in the repeat unit AQTPSSQYGAP (SEQ ID NO: 103), and demonstrated its environmental sensitivity (FIG. 16) and the possibility to generalize the sequence.

The present disclosure demonstrates the possibility to synthesize bioactive EIPs for tissue engineering and regenerative medicine applications by synthesizing EIPs incorporating the bioactive potent proangiogenic GXXPG (SEQ ID NO: 21) motif found in elastin (see, e.g., Robinet, A. et al. (2005) *J. Cell Science* 118:343-356), which display identical behavior to nonbioactive conventional elastin-like polypeptides and thus display remarkable environmental sensitivity and elasticity (FIG. 20). This is the first demonstration of an elastic, environmentally sensitive polypeptide carrying a potent chemokine, since non-elasticity of the VAPGVG (SEQ ID NO: 67) hexapeptide has frustrated major engineering efforts exploiting the functionality of this bioactive motif.

A large number of genetically encoded protein-based polymers were synthesized that span the entire range of Pro-$X_n$-Gly arrangements observed in the bioinformatics studies (that is, n=0-4), to assess whether they retained the phase behavior characteristic of the canonical Val-Pro-Gly-X-Gly (SEQ ID NO: 3) motif found in tropoelastin. FIG. 21 confirms that all these new arrangements of Pro and Gly residues are conducive to "smart" biopolymers with stimuli-responsive, phase transition behavior analogous to that of tropoelastin. These protein-polymers appear to have similar secondary structure propensities as elastin-like polypeptides and display an ensemble of highly dynamic conformers characteristic of other IDPs (FIG. 21C). This exciting finding significantly relaxes the sequence constraints on these polymers, as it allows for the incorporation of a number of short motifs within the $PX_nG$ unit or in the surrounding residues—10 residues between $PX_nG$ units are permissible. For instance, a number of neuroactive proteins present their bioactive sequences as tandem repeats embedded within $PX_4G$ units. Pro-rich proteins use tandem repeats of $PX_4G$ motifs for the presentation of bioactive peptides. The two neuroactive proteins FARXamide-related neuropeptides and PRQFVamide display tandem repeats of the bioactive peptides PFLRF (SEQ ID NO: 108) and PRQFV (SEQ ID NO: 109) embedded within $PX_4G$ motifs. A similar localized region of $PX_4G$ units was observed with highly conserved $X_4$ residues in a transcription factor from yeast (SPT5).

It is also possible to identify "smart" biopolymers with three types of phase behavior marked by three degrees of hysteresis in the reversibility of their thermally-triggered phase transition: i) zero, ii) finite, and iii) heat-sensitive infinite hysteresis (FIG. 21D). The "heat-sensitivity" of the latter category refers to the finding that these protein-polymers display zero hysteresis below a critical threshold temperature (typically around 40° C. for the polymers herein synthesized). Six different environmentally responsive polypeptides $(VGAPVG)_{35}$, $(VGPVG)_{30}$, $(VGPAVG)_{20}$, $(VPGAVG)_{30}$, $(VTPAVG)_{25}$, and $(TPVAVG)_{30}$, (repeats of SEQ ID NOs: 24, 98, 17, 38, 18 and 31 respectively) were found to show irreversible phase separation when heated to 75° C., whereas they displayed reversible phase transition behavior if heated below a given threshold temperature. The $(TPVAVG)_{30}$ (SEQ ID NO: 31) polypeptide was purified by exploiting the reversibility of its phase behavior in response to changes in ionic strength. Environmentally responsive polypeptides with the repeat unit (VTPAVG) (SEQ ID NO: 18) exhibited a very complex phase transition behavior as they displayed both heat-sensitive infinite hysteresis and finite hysteresis below the threshold temperature. The phase behavior was characterized in PBS at a polypeptide concentration of 50 μM.

The heat-sensitive, infinite hysteresis of the environmentally responsive polypeptides was found to arise from the emergence of ordered secondary structures that stabilized the insoluble phase. Whereas an environmentally responsive polypeptide that displayed finite hysteresis rapidly recovered its conformational disorder on lowering the temperature below the phase transition temperature adjusted by its degree of hysteresis, environmentally responsive polypeptides with heat-sensitive infinite hysteresis underwent conformational changes that persisted on cooling. An environmentally responsive polypeptide that displayed such a large hysteresis did not exhibit observable reversibility below any given temperature threshold, and displayed ordering on coacervation. Turbidity and CD data were acquired in water at a polypeptide concentration of 5 μM.

The emergence of more ordered secondary structures on phase transition was identified as a primary factor responsible of the increasing degree of hysteresis. Despite the respective degree of hysteresis, which provides a tool for the biomedical and biotechnological exploitation of these materials, the reversible phase transition behavior of all protein-polymers herein described enabled their purification by recursive rounds of phase separation.

Having relaxed the constraints on the distribution of Pro and Gly residues in these protein-polymers, sequence diversity was maximized. The bioinformatics studies underscored the role of overall hydropathicity over local biases in hydrophobicity. Protein-polymers were designed with a target, average hydropathy, but incorporating amino acids with a wide distribution of hydropathies. FIG. 22A shows the generation of protein-polymers composed of hexapeptide motifs wherein only one Pro and one Gly residue are fixed and all residues are otherwise randomized. A target hydropathy of 37° C. was selected to generate a protein-sized biopolymer (240 resides in length) with a widely diverse amino acid composition spanning the entire range of hydropathies (FIG. 22B).

The primary structure of the randomized environmentally responsive polypeptide reported in FIG. 22 was of the form $(Z-Z-P-X-G-Z)_{40}$ and had the following sequence: SKG-PGVPAGHRYPIGGGQPHGKGCPDGVFR-PVGLGAPYGHGAPNGMHRPLGIGKPRGH MYP-KGQGQPMGHLVPDGVGFPRGRKKPVGVGKPIG NGHPIGARTPLGYGMPDGVGMP MGLFLPNGH-GAPHGQGYPAGKLIPKGKGHPFGKGRPL-GAGRPTGFKMPKGLGKPMGVG QPQGHFVPF-GLGQPTGQGAPRGGSQPAGLGHPLGAGAPAGR CHPYGMGVPRGLAMPRG HGQPRGVGYPKGHGWP) (SEQ ID NO: 105). The amino acid sequence included the N terminal peptide SKGP (SEQ ID NO: 106) and the C-terminal tripeptide GWP. The Z and X residues were randomized using a normal distribution with a mean hydropathy of 37° C. and a standard deviation of 50° C.—in order to ensure large sequence diversity.

This protein-polymer behaved as an IDP (FIG. 22C) and displayed phase transition behavior (FIG. 22D). Surprisingly, the target hydropathy was a good predictor of the temperature at which the biopolymer underwent phase separation (~40° C.). This protein-polymer lacked any repeating motif (unlike tropoelastin or resilin), and Pro-X-Gly units were quite rare in all proteins that we analyzed. A "random" biopolymer was designed the size of a short protein-domain (30 amino acids in length). Polymers of this domain displayed phase transition behavior (FIG. 24). Although Gly enrichment observed in the surroundings of the Pro-$X_n$-Gly units for most non-fibrillar Pro and Gly-rich proteins was incorporated, motifs were identified that demonstrate that such Gly enrichment is not necessary for the design of "smart" biopolymers with fully reversible phase transition behavior (FIG. 25).

Gly has a role in modulating the assembly behavior of IDPs. The phase behavior of two protein-polymers were studied wherein Gly was placed preceding a Pro-Gly and a Pro-X-X-Gly unit, and their behavior compared with those of identical motifs where this Gly residue was mutated. Positioning of a Gly residue N-terminal to a Pro-$X_n$-Gly motif enhances the propensity for coacervation—by decreasing the transition temperature (FIGS. 22E-F)—, promotes the formation of irreversible aggregates (FIG. 22E) and leads to changes in assembly behavior (inset of FIG. 22F). This Gly-induced instability was also evidenced on the insoluble expression of these protein-polymers (data not shown), despite their high solubility in PBS once purified. These results underline the role of Gly as a potent modulator of the assembly of IDPs such that this modulatory role may be exploited for the synthesis of "smart" biopolymers that reproduce the assembly behavior and/or mechanical properties of collagen and silks.

The complex phase behaviors indicate a relationship between the syntax of the protein-polymer, its secondary structure and its phase behavior. These structure-function relationships are characteristic of folded proteins. IDPs exhibit highly flexible backbone conformations, but are unlikely to be true random coils. To demonstrate that the polypeptide conformation—as opposed to composition—exerts a potent modulatory role that cannot be explained by a simple random coil model of the disordered state of these polymers, the effect of backbone reversal on phase behavior was studied. Backbone reversal produces a biopolymer that has an identical sequence as the parent biopolymer if read from the C- to the N-terminus, thus having identical hydrophobicity and identical distribution of amino acids (FIG. 22G). However, whereas folded proteins often lose their structure and function on backbone reversal, the effect of backbone reversal on the function (that is, phase behavior) of Pro- and Gly-rich polymers that are intrinsically disordered was unexpectedly found to lead to changes in function (FIG. 21H-J and FIG. 26A), which result from changes in the ensemble of conformations that describe the dynamic backbone of these polymers (FIG. 21K and FIG. 26B-D). This finding suggests that these proteins are unlike synthetic polymers that exist as random coils, and are protein-polymers that are intrinsically disordered. The recurrent link between intrinsic disorder and "smart" behavior suggests that a polypeptide with intrinsic disorder displays "smart" behavior.

Environmentally responsive polypeptides with truly protein-like complexity may exert a biological function encoded in their sequence. Their syntax may also be compatible with sequences that have defined secondary structure propensities as these abound in most proteins. Environmentally responsive polypeptides were made with a repeating unit based on the matrikine motif Gly-X-X-Pro-Gly (SEQ ID NO: 21) (FIG. 4A)—encoding bioactive motifs released on cleavage of various extracellular matrix proteins—, unlike environmentally responsive polypeptides with a disrupted motif but identical composition and phase behavior (FIG. 4B), are capable of preventing tumor growth in a mouse model (FIG. 4C). An environmentally responsive polypeptide inspired in the matrikine motif GXXPG (SEQ ID NO: 21), SM1-24 (250 μM in PBS), was found to prevent the grafting of $1 \times 10^6$ HT1080 tumor cells inoculated into the back of nude mice (FIG. 27). A control polypeptide, SM2-24 (250 μM in PBS), with a disrupted motif but identical phase transition behavior (FIG. 23) had no effect on tumor growth. Tumor volumes were measured 19 days after inoculation.

An environmentally responsive polypeptide was synthesized based on the bioactive site of murine Endostatin, and was found to displays an inverse phase transition temperature reminiscent of other environmentally responsive polypeptides with simpler syntax (FIG. 38). The phase transition of a 5 μM solution of mEndo1-6 in PBS (pH 6.4) (A) was accompanied by a decrease in the disorder of the polypeptide conformation (B), as measured by circular dichroism under identical conditions as in (A).

The diversity of the ensemble of structures observed in our environmentally responsive polypeptides are compatible with protein domains that have very defined local secondary structure propensities. Environmentally responsive polypeptides were synthesized that were composed of the bioactive domains of endostatin from humans and mice, which are well folded protein domains (25-27 amino acids in length) that retain the potent anti-angiogenic activity of endostatin as isolated peptides (FIG. 23D). These environmentally responsive polypeptides that behave as IDPs (FIG. 23E) and display "smart" behavior (FIG. 23F). This is surprising given the partially folded nature of these domains in the native protein (FIG. 23D), the existence of significant regions with high propensities to fold into α-helices and β-sheets in the polymerized polypeptides (FIG. 23G), and the relatively low Pro and Gly content (10% Pro and 14-17% Gly, compared with 20% Pro and 40% Gly in elastin-like polypeptides). Peptide hormones, which often have similar, local secondary structure propensities (FIG. 4G) may be designed and formed from environmentally responsive polypeptides described herein.

Environmentally responsive polypeptides were also made that showed UCST behaviour (FIG. 28). Such polypeptides were found to display reversible UCST behavior in PBS which behavior may be tuned by polypeptide concentration and the number of repeating units. (FIG. 29).

Environmentally responsive polypeptides incorporating the peptide drug GRGDSP were found to be bioactive and their bioactivity could be switched on or off by their phase transition behavior. (FIG. 30; Left panel) Whereas increasing concentrations of (GRGDSPYG)-12 (SEQ ID NO: 44)$_{12}$, which has an UCST below 37° C. and is thus soluble, prevented cell adhesion of PC3-luc-C6 cells after a 3 h treatment, (GRGDSPYG)-20 (SEQ ID NO: 44)$_{20}$, which displayed an UCST above 37° C., had almost no effect on cell adhesion as its concentration increases. (FIG. 30; Right panel) These bioactive environmentally responsive polypeptides were not toxic to the cells as they remained viable when given sufficient time to adhere—perhaps through mechanisms that are not dependent on the integrins targeted by GRGDSP. Control cultures that matched the experimental treatment with the maximum concentration of residual Urea ((GRGDSPYG)-12 (SEQ ID NO: 44)$_{12}$) demonstrated that residual Urea (up to 0.1 M for the 40 µM samples) did not affect cell adhesion or viability.

The UCST behavior of environmentally responsive polypeptides containing RGD tripeptides exhibited a complex response to buffer ionic strength, wherein small concentrations of salt decreased the UCST (due to charge screening) and high concentrations had the opposite effect as they favored hydrophobic interactions (FIG. 31).

The UCST behavior of environmentally responsive polypeptides was modulated by electrostatic interactions between positively and negatively charged amino acids within the sequence (FIG. 32). At pH 2.0, aspartic acid was fully protonated, which largely increased the hydrophobicity of (GRGDSPYG)-20 ((SEQ ID NO: 44)$_{20}$), and yet, instead of observing an increase in its UCST (as it would be expected), a drastic reduction in the UCST was observed that demonstrates the role of electrostatic interactions—here between Arg and Asp residues—in increasing the UCST of these biopolymers.

The UCST behavior of environmentally responsive polypeptides did not require electrostatic interactions (FIG. 33). The aspartic acid in RGD-containing polypeptides was substituted with asparagine and did not eliminate the UCST behavior displayed by these biopolymers. These biopolymers when tested may also have displayed LCST behavior.

The design of RGD-containing environmentally responsive polypeptides that display UCST behavior was found to be compatible with multiple arrangements of Pro and Gly residues. A PG dipeptide, instead of a P-Y-G tripeptide, did not perturb the UCST behavior (FIG. 34). The UCST behavior of the polypeptides was tuned by adjusting the hydrophobicity of the residues comprising the repeating unit. Substituting a Gly residue by a more hydrophilic residue, glutamine, significantly reduced the UCST of the biopolymer (FIG. 35).

Environmentally responsive polypeptides that contain the peptide drug PHSRN (SEQ ID NO: 107) were also found to display UCST behavior (FIG. 36). These biopolymers exhibited reversible phase behavior (left) and were intrinsically disordered (right). The UCST behavior of the polypeptides thus arose from residues capable of intermolecular hydrogen bonding (that is, arginine and serine).

Environmentally responsive polypeptides were designed to display complex phase behaviors wherein the biopolymers display both UCST and LCST, and the LCST is lower than the UCST. (FIG. 37). Environmentally responsive polypeptides with composite motifs composed of one UCST motif and one LCST motif would enable the design of biopolymers that display both UCST and LCST if the LCST is greater than the UCST. Tuning this band-pass behavior will enable the design of environmentally responsive polypeptides that display phase separation only in a very narrow temperature window, which would facilitate the manipulation of complex mixtures of environmentally responsive polypeptides, such as in applications involving multiplexing.

Any patents or publications mentioned in this specification are herein incorporated by reference in their entirety to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

We claim:

1. An environmentally responsive polypeptide comprising at least ten repeats of an amino acid sequence $Z_1PXGZ_2Z_3Z_4Z_5$, wherein P is proline, G is glycine, X is from 0 to 4 amino acids that are not proline or glycine, and $Z_1$, $Z_2$, $Z_3$, $Z_4$ and $Z_5$ are each an amino acid and $Z_2$ is optionally absent, wherein the amino acid sequence comprises (i) an arginine, (ii) serine or an amino acid selected from aspartate and glutamate, or both serine and aspartate or glutamate, and (iii) at least one hydrophobic residue selected from valine, leucine, isoleucine, histidine, tyrosine, tryptophan and alanine, wherein the polypeptide upon stimulation undergoes a conformational change that is accompanied by aggregation.

2. The polypeptide of claim 1, wherein X is HSRN, wherein H is histidine, S is serine, R is arginine and N is asparagine.

3. The polypeptide of claim 1, wherein the at least ten repeats are consecutive.

4. The polypeptide of claim 1, further comprising a spacer sequence between at least two of the at least ten repeats, the spacer sequence comprising from one to twenty-six amino acids.

5. The polypeptide of claim 1, wherein the amino acid sequence comprises an RGD motif, wherein R is arginine, G is glycine and D is aspartate.

6. The polypeptide of claim 1, wherein the amino acid sequence comprises SPXGGRGD or SPXQGRGD, wherein X is a single amino acid.

7. The polypeptide of claim 1, wherein the polypeptide exhibits phase separation when exposed to a threshold temperature that is (i) above a lower critical solution temperature (LCST) of the polypeptide or (ii) below an upper critical solution temperature (UCST) of the polypeptide, or exhibits phase separation when exposed to a threshold temperature that is above the lower critical solution temperature, and when exposed to a threshold temperature that is below the upper critical solution temperature.

8. The polypeptide of claim 7, wherein the phase separation is reversible.

9. The polypeptide of claim 7, wherein the phase separation is irreversible.

10. The polypeptide of claim 1, wherein the polypeptide exhibits heat-irreversible phase separation when exposed to a threshold temperature that is above a lower critical solution temperature of the polypeptide, and exhibits reversible phase separation below the threshold temperature.

11. The polypeptide of claim 1, wherein the polypeptide exhibits a reversible phase separation in response to a first stimulus.

12. The polypeptide of claim 11, wherein the polypeptide exhibits an irreversible phase separation in response to a second different stimulus.

13. The polypeptide of claim 1, wherein the at least 10 repeats convey LCST or UCST transition behavior, and wherein the polypeptide further comprises at least 9 sequences which are interspersed among the at least 10 repeats, wherein the at least 9 sequences convey LCST transition behavior when the at least 10 repeats convey UCST transition behavior, and UCST transition behavior when the at least 10 repeats convey LCST transition behavior, such that the polypeptide displays both LCST and UCST transition behavior.

14. The polypeptide of claim 1, wherein the polypeptide is a polymer comprising diblocks or triblocks of the amino acid sequence.

15. A fusion protein comprising the polypeptide of claim 1.

16. A composition comprising the polypeptide of claim 1, conjugated to a molecule.

17. The composition of claim 16, wherein the molecule is selected from an oligonucleotide, a therapeutic, a carbohydrate, a synthetic polymer, or a combination thereof.

18. A polypeptide comprising the at least ten repeats of the polypeptide of claim 1 as a reverse sequence when read from C-terminus to the N-terminus.

19. A method of effecting a conformational change in a polypeptide comprising exposing the polypeptide of claim 1 to a stimulus such that the polypeptide undergoes a conformational change that is accompanied by aggregation or solubilization in response to the stimulus.

20. The method of claim 19, wherein the polypeptide becomes bioactive or loses bioactivity following the conformational change.

\* \* \* \* \*

SEQUENCE LISTING

```
<160> NUMBER OF SEQ ID NOS: 135

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 1

Gly Pro Gly Gly Xaa
1               5

<210> SEQ ID NO 2
<211> LENGTH: 5
```

```
<212> TYPE: PRT
<213> ORGANISM: Artificial Sequence
<220> FEATURE:
<223> OTHER INFORMATION: Synthetic Peptide

<400> SEQUENCE: 2

Gly Pro Gly Gln Gln
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 3

Val Pro Gly Xaa Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 4

Leu Pro Gly Xaa Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 5

Ile Pro Gly Xaa Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 6

Val Pro Ala Val Gly
1               5

<210> SEQ ID NO 7
<211> LENGTH: 5
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: misc_feature
<222> LOCATION: (4)..(5)
<223> OTHER INFORMATION: Xaa can be any naturally occurring amino acid

<400> SEQUENCE: 7

Gly Pro Gly Xaa Xaa
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 8

Ala Val Pro Gly Val Gly
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 9

Xaa Xaa Pro Gly Xaa Xaa
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 10

Thr Val Pro Gly Ala Gly
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
```

```
<400> SEQUENCE: 11

Xaa Xaa Pro Xaa Gly Xaa
1               5

<210> SEQ ID NO 12
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 12

Gly Ala Pro Phe Gly Phe Ala Ile Pro Met Gly Ala Gly Phe Pro Thr
1               5                   10                  15

Gly Gly Leu Ala Pro Phe Gly Met Gly Leu Pro Ala Gly Met
            20                  25                  30

<210> SEQ ID NO 13
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 13

Xaa Xaa Pro Xaa Gly Xaa Xaa
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 14

Xaa Xaa Pro Xaa Xaa Gly Xaa Xaa
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 15

Xaa Xaa Pro Xaa Xaa Xaa Xaa Gly Xaa Xaa
1               5                   10

<210> SEQ ID NO 16
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 16

Pro Xaa Xaa Gly
1

<210> SEQ ID NO 17
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 17

Val Gly Pro Ala Val Gly
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 18

Val Thr Pro Ala Val Gly
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 19

Val Pro Xaa Gly Xaa Gly
```

1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 20

Xaa Val Pro Gly Xaa Gly
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 21

Gly Xaa Xaa Pro Gly
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa is from 1 to 4 amino acids that are not P
    or G
<220> FEATURE:
<221> NAME/KEY: misc_feature
<222> LOCATION: (6)..(6)
<223> OTHER INFORMATION: Xaa can be any naturally occurring amino acid

<400> SEQUENCE: 22

Xaa Xaa Pro Xaa Gly Xaa
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: MISC_FEATURE

```
<222> LOCATION: (4)..(4)
<223> OTHER INFORMATION: Xaa is from 1 to 4 amino acids that are not P
      or G
<220> FEATURE:
<221> NAME/KEY: misc_feature
<222> LOCATION: (6)..(7)
<223> OTHER INFORMATION: Xaa can be any naturally occurring amino acid

<400> SEQUENCE: 23

Xaa Xaa Pro Xaa Gly Xaa Xaa
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 24

Val Gly Ala Pro Val Gly
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 25

Leu Gly Ala Pro Val Gly
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 26

Val Pro Ser Ala Leu Tyr Gly Val Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 27

Val Ala Pro Val Gly
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 28

Val Thr Pro Ala Val Gly
1               5
```

```
<210> SEQ ID NO 29
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 29

Val Pro Ser Asp Asp Tyr Gly Gln Gly
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 30

Val Pro Ser Asp Asp Tyr Gly Val Gly
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 31

Thr Pro Val Ala Val Gly
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 32

Val Pro Ser Thr Asp Tyr Gly Val Gly
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 33

Val Pro Ala Gly Val Gly
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 34

Val Pro Thr Gly Val Gly
1               5

<210> SEQ ID NO 35
```

```
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 35

Val Pro Ala Gly Leu Gly
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 36

Val Pro His Val Gly
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 37

Val His Pro Gly Val Gly
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 38

Val Pro Gly Ala Val Gly
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 39

Val Pro Gly Val Ala Gly
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 40

Val Arg Pro Val Gly
1               5

<210> SEQ ID NO 41
<211> LENGTH: 7
```

```
<212> TYPE: PRT
<213> ORGANISM: Artificial Sequence
<220> FEATURE:
<223> OTHER INFORMATION: Synthetic Peptide

<400> SEQUENCE: 41

Gly Arg Gly Asp Ser Pro Tyr
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 42

Gly Arg Gly Asp Ser Pro His
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 43

Gly Arg Gly Asp Ser Pro Val
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 44

Gly Arg Gly Asp Ser Pro Tyr Gly
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 45

Arg Pro Leu Gly Tyr Asp Ser
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 46

Arg Pro Ala Gly Tyr Asp Ser
1               5

<210> SEQ ID NO 47
<211> LENGTH: 7
<212> TYPE: PRT
```

```
<213> ORGANISM: Artificial Sequence
<220> FEATURE:
<223> OTHER INFORMATION: Synthetic Peptide

<400> SEQUENCE: 47

Gly Arg Gly Asp Ser Tyr Pro
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 48

Gly Arg Gly Asp Ser Pro Tyr Gln
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 49

Gly Arg Gly Asn Ser Pro Tyr Gly
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 50

Gly Arg Gly Asp Ala Pro Tyr Gln
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 51

Val Pro His Ser Arg Asn Gly Gly
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 52

Val Pro His Ser Arg Asn Gly Leu
1               5

<210> SEQ ID NO 53
<211> LENGTH: 28
<212> TYPE: PRT
<213> ORGANISM: Artificial Sequence
```

<220> FEATURE:
<223> OTHER INFORMATION: Synthetic Peptide

<400> SEQUENCE: 53

Val Pro Gly His Ser His Arg Asp Phe Gln Pro Val Leu His Leu Val
1               5                   10                  15

Ala Leu Asn Ser Pro Leu Ser Gly Gly Met Arg Gly
            20                  25

<210> SEQ ID NO 54
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 54

His Thr His Gln Asp Phe Gln Pro Val Leu His Leu Val Ala Leu Asn
1               5                   10                  15

Thr Pro Leu Ser Gly Gly Met Arg Gly Ile Arg Pro Gly Gly
            20                  25                  30

<210> SEQ ID NO 55
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 55

Phe Glu Trp Thr Pro Gly Trp Tyr Gln Pro Tyr Gly
1               5                   10

<210> SEQ ID NO 56
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 56

Xaa Xaa Pro Gly Xaa Gly
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (7)..(7)
<223> OTHER INFORMATION: Xaa can be any naturally occurring amino acid

<400> SEQUENCE: 57

Gly Arg Gly Asp Ser Pro Xaa Gly
1               5

```
<210> SEQ ID NO 58
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 58

Gly Arg Gly Asp Ser Pro Gly Xaa
1               5

<210> SEQ ID NO 59
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 59

Phe Glu Trp Thr Pro Gly Trp Tyr Gln Pro Tyr
1               5                   10

<210> SEQ ID NO 60
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 60

Glu Ile Leu Asp Val
1               5

<210> SEQ ID NO 61
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 61

Arg Glu Asp Val
1

<210> SEQ ID NO 62
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 62

Met Ser Lys Gly Pro
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 63

His His His His His His Tyr
```

```
<210> SEQ ID NO 64
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 64

Ala Val Pro Gly Val Gly Ala Val Pro Gly Val Gly Ala Val Pro Gly
1               5                   10                  15
Val Gly Ala Val Pro Gly Val Gly Ala Val Pro Gly Val Gly Cys Val
            20                  25                  30
Pro Gly Val Gly
        35

<210> SEQ ID NO 65
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 65

Val Pro Ala Gly Val Gly Val Pro Ala Gly Val Gly Val Pro Ala Gly
1               5                   10                  15
Val Gly Val Pro Ala Gly Val Gly Val Pro Ala Gly Val Gly Val Pro
            20                  25                  30
Cys Gly Val Gly
        35

<210> SEQ ID NO 66
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(5)
<223> OTHER INFORMATION: Xaa can be any naturally occurring amino acid

<400> SEQUENCE: 66

Pro Xaa Xaa Xaa Xaa Gly
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 67

Val Ala Pro Gly Val Gly
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 68
```

```
Gly Val Pro Gly Ala Val
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 69

Gly Val Pro Gly Val Ala
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 70

Thr Val Pro Gly Val Gly
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 71

Thr Val Pro Gly Ala Gly
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 72

Gly Ala Pro Gly Val Gly
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 73

Ala Val Pro Gly Val Ala
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 74
```

Gly Ala Pro Gly Gly Gly
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 75

Gly Ala Pro Gly Ala Gly
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 76

Gly Gly Pro Gly Ala Gly
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 77

Gly Val Pro Ala Gly Val Gly
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 78

Val Gly Pro Val Gly Val Gly
1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 79

Gly Val Pro Thr Gly Val Gly
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 80

Gly Ala Pro Val Gly Val Gly

```
1               5
```

<210> SEQ ID NO 81
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 81

```
Val Ala Pro Val Gly Val Ala
1               5
```

<210> SEQ ID NO 82
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 82

```
Gly Ala Pro Phe Gly Phe Ala
1               5
```

<210> SEQ ID NO 83
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 83

```
Ala Ile Pro Met Gly Ala Gly
1               5
```

<210> SEQ ID NO 84
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 84

```
Gly Phe Pro Thr Gly Gly Leu
1               5
```

<210> SEQ ID NO 85
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 85

```
Leu Ala Pro Phe Gly Met Gly
1               5
```

<210> SEQ ID NO 86
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 86

```
Gly Leu Pro Ala Gly Met Gly
1               5
```

<210> SEQ ID NO 87
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 87

Gly Val Pro Ala Val Gly Val
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 88

Gly Val Pro His Val Gly Val
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 89

Val Gly Pro Ala Val Gly Val
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 90

Val Thr Pro Ala Val Gly Val
1               5

<210> SEQ ID NO 91
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 91

Gly Val Pro Ser Ala Leu Tyr Gly Val Gly
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 92

Gly Val Pro Ser Asp Asp Tyr Gly Gln Gly
1               5                   10

```
<210> SEQ ID NO 93
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 93

Gly Val Pro Ser Asp Asp Tyr Gly Val Gly
1               5                   10

<210> SEQ ID NO 94
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(5)
<223> OTHER INFORMATION: Xaa can be any naturally occurring amino acid

<400> SEQUENCE: 94

Pro Xaa Xaa Xaa Xaa Gly
1               5

<210> SEQ ID NO 95
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa is 4 or less amino acids
<220> FEATURE:
<221> NAME/KEY: MISC_FEATURE
<222> LOCATION: (3)..(3)
<223> OTHER INFORMATION: Xaa is 4 or less amino acids
<220> FEATURE:
<221> NAME/KEY: MISC_FEATURE
<222> LOCATION: (5)..(5)
<223> OTHER INFORMATION: Xaa is 4 or less amino acids

<400> SEQUENCE: 95

Xaa Pro Xaa Gly Xaa
1               5

<210> SEQ ID NO 96
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(4)
<223> OTHER INFORMATION: Xaa can be any naturally occurring amino acid

<400> SEQUENCE: 96

Pro Xaa Xaa Xaa Gly
1               5

<210> SEQ ID NO 97
<211> LENGTH: 5
<212> TYPE: PRT
<213> ORGANISM: Artificial Sequence
<220> FEATURE:
<223> OTHER INFORMATION: Synthetic Peptide
```

```
<400> SEQUENCE: 97

Val Pro Gly Val Gly
1               5

<210> SEQ ID NO 98
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 98

Val Gly Pro Val Gly
1               5

<210> SEQ ID NO 99
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 99

Ala Pro Gly Val Gly
1               5

<210> SEQ ID NO 100
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 100

Xaa Pro Gly Xaa
1

<210> SEQ ID NO 101
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(14)
```

<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 101

Xaa Xaa Pro Xaa Gly Xaa Xaa Xaa Pro Xaa Gly Xaa Xaa Xaa Pro Xaa
1               5                   10                  15

Gly Xaa Xaa Xaa Pro Xaa Gly Xaa Xaa Xaa Pro Xaa Gly Xaa
            20                  25                  30

<210> SEQ ID NO 102
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 102

Pro Xaa Xaa Gly
1

<210> SEQ ID NO 103
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 103

Ala Gln Thr Pro Ser Ser Gln Tyr Gly Ala Pro
1               5                   10

<210> SEQ ID NO 104
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 104

Tyr Gly Ala Pro
1

<210> SEQ ID NO 105

<211> LENGTH: 247
<212> TYPE: PRT
<213> ORGANISM: Artificial Sequence
<220> FEATURE:
<223> OTHER INFORMATION: Synthetic Peptide

<400> SEQUENCE: 105

```
Ser Lys Gly Pro Gly Val Pro Ala Gly His Arg Tyr Pro Ile Gly Gly
1               5                   10                  15

Gly Gln Pro His Gly Lys Gly Cys Pro Asp Gly Val Phe Arg Pro Val
            20                  25                  30

Gly Leu Gly Ala Pro Tyr Gly His Gly Ala Pro Asn Gly Met His Arg
        35                  40                  45

Pro Leu Gly Ile Gly Lys Pro Arg Gly His Met Tyr Pro Lys Gly Gln
    50                  55                  60

Gly Gln Pro Met Gly His Leu Val Pro Asp Gly Val Gly Phe Pro Arg
65                  70                  75                  80

Gly Arg Lys Lys Pro Val Gly Val Gly Lys Pro Ile Gly Asn Gly His
                85                  90                  95

Pro Ile Gly Ala Arg Thr Pro Leu Gly Tyr Gly Met Pro Asp Gly Val
            100                 105                 110

Gly Met Pro Met Gly Leu Phe Leu Pro Asn Gly His Gly Ala Pro His
        115                 120                 125

Gly Gln Gly Tyr Pro Ala Gly Lys Leu Ile Pro Lys Gly Lys Gly His
    130                 135                 140

Pro Phe Gly Lys Gly Arg Pro Leu Gly Ala Gly Arg Pro Thr Gly Phe
145                 150                 155                 160

Lys Met Pro Lys Gly Leu Gly Lys Pro Met Gly Val Gly Gln Pro Gln
                165                 170                 175

Gly His Phe Val Pro Phe Gly Leu Gly Gln Pro Thr Gly Gln Gly Ala
            180                 185                 190

Pro Arg Gly Gly Ser Gln Pro Ala Gly Leu His Pro Leu Gly Ala
        195                 200                 205

Gly Ala Pro Ala Gly Arg Cys His Pro Tyr Gly Met Gly Val Pro Arg
    210                 215                 220

Gly Leu Ala Met Pro Arg Gly His Gly Gln Pro Arg Gly Val Gly Tyr
225                 230                 235                 240

Pro Lys Gly His Gly Trp Pro
                245
```

<210> SEQ ID NO 106
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 106

```
Ser Lys Gly Pro
1
```

<210> SEQ ID NO 107
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 107

```
<210> SEQ ID NO 108
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 108

Pro Phe Leu Arg Phe
1               5

<210> SEQ ID NO 109
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 109

Pro Arg Gln Phe Val
1               5

<210> SEQ ID NO 110
<211> LENGTH: 241
<212> TYPE: PRT
<213> ORGANISM: Artificial Sequence
<220> FEATURE:
<223> OTHER INFORMATION: Synthetic Peptide

<400> SEQUENCE: 110
```

Pro His Ser Arg Asn
1               5

Gly Val Gly Pro Ala Gly His Arg Tyr Pro Ile Gly Gly Gln Gly Pro
1               5                   10                  15

His Gly Lys Cys Gly Pro Asp Gly Val Phe Arg Pro Val Gly Leu Ala
                20                  25                  30

Gly Pro Tyr Gly His Ala Gly Pro Asn Gly Met His Arg Pro Leu Gly
            35                  40                  45

Ile Lys Gly Pro Arg Gly His Met Tyr Pro Lys Gly Gln Gln Gly Pro
        50                  55                  60

Met Gly His Leu Val Pro Asp Gly Val Phe Gly Pro Arg Gly Arg Lys
65                  70                  75                  80

Lys Pro Val Gly Val Lys Gly Pro Ile Gly Asn His Gly Pro Ile Gly
                85                  90                  95

Ala Arg Thr Pro Leu Gly Tyr Met Gly Pro Asp Gly Val Met Gly Pro
                100                 105                 110

Met Gly Leu Phe Leu Pro Asn Gly His Ala Gly Pro His Gly Gln Tyr
            115                 120                 125

Gly Pro Ala Gly Lys Leu Ile Pro Lys Gly Lys His Gly Pro Phe Gly
        130                 135                 140

Lys Arg Gly Pro Leu Gly Ala Arg Gly Pro Thr Gly Phe Lys Met Pro
145                 150                 155                 160

Lys Gly Leu Lys Gly Pro Met Gly Val Gln Gly Pro Gln Gly His Phe
                165                 170                 175

Val Pro Phe Gly Leu Gln Gly Pro Thr Gly Gln Ala Gly Pro Arg Gly
                180                 185                 190

Gly Ser Gln Pro Ala Gly Leu His Gly Pro Leu Gly Ala Ala Gly Pro
            195                 200                 205

Ala Gly Arg Cys His Pro Tyr Gly Met Val Gly Pro Arg Gly Leu Ala

```
                    210                 215                 220
Met Pro Arg Gly His Gln Gly Pro Arg Gly Val Tyr Gly Pro Lys Gly
            225                 230                 235                 240

His

<210> SEQ ID NO 111
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 111

Val Pro Gly Val Ala
1               5

<210> SEQ ID NO 112
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 112

Val Ala Pro Gly Ala Gly
1               5

<210> SEQ ID NO 113
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa is 0 to 4 amino acids that are not P or G
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 113

Xaa Pro Xaa Gly Xaa Arg Gly Xaa
1               5

<210> SEQ ID NO 114
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 114

Ala Pro Val Gly Val Gly
1               5

<210> SEQ ID NO 115
<211> LENGTH: 6
<212> TYPE: PRT
```

```
<213> ORGANISM: Artificial Sequence
<220> FEATURE:
<223> OTHER INFORMATION: Synthetic Peptide

<400> SEQUENCE: 115

Ala Pro Val Gly Leu Gly
1               5

<210> SEQ ID NO 116
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 116

Val Xaa Pro Val Gly
1               5

<210> SEQ ID NO 117
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 117

Val Xaa Pro Ala Val Gly
1               5

<210> SEQ ID NO 118
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 118

Gly Val Ala Pro Val
1               5

<210> SEQ ID NO 119
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 119

Gly Val Gly Pro Val
1               5

<210> SEQ ID NO 120
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 120
```

```
Gly Val Gly Ala Pro Val
1               5
```

<210> SEQ ID NO 121
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 121

```
Gly Ala Val Pro Gly Val Gly Ala Val Pro Gly Val Gly Ala Val Pro
1               5                   10                  15

Gly Val Gly Ala Val Pro Gly Val Gly Cys Val Pro Gly Val
            20                  25                  30
```

<210> SEQ ID NO 122
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 122

```
Gly Val Pro Ala Gly Val Gly Val Pro Ala Gly Val Gly Val Pro Ala
1               5                   10                  15

Gly Val Gly Val Pro Ala Gly Val Gly Val Pro Cys Gly Val
            20                  25                  30
```

<210> SEQ ID NO 123
<211> LENGTH: 56
<212> TYPE: PRT
<213> ORGANISM: Artificial Sequence
<220> FEATURE:
<223> OTHER INFORMATION: Synthetic Peptide

<400> SEQUENCE: 123

```
Val Pro Gly His Ser His Arg Asp Phe Gln Pro Val Leu His Leu Val
1               5                   10                  15

Ala Leu Asn Ser Pro Leu Ser Gly Gly Met Arg Gly Val Pro Gly His
            20                  25                  30

Ser His Arg Asp Phe Gln Pro Val Leu His Leu Val Ala Leu Asn Ser
        35                  40                  45

Pro Leu Ser Gly Gly Met Arg Gly
    50                  55
```

<210> SEQ ID NO 124
<211> LENGTH: 60
<212> TYPE: PRT
<213> ORGANISM: Artificial Sequence
<220> FEATURE:
<223> OTHER INFORMATION: Synthetic Peptide

<400> SEQUENCE: 124

```
His Thr His Gln Asp Phe Gln Pro Val Leu His Leu Val Ala Leu Asn
1               5                   10                  15

Thr Pro Leu Ser Gly Gly Met Arg Gly Ile Arg Pro Gly Gly His Thr
            20                  25                  30

His Gln Asp Phe Gln Pro Val Leu His Leu Val Ala Leu Asn Thr Pro
        35                  40                  45

Leu Ser Gly Gly Met Arg Gly Ile Arg Pro Gly Gly
    50                  55                  60
```

```
<210> SEQ ID NO 125
<211> LENGTH: 74
<212> TYPE: PRT
<213> ORGANISM: Artificial Sequence
<220> FEATURE:
<223> OTHER INFORMATION: Synthetic Peptide

<400> SEQUENCE: 125

Asp Val Ser Thr Pro Pro Thr Val Leu Pro Asp Asn Phe Pro Arg Tyr
1               5                   10                  15

Pro Val Gly Lys Phe Phe Gln Tyr Asp Thr Trp Lys Gln Ser Thr Gln
            20                  25                  30

Arg Leu Pro Gly Gly Asp Val Ser Thr Pro Pro Thr Val Leu Pro Asp
        35                  40                  45

Asn Phe Pro Arg Tyr Pro Val Gly Lys Phe Phe Gln Tyr Asp Thr Trp
    50                  55                  60

Lys Gln Ser Thr Gln Arg Leu Pro Gly Gly
65                  70

<210> SEQ ID NO 126
<211> LENGTH: 52
<212> TYPE: PRT
<213> ORGANISM: Artificial Sequence
<220> FEATURE:
<223> OTHER INFORMATION: Synthetic Peptide

<400> SEQUENCE: 126

Phe Asn Ala Pro Phe Asp Val Gly Ile Lys Leu Ser Gly Val Gln Tyr
1               5                   10                  15

Gln Gln His Ser Gln Ala Leu Pro Gly Gly Phe Asn Ala Pro Phe Asp
            20                  25                  30

Val Gly Ile Lys Leu Ser Gly Val Gln Tyr Gln Gln His Ser Gln Ala
        35                  40                  45

Leu Pro Gly Gly
    50

<210> SEQ ID NO 127
<211> LENGTH: 66
<212> TYPE: PRT
<213> ORGANISM: Artificial Sequence
<220> FEATURE:
<223> OTHER INFORMATION: Synthetic Peptide

<400> SEQUENCE: 127

Arg Ser Leu Gln Asp Thr Glu Glu Lys Ser Arg Ser Phe Ser Ala Ser
1               5                   10                  15

Gln Ala Asp Pro Leu Ser Asp Pro Asp Gln Met Asn Glu Asp Pro Gly
            20                  25                  30

Gly Arg Ser Leu Gln Asp Thr Glu Glu Lys Ser Arg Ser Phe Ser Ala
        35                  40                  45

Ser Gln Ala Asp Pro Leu Ser Asp Pro Asp Gln Met Asn Glu Asp Pro
    50                  55                  60

Gly Gly
65

<210> SEQ ID NO 128
<211> LENGTH: 72
<212> TYPE: PRT
<213> ORGANISM: Artificial Sequence
<220> FEATURE:
<223> OTHER INFORMATION: Synthetic Peptide
```

<400> SEQUENCE: 128

Thr Arg Ser Ala Trp Leu Asp Ser Gly Val Thr Gly Ser Gly Leu Glu
1               5                   10                  15

Gly Asp His Leu Ser Asp Thr Ser Thr Thr Ser Leu Glu Leu Asp Ser
            20                  25                  30

Arg Pro Gly Gly Thr Arg Ser Ala Trp Leu Asp Ser Gly Val Thr Gly
        35                  40                  45

Ser Gly Leu Glu Gly Asp His Leu Ser Asp Thr Ser Thr Thr Ser Leu
    50                  55                  60

Glu Leu Asp Ser Arg Pro Gly Gly
65                  70

<210> SEQ ID NO 129
<211> LENGTH: 62
<212> TYPE: PRT
<213> ORGANISM: Artificial Sequence
<220> FEATURE:
<223> OTHER INFORMATION: Synthetic Peptide

<400> SEQUENCE: 129

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg Pro Gly Gly Gly
            20                  25                  30

Ser Ser Phe Leu Ser Pro Glu His Gln Arg Val Gln Gln Arg Lys Glu
        35                  40                  45

Ser Lys Lys Pro Pro Ala Lys Leu Gln Pro Arg Pro Gly Gly
    50                  55                  60

<210> SEQ ID NO 130
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 130

Gly Val Gly Pro Ala Val
1               5

<210> SEQ ID NO 131
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa is 0 to 4 amino acids that are not P or G
<220> FEATURE:
<221> NAME/KEY: misc_feature
<222> LOCATION: (5)..(8)
<223> OTHER INFORMATION: Xaa can be any naturally occurring amino acid

<400> SEQUENCE: 131

Xaa Pro Xaa Gly Xaa Xaa Xaa Xaa
1               5

```
<210> SEQ ID NO 132
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 132

Ala Pro Gly Val Gly Pro
1               5

<210> SEQ ID NO 133
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 133

Gly Arg Gly Asp Ser Pro
1               5

<210> SEQ ID NO 134
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 134

Xaa Xaa Pro Xaa Xaa Gly Xaa
1               5

<210> SEQ ID NO 135
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: X is not P

<400> SEQUENCE: 135

Val Pro Gly Xaa Gly
1               5
```